(12) United States Patent
Khan

(10) Patent No.: US 10,618,875 B2
(45) Date of Patent: Apr. 14, 2020

(54) PHENYL DERIVATIVES

(71) Applicant: Rivus Pharmaceuticals, Inc., Charlottesville, VA (US)

(72) Inventor: Shaharyar Khan, Charlottesville, VA (US)

(73) Assignee: Rivus Pharmaceuticals, Inc., Charlottesville, VA (US)

( * ) Notice: Subject to any disclaimer, the term of this patent is extended or adjusted under 35 U.S.C. 154(b) by 0 days.

(21) Appl. No.: 16/475,390

(22) PCT Filed: Jan. 5, 2018

(86) PCT No.: PCT/US2018/012491
§ 371 (c)(1),
(2) Date: Jul. 2, 2019

(87) PCT Pub. No.: WO2018/129258
PCT Pub. Date: Jul. 12, 2018

(65) Prior Publication Data
US 2019/0337903 A1     Nov. 7, 2019

Related U.S. Application Data

(60) Provisional application No. 62/443,244, filed on Jan. 6, 2017, provisional application No. 62/581,355, filed on Nov. 3, 2017, provisional application No. 62/585,326, filed on Nov. 13, 2017.

(51) Int. Cl.
| | |
|---|---|
| *C07D 233/88* | (2006.01) |
| *A61P 1/16* | (2006.01) |
| *A61P 3/06* | (2006.01) |
| *A61P 3/10* | (2006.01) |

(52) U.S. Cl.
CPC ............... *C07D 233/88* (2013.01); *A61P 1/16* (2018.01); *A61P 3/06* (2018.01); *A61P 3/10* (2018.01)

(58) Field of Classification Search
CPC .................................................. C07D 233/88
See application file for complete search history.

(56) References Cited

U.S. PATENT DOCUMENTS

| | | |
|---|---|---|
| 7,645,791 B2 | 1/2010 | Olesen et al. |
| 7,939,690 B2 | 5/2011 | Petersen et al. |
| 8,946,275 B2 | 2/2015 | Curd et al. |
| 9,763,896 B2 | 9/2017 | Alonso et al. |
| 2004/0138301 A1 | 7/2004 | Hansen |
| 2007/0004799 A1 | 1/2007 | Olesen |
| 2007/0010559 A1 | 1/2007 | Christiansen |
| 2010/0063122 A1 | 3/2010 | Peterson |
| 2010/0249161 A1 | 9/2010 | Petersen |
| 2013/0203843 A1 | 8/2013 | Skulachev |
| 2016/0008298 A1 | 1/2016 | Stevens |
| 2016/0199310 A1 | 7/2016 | Shulman |
| 2016/0207873 A1 | 7/2016 | Shulman |
| 2017/0240563 A1 | 8/2017 | Hoehn |
| 2017/0252347 A1 | 9/2017 | Geisler |

FOREIGN PATENT DOCUMENTS

| | | | |
|---|---|---|---|
| EP | 1625112 | 7/2009 | |
| EP | 2086951 | 12/2011 | |
| WO | WO-9325536 A1 * | 12/1993 | ............. A61K 31/12 |
| WO | 2010049768 | 5/2010 | |
| WO | 2016004363 | 1/2016 | |
| WO | 2018217757 | 11/2018 | |

OTHER PUBLICATIONS

Abulizi et al. A controlled-release mitochondrial protonophore reverses hypertriglyceridemia, nonalcoholic steatohepatitis, and diabetes in lipodystrophic mice. The FASEB Journal. 2017; 31; pp. 2916-2924.
Coleman et al. Assessing the Toxicity and Bioavailability of 2,4-Dinitroanisole in Acute and Sub-chronic Exposures using the Earthword, Eisenia Fetida. U.S. Army Corps of Engineers.Jun. 14, 2010.
Goldgof et al. The Chemical Uncoupler 2,4-Dinitrophenol (DNP) Protects against Diet-Inducted Obesity and Improves Energy Homeostasis in Mice at Thermoneutrality. The Journal of Biological Chemistry. vol. 289, No. 28, pp. 19341-19350 (Jul. 7, 2014).
Lent, Emily May et al. U.S. Army Public Health Command. Toxicology Study No. 87-XE-ODBP, Jun. 10, 2012. The Subchronic Oral Toxicity of 2,4-Dinitroanisole (DNAN) in Rats, Sep. 2010-Mar. 2011.
Perry et al. Reversal of Hypertriglyceridemia, Fatty Liver Disease and Insulin Resistance by a Liver-Targeted Mitochondrial Uncoupler. Cell Metab. Nov. 5, 2013; 18(5): 740-748.
Samuel. Mechanism of Hepatic Insulin Resistance in Non-Alcoholic Fatty Liver Disease. Journal of Biological Chemistry. (May 27, 2004) M3:13478.
Wei et al. Sustained-release mitochondrial protonophore reverses nonalcoholic fatty liver disease in rats. International Journal of Pharmaceutics; 530 (Jul. 25, 2017) pp. 230-238.
Wu et al. 2,4 DNP improves motor function, preserves medium spiny neuronal identity, and reduces oxidative stress in a mouse model of Huntington's disease. Experimental Neurology 293 (2017) pp. 83-90.

* cited by examiner

*Primary Examiner* — Jeffrey S Lundgren
*Assistant Examiner* — Tori Strong
(74) *Attorney, Agent, or Firm* — Honigman LLP; Lucy X. Yang; Jonathan P. O'Brien

(57) ABSTRACT

The present application provides a novel phenyl derivative, 5-[(2,4-dinitrophenoxy)methyl]-1-methyl-2-nitro-1H-imidazole or a pharmaceutically acceptable salt thereof, which is useful for regulating mitochondria activity, reducing adiposity, treating diseases including diabetes and diabetes-associated complications.

13 Claims, 33 Drawing Sheets

Evaluation of the Effect of cmpA in MCD diet induced NASH mouse model cmpA reduces steatohepatitis and inflammatory cytokines in MCD diet-induced NASH mouse liver. Lipid droplets were reduced after 6 weeks of treatment The Effect of Sorafenib alone and in combination with cmpA in the Treatment of Orthotopic Model of Human Hep3B-luc Hepatic Cancer Formation of DNP from 2uM cmpA in liver microsomes from different species

PHENYL DERIVATIVES

PRIORITY claim

This application is a 35 U.S.C. § 371 U.S. National Phase Application of, and claims priority to, PCT Application No.: PCT/US2018/012491, filed Jan. 5, 2018, which claims priority to U. S. Provisional Application Ser. No. 62/443,244, filed Jan. 6, 2017; U. S. Provisional Application Ser. No. 62/581,355, filed Nov. 3, 2017; and U.S. Provisional Application Ser. No. 62/585,326, filed Nov. 13, 2017.

FIELD OF THE INVENTION

The present application provides novel phenyl derivatives. The novel compounds are useful for regulating mitochondria activity, reducing adiposity, treating diseases including diabetes and diabetes-associated complications.

BACKGROUND OF THE INVENTION

Obesity is a well-known risk factor for the development of many common diseases such as type 2 diabetes (T2D) and non-alcoholic fatty liver disease (NAFLD). Obesity is best viewed as any degree of excess adiposity that imparts a health risk. When energy intake exceeds expenditure, the excess calories are stored predominately in adipose tissue, and if this net positive balance is prolonged, obesity results, i.e. there are two components to weight balance, and an abnormality on either side (intake or expenditure) can lead to obesity. This process may be counteracted by increasing the energy expenditure or decreasing the energy intake. There is, therefore, a need for pharmaceutical agents that are capable of controlling excess adipose tissue for instance by increasing the energy expenditure or decreasing the energy intake.

The body gets energy through the oxidation of food such as glucose and fatty acids. It is known that mitochondria control metabolism in individual cells by burning sugars and fats. One of its primary functions is oxidative phosphorylation, a process through which energy derived from metabolism of fuels like glucose or fatty acids is converted to ATP. The generation of ATP in the mitochondria is coupled to the oxidation of NADH which results in the transportation of protons in the electron transport chain. Chemical uncouplers can inhibit efficient energy (ATP) production in cells with mitochondria. They uncouple oxidative phosphorylation by carrying protons across the mitochondrial membrane, leading to a rapid consumption of energy (the energy expenditure) without generation of ATP. In other words, the uncouplers flood the mitochondrial matrix with protons, and the oxidation of NADH continues but instead of generating energy in the form of ATP, the energy of the proton gradient is lost as heat.

The manipulation of chemical uncouplers of mitochondria in order to decrease fat deposits has been a scientific goal for more than eighty years. See Simkins S "Dinitrophenol and desiccated thyroid in the treatment of obesity: a comprehensive clinical and laboratory study". J Am Med Assoc 108: 2110-2117 (1937) and Fleury C et al, Nature Genetics 15, 269-272 (1997), *Uncoupling Protein-2: A Novel Gene Linked to Obesity and Hyperinsulinemia*. The best known chemical uncoupler is 2,4-dinitrophenol (DNP), which has been shown to increase energy expenditure in humans as well as animals. However, chemical uncouplers are often toxic. Concerns about dangerous side-effects led to the removal of DNP from the market.

There is a need for safe mitochondrial uncouplers that can safely produce the desired medical effect without harming the individual. The novel phenyl derivatives disclosed herein satisfy these needs.

SUMMARY OF THE INVENTION

Disclosed herein is a novel compound, 5-[(2,4-dinitrophenoxy)methyl]-1-methyl-2-nitro-1H-imidazole or a pharmaceutically acceptable salt thereof (Compound A).

Also disclosed herein are novel compounds of Formula I

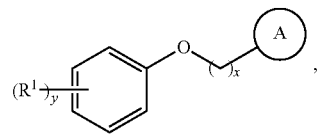

Formula I or a pharmaceutically acceptable salt thereof, wherein
ring A is imidazole, substituted with 1 to 3 substituents independently selected from —$NO_2$ and methyl;
each $R^1$ is independently halo, cyano, $NO_2$, —C(O)H, —COOH, —C(O)O($C_{1-4}$ alkyl), —C(O)($C_{1-4}$ alkyl), $C_{1-4}$ alkyl, $C_{1-4}$ alkenyl, or $C_{1-4}$ alkynyl, wherein said $C_{1-4}$ alkyl, $C_{1-4}$ alkenyl, and $C_{1-4}$ alkynyl are each independently and optionally substituted with 1 to 3 substituents selected from the group consisting of halo, $NO_2$, and cyano;
y is 1, 2, or 3; and
x is an integer from 1 to 6.

In some embodiments, ring A is imidazole, substituted with 2 substituents independently selected from —$NO_2$ and methyl;
each $R^1$ is independently halo, $NO_2$, $C_{1-4}$ alkyl, $C_{1-4}$ alkenyl, and $C_{1-4}$ alkynyl, wherein said $C_{1-4}$ alkyl and $C_{1-4}$ alkenyl are each independently and optionally substituted with 1 to 3 substituents selected from the group consisting of halo, NO2, and cyano;
y is 1, 2, or 3; and
x is an integer from 1 to 3.

In some embodiments, ring A is imidazole, substituted with 2 substituents independently selected from —$NO_2$ and methyl;
each $R^1$ is independently halo, or $NO_2$;
y is 1, 2, or 3; and
x is an integer from 1 to 2.

In some embodiments, ring A is imidazole, substituted with 2 substituents independently selected from —$NO_2$ and methyl;
each $R^1$ is independently halo, or $NO_2$;
y is 1, 2, or 3; and
x is an integer from 1 to 2.

In some embodiments, ring A is imidazole, substituted with 2 substituents independently selected from —$NO_2$ and methyl;
each $R^1$ is $NO_2$;
y is 1 or 2; and
x is an integer from 1 to 2.

In some embodiments, ring A is imidazole, substituted with 2 substituents independently selected from —$NO_2$ and methyl;
each $R^1$ is $NO_2$;
y is 2; and
x is 1.

The novel compounds of the invention are useful for regulating mitochondria activities, reducing adiposity, treating diseases including metabolic disorders, diabetes or diabetes-associated complications such as heart disease and renal failure, and moderating or controlling of weight gain in a mammal.

DETAILED DESCRIPTION

Definitions

Figure 1:
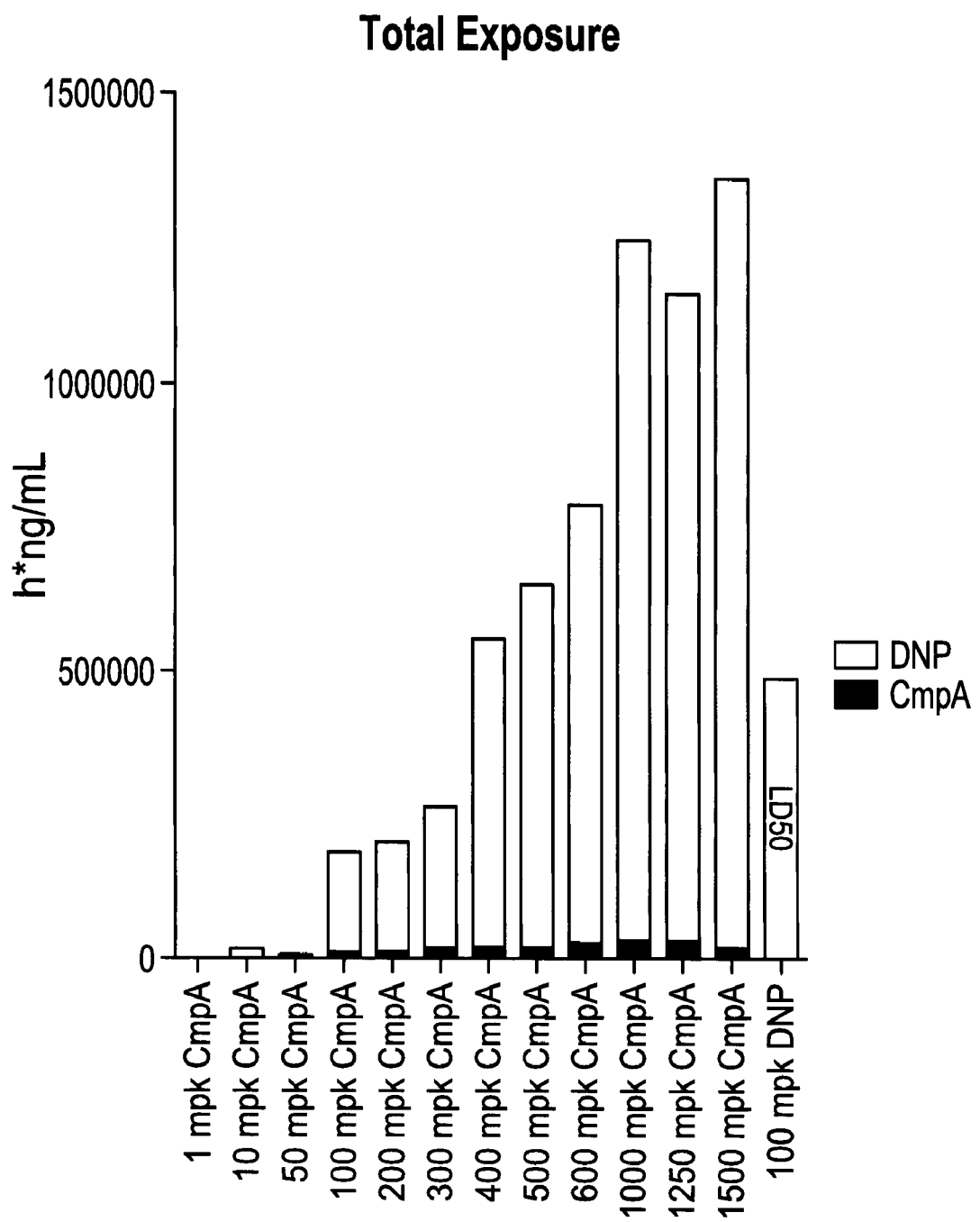
FIG. 1 illustrates total exposure of DNP (gray) and Compound A (black) calculated by the area under the curve (AUC) during the first 24 hours after oral administration of the compound and its respective concentration that is indicated under the x-axis. Half of the animals that were given DNP did not survive the study, establishing LD50 for DNP to 100 mpk.

As used herein, all terms used herein have the meaning as commonly understood by a person skilled in the art in the pharmaceutical field.

As used herein, an effective amount is defined as the amount required to confer a therapeutic effect on the treated patient, and is typically determined based on age, surface area, weight, and condition of the patient.

As used herein, the term "mammal", "patient" or "subject" refers to any animal including human, livestock and companion animals. The phrase "companion animal" or "companion animals" refers to animals kept as pets. Examples of companion animals include cats, dogs, and horses.

As used herein, the term "controlling", "treating" or "treatment" of a condition includes: (1) inhibiting the disease, conditions or disorders, i.e., arresting or reducing the development of the disease or its clinical symptoms/signs; or (2) relieving the disease, i.e., causing regression of the disease or its clinical symptoms/signs.

As used herein, "pharmaceutically acceptable" means suitable for use in mammals, companion animals or livestock animals.

As used herein, the terms "DNP" refers to 2,4-dinitrophenol or a salt, solvate or adduct thereof.

As used herein, the term "metabolic disorder" refers to a condition characterized by an alteration or disturbance in metabolic function.

As used herein, the phrase "pharmaceutically acceptable salt" refers to a salt that is pharmaceutically acceptable non-toxic acids, including inorganic acids, organic acids, solvates, or hydrates thereof.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material In one aspect, the invention provides novel compounds of Formula I

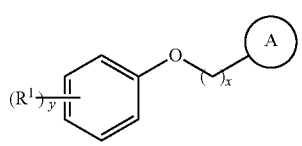

Formula I or a pharmaceutically acceptable salt thereof, wherein ring A is imidazole, substituted with 1 to 3 substituents independently selected from —$NO_2$ and methyl;
each $R^1$ is independently halo, cyano, $NO_2$, —C(O)H, —COOH, —C(O)O($C_{1-4}$ alkyl), —C(O)($C_{1-4}$ alkyl), $C_{1-4}$ alkyl, $C_{1-4}$ alkenyl, or $C_{1-4}$ alkynyl, wherein said $C_{1-4}$ alkyl, $C_{1-4}$ alkenyl, and $C_{1-4}$ alkynyl are each independently and optionally substituted with 1 to 3 substituents selected from the group consisting of halo, $NO_2$, and cyano;
y is 1, 2, or 3; and
x is an integer from 1 to 6.

In some embodiments, ring A is imidazole, substituted with 2 substituents independently selected from —$NO_2$ and methyl;
each $R^1$ is independently halo, $NO_2$, $C_{1-4}$ alkyl, $C_{1-4}$ alkenyl, and $C_{1-4}$ alkynyl, wherein said $C_{1-4}$ alkyl and $C_{1-4}$ alkenyl are each independently and optionally substituted with 1 to 3 substituents selected from the group consisting of halo, $NO_2$, and cyano;
y is 1, 2, or 3; and
x is an integer from 1 to 3.

In some embodiments, ring A is imidazole, substituted with 2 substituents independently selected from —$NO_2$ and methyl;
each $R^1$ is independently halo, or $NO_2$;
y is 1, 2, or 3; and
x is an integer from 1 to 2.

In some embodiments, ring A is imidazole, substituted with 2 substituents independently selected from —$NO_2$ and methyl;
each $R^1$ is independently halo, or $NO_2$;
y is 1, 2, or 3; and
x is an integer from 1 to 2.

In some embodiments, ring A is imidazole, substituted with 2 substituents independently selected from —$NO_2$ and methyl;
each $R^1$ is $NO_2$;
y is 1 or 2; and
x is an integer from 1 to 2.

In some embodiments, ring A is imidazole, substituted with 2 substituents independently selected from —$NO_2$ and methyl;
each $R^1$ is $NO_2$;
y is 2; and
x is 1.

In some embodiments, ring A is 1-imidazolyl, 5-imidazolyl, or 2-imidazolyl.

In some embodiments, ring A is 1-imidazolyl or 5-imidazolyl.

In some embodiments, ring A is 1-imidazolyl.
In some embodiments, ring A is 5-imidazolyl.
In some embodiments, ring A is 2-imidazolyl.
In some embodiments, ring A is

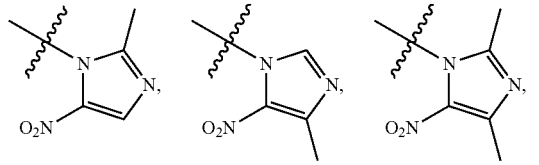

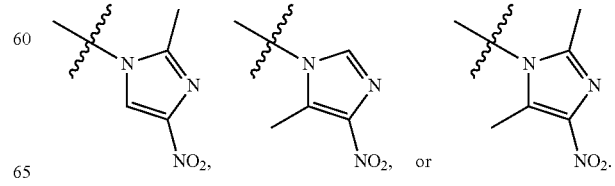

In some embodiments, ring A is

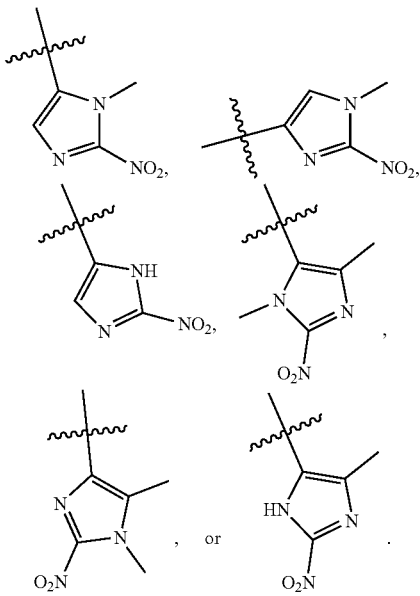

In some embodiments, ring A is

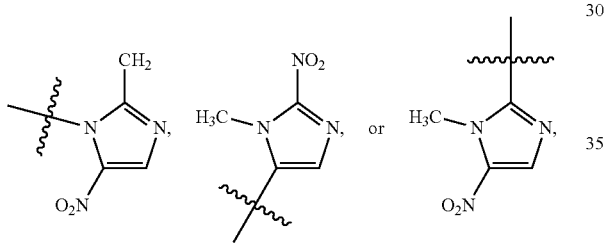

In some embodiments, each $R^1$ is independently halo, cyano, $NO_2$, $C_{1-4}$ alkyl or $C_{1-4}$ alkenyl, wherein said $C_{1-4}$ alkyl and $C_{1-4}$ alkenyl are each independently and optionally substituted with 1 to 3 cyano or fluoro substituents.

In some embodiments, the halo substituent is selected from Cl and Br. In another embodiment, $R^1$ is $CH_2F$, $CHF_2$, or $CF_3$.

In some embodiments, each $C_{1-4}$ alkyl is independently methyl, ethyl, propyl, or butyl. In some further embodiments, each $C_{1-4}$ alkyl is independently propyl or butyl. In still further embodiments, each $C_{1-4}$ alkyl is independently butyl. In a further embodiment, each $C_{1-4}$ alkyl is tert-butyl.

In some embodiments, each $C_{1-4}$ alkenyl is independently ethenyl, allyl, but-3-en-1-yl, or but-2-en-1-yl, optionally substituted with 1 to 3 cyano substituents. In some further embodiments, said $C_{1-4}$ alkenyl is substituted with two cyano substituents. In a further embodiment, said $C_{1-4}$ alkenyl is

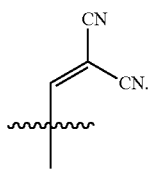 [SMILES: *C=C(C#N)C#N]

In some embodiments, $R^1$ is $NO_2$.
In some embodiments, $R^1$ is halo or $NO_2$.
In some embodiments, y is 2 and each $R^1$ is $NO_2$ or halo.
In some embodiments, the moiety

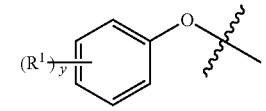

is selected from

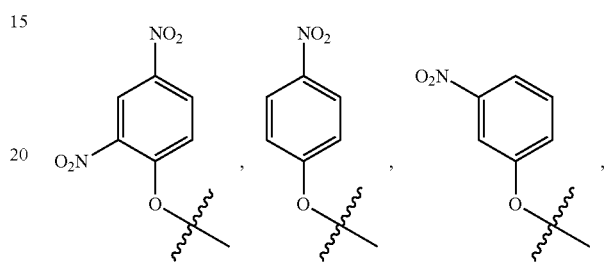

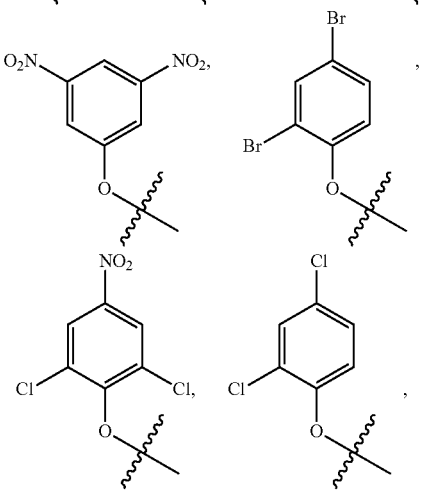

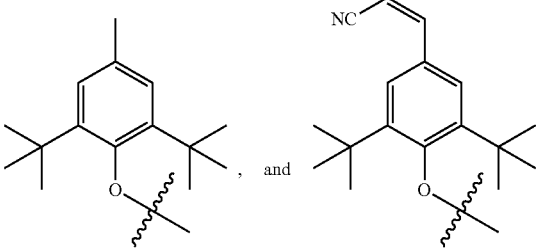

In some embodiments, each $R^1$ is independently halo, cyano, $NO_2$, $C_{1-4}$ alkyl or $C_{1-4}$ alkenyl, wherein said $C_{1-4}$ alkyl and $C_{1-4}$ alkenyl are each independently and optionally substituted with 1 to 3 cyano substituents and ring A is imidazole, substituted with 2 substituents independently selected from —$NO_2$ or methyl; or ring A is imidazole, substituted with one —$NO_2$ and one methyl; or ring A is selected from the group consisting of 1-imidazolyl, 5-imidazolyl, and 2-imidazolyl; or ring A is selected from the group consisting of 1-imidazolyl and 5-imidazolyl; or ring A is 1-imidazolyl; or ring A is 5-imidazolyl; or ring A is 2-imidazolyl; or ring A is:

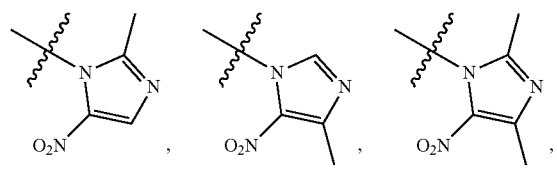

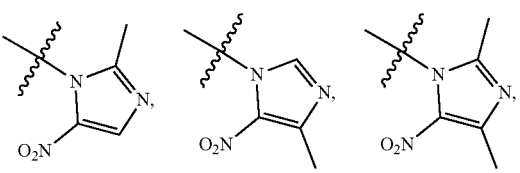

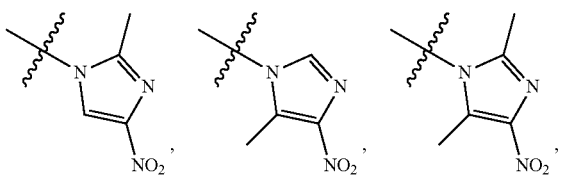

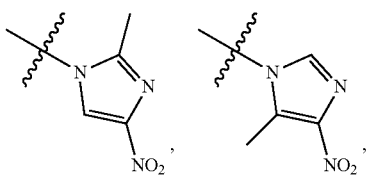

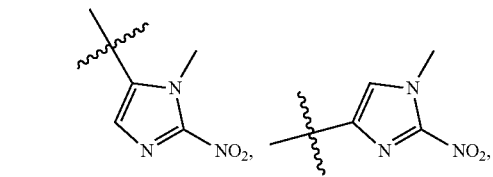

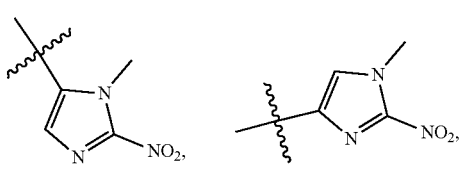

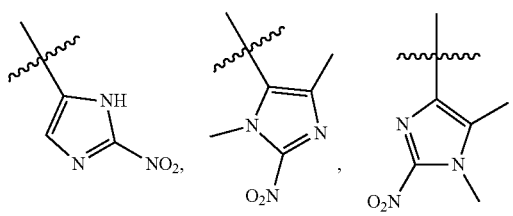

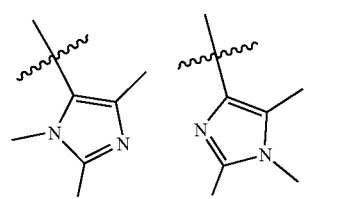

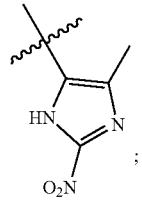

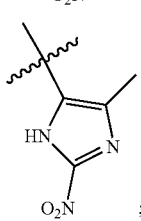

or ring A is selected from or ring A is selected from

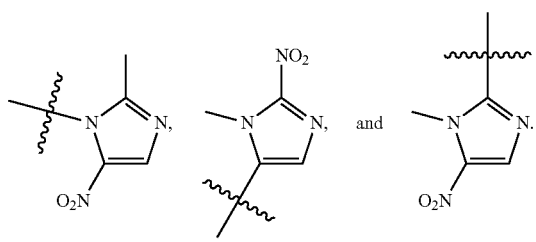

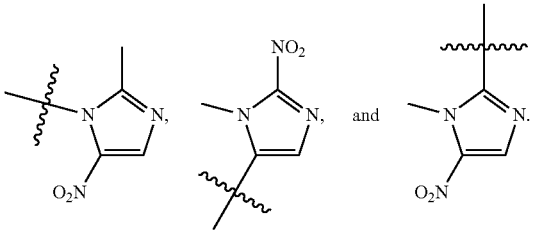

In some embodiments, each $R^1$ is independently Cl, Br, cyano, $NO_2$, methyl, ethyl, propyl, butyl ethenyl, allyl, but-3-en-1-yl, or but-2-en-1-yl, wherein said ethenyl, allyl, but-3-en-1-yl, or but-2-en-1-yl is optionally substituted with 1 to 3 cyano substituents and ring A is imidazole, substituted with 2 substituents independently selected from —$NO_2$ or methyl; or ring A is imidazole, substituted with one —$NO_2$ and one methyl; or ring A is selected from the group consisting of 1-imidazolyl, 5-imidazolyl, and 2-imidazolyl; or ring A is selected from the group consisting of 1-imidazolyl and 5-imidazolyl; or ring A is 1-imidazolyl; or ring A is 5-imidazolyl; or ring A is 2-imidazolyl; or ring A is In some embodiments, each $R^1$ is independently Cl, Br, cyano, $NO_2$, methyl, ter-butyl, or ethenyl, wherein said ethenyl is optionally substituted with 1 to 3 cyano substituents and ring A is imidazole, substituted with 2 substituents independently selected from —$NO_2$ or methyl; or ring A is imidazole, substituted with one —$NO_2$ and one methyl; or ring A is selected from the group consisting of 1-imidazolyl, 5-imidazolyl, and 2-imidazolyl; or ring A is selected from the group consisting of 1-imidazolyl and 5-imidazolyl; or ring A is 1-imidazolyl; or ring A is 5-imidazolyl; or ring A is 2-imidazolyl; or ring A is

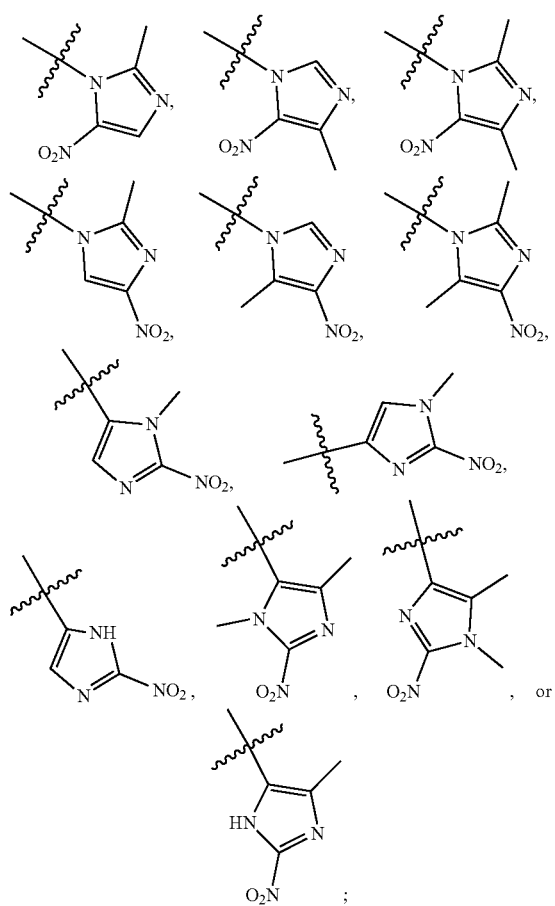

or ring A is selected from

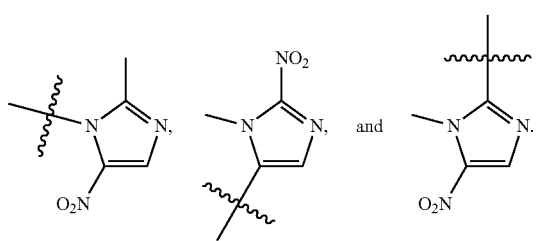

In some embodiments, the moiety

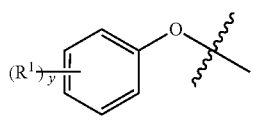

is selected from

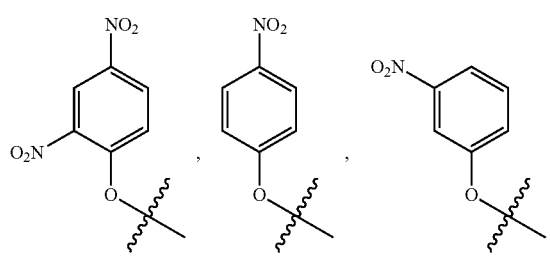

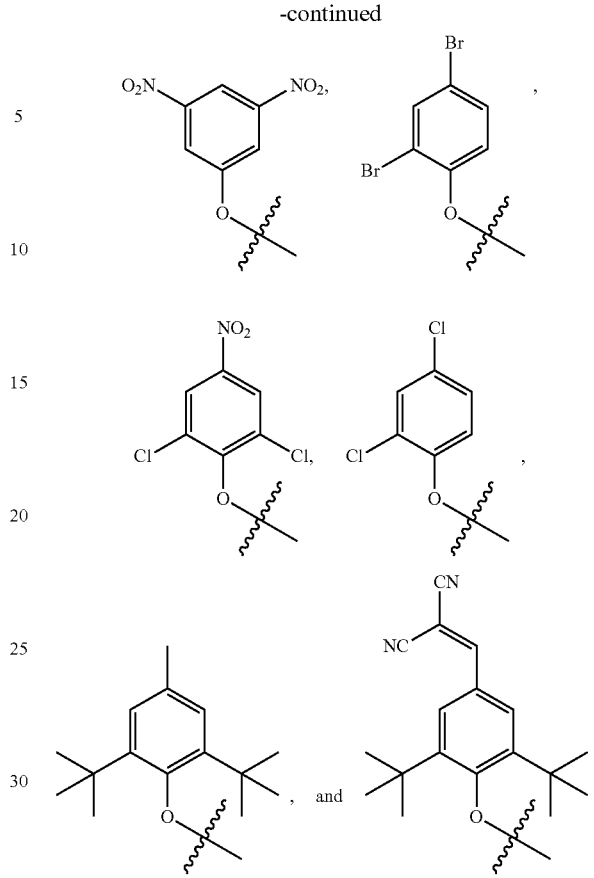

and ring A is imidazole, substituted with 2 substituents independently selected from —NO$_2$ or methyl; or ring A is imidazole, substituted with one —NO$_2$ and one methyl; or ring A is selected from the group consisting of 1-imidazolyl, 5-imidazolyl, and 2-imidazolyl; or ring A is selected from the group consisting of 1-imidazolyl and 5-imidazolyl; or ring A is 1-imidazolyl; or ring A is 5-imidazolyl; or ring A is 2-imidazolyl; or ring A is

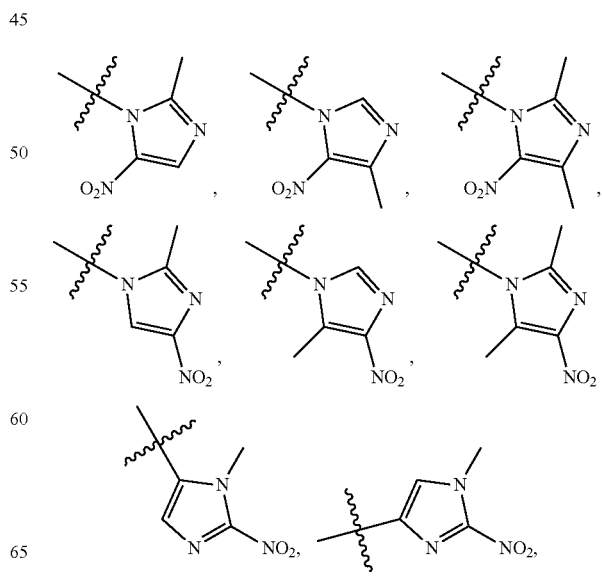

-continued

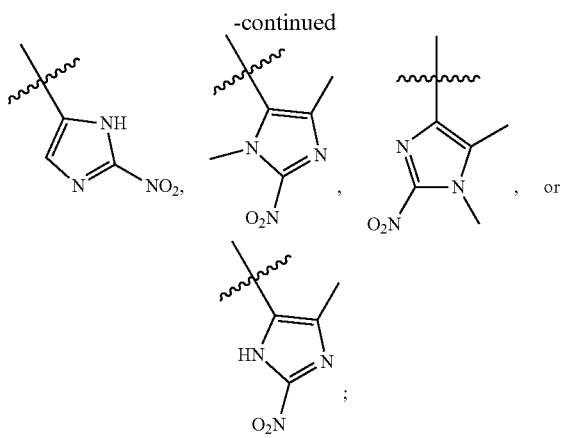

or ring A is selected from

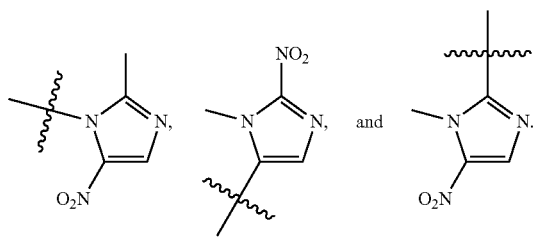

In some embodiments, y is 1. In some embodiments, y is 2. In some embodiments, y is 3.

In some embodiments, x is an integer from 1 to 3. In a further embodiment, x is 1. In another further embodiment, x is 2.

In some embodiments, the novel compounds of the present disclosure may be represented by Formula IIa:

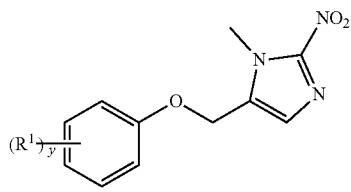

Formula IIa or a pharmaceutically acceptable salt thereof, wherein $R^1$ and y are defined above.

In some embodiments of Formula IIa, y is 1 and $R^1$ is $NO_2$. In another embodiment, y is 2 and each $R^1$ is independently $NO_2$ or halo. In a further embodiment, y is 2 and each $R^1$ is independently $NO_2$, Cl, or Br. In another embodiment, y is 3 and each $R^1$ is independently $NO_2$ or Cl. In another embodiment, y is 3 and each $R^1$ is independently methyl or tert-butyl. In another embodiment, y is 3 and each $R^1$ is independently tert-butyl or

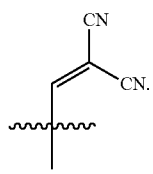 [SMILES: *C=C(C#N)C#N]

In some embodiments, the novel compounds of the present disclosure may be represented by Formula IIb:

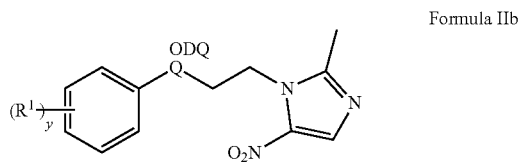

Formula IIb or a pharmaceutically acceptable salt thereof, wherein $R^1$ and y are defined above.

In some embodiments of Formula IIb, y is 1 and each $R^1$ is independently $NO_2$. In another embodiment, y is 2 and each $R^1$ is independently $NO_2$ or halo. In a further embodiment, y is 2 and each $R^1$ is independently $NO_2$ or Cl. In another embodiment, y is 3 and each $R^1$ is independently $NO_2$ or Cl.

In one embodiment, the novel compound of the present disclosure is selected from the compounds listed in Table A below.

TABLE A

| Compound # | Structure Name | Structure |
| --- | --- | --- |
| 1 | 1-[2-(2,4-Dinitro-phenoxy)-ethyl]-2-methyl-5-nitro-1H-imidazole | |
| 2 (Compound A) | 5-(2,5-Dinitro-phenoxymethyl)-1-methyl-2-nitro-1H-imidazole | |
| 3 | 1-Methyl-2-nitro-5-(4-nitro-phenoxymethyl)-1H-imidazole | |
| 4 | 1-Methyl-2-nitro-5-(3-nitro-phenoxymethyl)-1H-imidazole | |
| 5 | 5-(3,5-Dinitro-phenoxymethyl)-1-methyl-2-nitro-1H-imidazole | |
| 6 | 5-(2,4-Dichloro-phenoxymethyl)-1-methyl-2-nitro-1H-imidazoleimidazole | |
| 7 | 5-((2,4-dibromophenoxy)methyl)-1-methyl-2-nitro-1H-imidazole | |

TABLE A-continued

| Compound # | Structure Name | Structure |
|---|---|---|
| 8 | 5-(2,6-Dichloro-4-nitro-phenoxymethyl)-1-methyl-2-nitro-1H-imidazole | 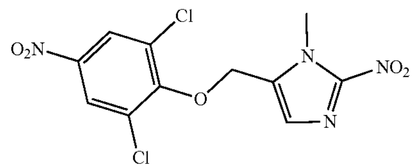 [SMILES: Cn1c(COc2c(Cl)cc([N+](=O)[O-])cc2Cl)cnc1[N+](=O)[O-]] |
| 9 | 2-(3,5-di-tert-butyl-4-((1-methyl-2-nitro-1H-imidazol-5-yl)methoxy)benzylidene)malononitrile | 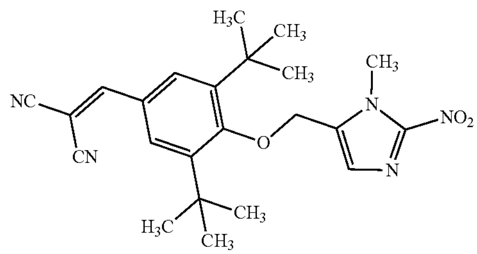 [SMILES: Cn1c(COc2c(C(C)(C)C)cc(C=C(C#N)C#N)cc2C(C)(C)C)cnc1[N+](=O)[O-]] |
| 10 | 5-((2,6-di-tert-butyl-4-methylphenoxy)methyl)-1-methyl-2-nitro-1H-imidazole | 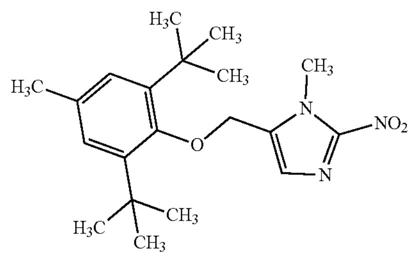 [SMILES: Cc1cc(C(C)(C)C)c(OCc2cnc([N+](=O)[O-])n2C)c(C(C)(C)C)c1] |
| 11 | 2-Methyl-5-nitro-1-(4-nitro-phenoxymethyl)-1H-imidazole | 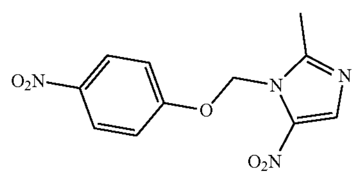 [SMILES: Cc1ncc([N+](=O)[O-])n1COc1ccc([N+](=O)[O-])cc1] |
| 12 | 2-Methyl-5-nitro-1-(3-nitro-phenoxymethyl)-1H-imidazole | 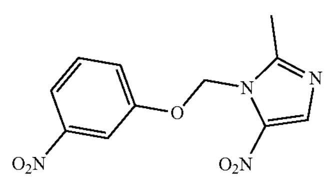 [SMILES: Cc1ncc([N+](=O)[O-])n1COc1cccc([N+](=O)[O-])c1] |
| 13 | 1-(3,5-Dinitro-phenoxymethyl)-2-methyl-5-nitro-1H-imidazole | 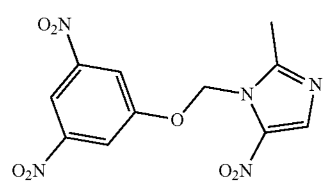 [SMILES: Cc1ncc([N+](=O)[O-])n1COc1cc([N+](=O)[O-])cc([N+](=O)[O-])c1] |
| 14 | 1-(2,4-Dichloro-phenoxymethyl)-2-methyl-5-nitro-1H-imidazole | 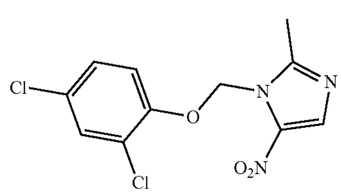 [SMILES: Cc1ncc([N+](=O)[O-])n1COc1ccc(Cl)cc1Cl] |
| 15 | 1-(2,6-Dichloro-4-nitro-phenoxymethyl)-2-methyl-5-nitro-1H-imidazole | 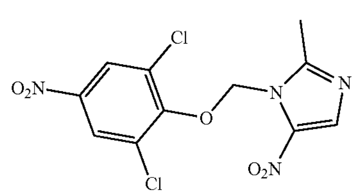 [SMILES: Cc1ncc([N+](=O)[O-])n1COc1c(Cl)cc([N+](=O)[O-])cc1Cl] |

TABLE A-continued

| Compound # | Structure Name | Structure |
|---|---|---|
| 16 | 2((2,4-dinitrophenoxy)methyl)-1-methyl-5-nitro-1H-imidazole | 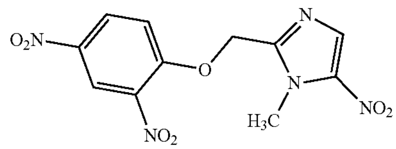 [SMILES: Cn1c([N+](=O)[O-])cnc1COc1ccc([N+](=O)[O-])cc1[N+](=O)[O-]] |
| 17 | 2-[2-(2,4-Dinitro-phenoxy)-ethyl]-1-methyl-5-nitro-1H-imidazole | |
| 18 | 1-Methyl-5-nitro-2-(4-nitro-phenoxymethyl)-1H-imidazole | |
| 19 | 1-Methyl-5-nitro-2-(3-nitro-phenoxymethyl)-1H-imidazole | |
| 20 | 2-(3,5-Dinitro-phenoxymethyl)-1-ethyl-5-nitro-1H-imidazole | |
| 21 | 2-(2,4-Dichloro-phenoxymethyl)-1-methyl-5-nitro-1H-imidazole | |
| 22 | 2-(2,6-Dichloro-4-nitro-phenoxymethyl)-1-methyl-5-nitro-1H-imidazole | |

In one embodiment, the present disclosure provides a novel compound, 5-[(2,4-dinitrophenoxy)methyl]-1-methyl-2-nitro-1H-imidazole or a pharmaceutically acceptable salt thereof.

In another embodiment, the novel compound of the present disclosure is useful for treating mitochondria-related disorders, including, but not limited to, obesity, diabetes, insulin resistance, and heart or renal failure in a mammal in need thereof.

In another embodiment, the novel compound of the present disclosure is useful for treating disease, disorders, and conditions which are associated with defects in mitochondrial function in a mammal in need thereof.

In another embodiment, the novel compound of the present disclosure can stimulate oxygen consumption rate (OCR) in a mammal in need thereof.

In another embodiment, the novel compound of the present disclosure is useful for treating diabetes, including but not limiting, non-alcoholic fatty liver disease (NAFLD), non-alcoholic steatohepatitis (NASH), hepatic steatosis, and type 2 diabetes (T2DM) in a mammal in need thereof.

In another embodiment, the novel compound of the present disclosure is useful for treating lipdystrophy (acquired or inherited) in a mammal in need thereof.

In another embodiment, the novel compound of the present disclosure is useful for treating hypertriglyceridemia in a mammal in need thereof.

In another embodiment, the novel compound of the present disclosure is useful for treating metabolic diseases or disorders in a mammal in need thereof.

In another embodiment, the novel compound of the present disclosure is useful for treating obesity or reducing adiposity in a mammal in need thereof.

In another embodiment, the novel compound of the present disclosure is useful for controlling or preventing from weight gain or maintaining of a weight in a mammal in need thereof.

In another embodiment, the novel compound of the present disclosure is useful for controlling or preventing obesity or excess body fat in a mammal in need thereof.

In another embodiment, the novel compound of the present disclosure is useful for treating dyslipidemia in a mammal in need thereof.

In another embodiment, the novel compound of the present disclosure is useful for treating cardiovascular disease in a mammal in need thereof.

In another embodiment, the novel compound of the present disclosure is useful for treating heart disease in a mammal in need thereof.

In another embodiment, the novel compound of the present disclosure is useful for treating cardiovascular disease in a mammal in need thereof.

In another embodiment, the novel compound of the present disclosure is useful for treating atherosclerosis in a mammal in need thereof.

In another embodiment, the novel compound of the present disclosure is useful for controlling or preventing ischemic reperfusion injury in a mammal in need thereof.

In another embodiment, the novel compound of the present disclosure is useful for treating inflammation and fibrosis resulting in NASH.

In another embodiment, the present disclosure provides pharmaceutical compositions comprising a pharmaceutically acceptable carrier and the novel compound of the present disclosure.

Routes of Administration

In therapeutic use for controlling or preventing weight gain in a mammal, a compound of the present disclosure or its pharmaceutical compositions can be administered orally, or parenterally.

In certain embodiments, the compound of the present disclosure or its pharmaceutical compositions can be administered once daily orally.

Pharmaceutical Salts

The compound of formula I may be used in its native form or as a salt. In cases where forming a stable nontoxic acid or base salt is desired, administration of the compound as a pharmaceutically acceptable salt may be appropriate.

Suitable pharmaceutically acceptable salts include prepared from inorganic and organic acids including sulfate, hydrogen sulfate, hydrochloric, hydrobromic, hydriodic, nitric, carbonic, sulfuric, phosphoric acids, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxy benzoic, phenylacetic, mandelic, embonic (pamoic), methanesulfonic, ethanesulfonic, benzenesulfonic, pantothenic, trifluoromethanesulfonic, sulfanilic, stearic, alginic, 2-hydroxyethanesulfonic, p-toluene sulfonic, cyclohexylaminosulfonic, salicylic, galactaric, β-hydroxybutyric and galacturonic acid; or prepared from ammonium salts and metallic salts including calcium, magnesium, potassium, sodium and zinc salts.

Composition/Formulation

Pharmaceutical compositions of the present disclosure may be manufactured by processes well known in the art, e.g., by means of conventional mixing, dissolving, granulation, dragee-making, levitating, emulsifying, encapsulating, entrapping, lyophilizing processes or spray drying.

Pharmaceutical compositions for use in accordance with the present disclosure may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant disclosure. Such excipients and carriers are described, for example, in "Remington's Pharmaceutical Sciences" Mack Pub. Co., New Jersey (1991).

Dosage

Pharmaceutical compositions suitable for use in the present disclosure include compositions wherein the active ingredients are contained in an amount sufficient to achieve the intended purpose, i.e., control or the prevention of weight gain, or the maintenance of.

The quantity of active component, which is the novel compound of the present disclosure, in the pharmaceutical composition and unit dosage form thereof, may be varied or adjusted depending upon the potency of the particular compound and the desired concentration. Determination of a therapeutically effective amount is well within the capability of those skilled in the art. Generally, the quantity of active component will range between 0.01% and 99.9% by weight of the composition.

Generally, a therapeutically effective amount of dosage of active component may be in the range of about 0.001 to about 1000 mg/kg of body weight/day. The desired dose may conveniently be presented in a single dose or as divided doses administered at appropriate intervals, for example, as two, three, four or more sub-doses per day.

In some embodiments, the effective amount of the novel compound of the present disclosure is greater than about 0.01 mg/kg. In other embodiments, the effective amount of the novel compound is between about 0.01 mg/kg to about 1000 mg/kg and any and all whole or partial increments there between, including about 0.1 mg/kg, about 1 mg/kg, about 0.01 mg/kg, about 0.1 mg/kg, about 1 mg/kg, about 10 mg/kg, and about 100 mg/kg.

In some embodiments, the effective amount of the novel compound is about 100-50 mg/kg. In some embodiments, the effective amount of the novel compound is about 50-10 mg/kg. In other embodiments, the effective amount of the novel compound is about 10-5 mg/kg. In other embodiments, the effective amount of the novel compound is about 5-2.5 mg/kg.

EXAMPLES

Definitions
ALT=alanine aminotransaminase.
AST=aspartate transaminase.
ALP=Alkaline Phosphatase.
ALB=Albumin.

General Synthetic Scheme

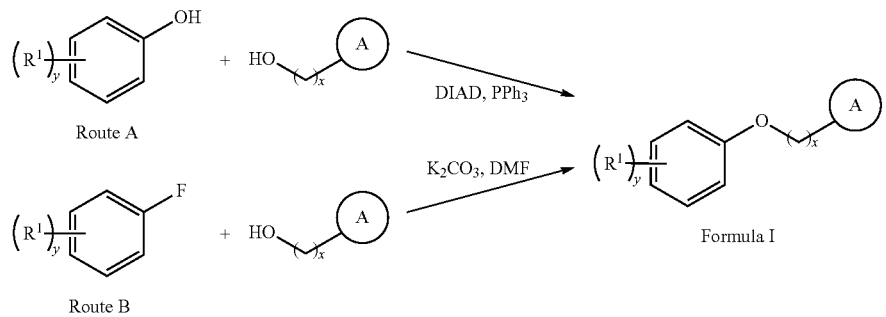

The compounds of Formula I can be produced by synthetic procedures known to those having skill in the art. Two such methods are provided in Scheme 1, wherein the variables ring A, $R^1$, x, and y are defined above, and are not intended to be limiting in any way. Indeed, there may be many more plausible routes to synthesize the compounds of the invention.

As provided in Route A, Mitsunobu chemistry can be used to activate the hydroxyl oxygen of the imidazole compound using a reagent combination such as diisopropyl azodicarboxylate (DIAD) or diethyl azodicarboxylate (DEAD) with triphenylphosphine, which gives way to nucleophilic substitution of the activated hydroxyl with phenol.

Compounds of Formula I can also be produced by the nucleophilic aromatic substitution strategy of Route B. Here, a fluorophenyl compound is reacted with the imidazole compound under moderately basic conditions, such as potassium carbonate in dimethylformamide. Substitution of the fluoride by the hydroxyl group of the imidazole compound provides the ether linkage of the compound of Formula I.

Example 1

Plasma Concentration of DNP and Compound A after DNP or Compound A Administration Materials and Methods: 5-7 week old male C57BL/6 mice weighing 18-20 g was obtained from Beijing Vital River Co., LTD. The animals were quarantined in polycarbonate cages and in an environmentally monitored, well-ventilated room maintained at a temperature of (22±+3° C.) and a relative humidity of 40%-80% in laminar flow rooms with 3 animals in each cage for 7 days before and during the study. Fluorescent lighting provided illumination approximately 12 hours per day. The bedding material was corn cob, which was changed once per week. Each animal was assigned an identification number. The mice had access to irradiation sterilized dry granule food (Beijing Keaoxieli Feed Co., Ltd., Beijing, China) and sterile drinking water ad libitum during the entire study period.

Based on the body weight, animals were randomly assigned (n=4) to respective groups using a computer-generated randomization procedure. The following doses were administered by oral gavage in 7.1% DMSO in normal saline: Vehicle alone (7.1% DMSO in saline), 100 mg/kg DNP, and 1, 5, 10, 50, 100, 200, 300, 400, 500, 600, 1000, 1250, 1500 mg/kg Compound A. DNP was obtained from Sinopharm Chemical Reagent Beijing Co., Ltd. DMSO was obtained from Sigma Aldrich.

Plasma was collected by orbital puncture into 0.5 ml heparin coated centrifuge tubes after 0, 15 min, 30 min, 45 min, 1 h, 2 h, 3 h, 4 h, 6 h, 8 h, 12 h, 20 h and 24 h.

The samples were centrifuged for 5 min at 4000 rcf speed on a bench top centrifuge. The clear supernatant was transferred to a new tube and stored at −80° C. for PK analysis.

All statistical analysis was conducted, and the level of significance were set at $P<0.05$. The group means and standard errors were calculated for all measurement parameters as study designed. One way ANOVA comparisons among the groups were performed with software SPSS 17.0.

Figure 2:
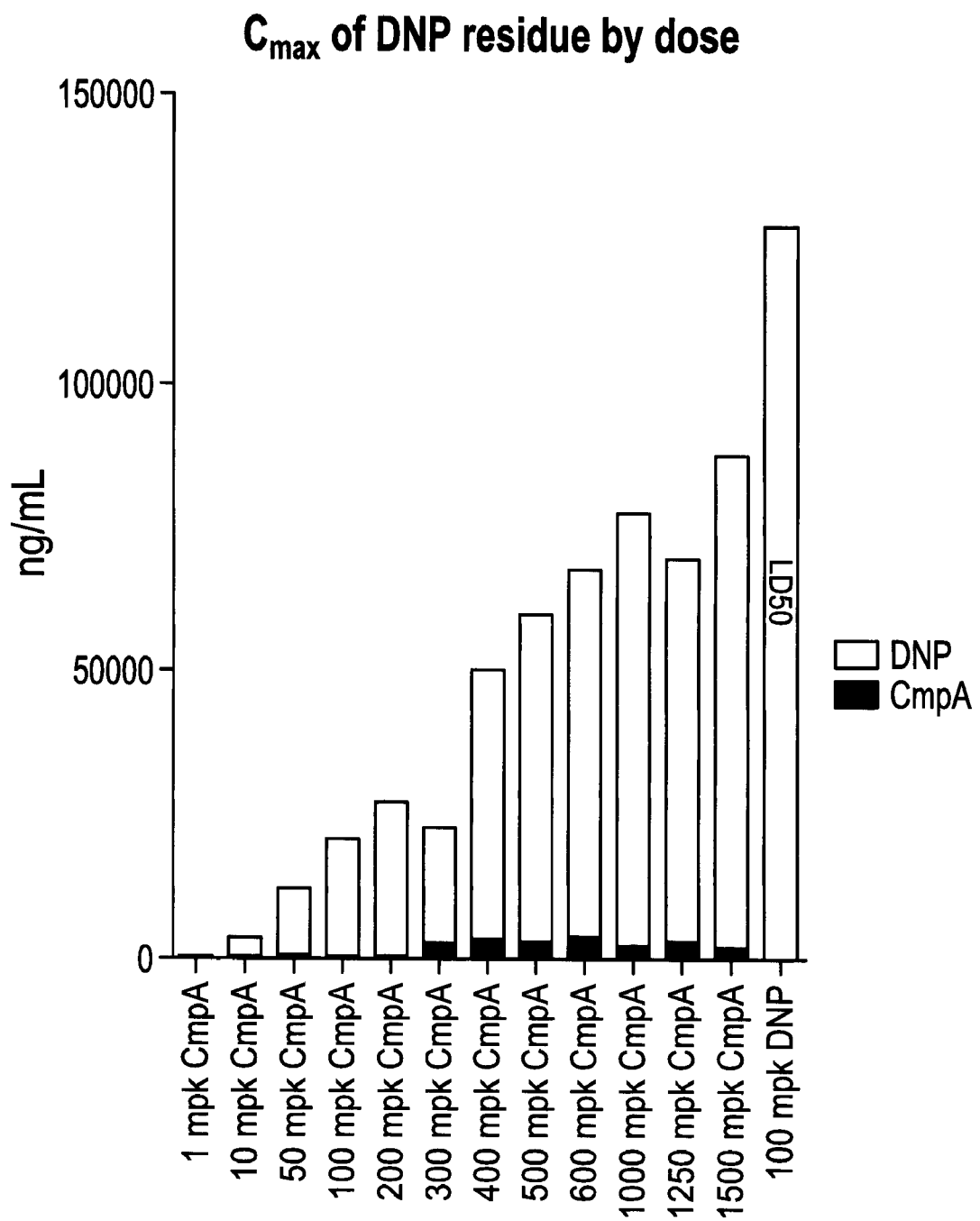
FIG. 2 illustrates administering Compound A to the mice. The maximal plasma concentration (Cmax) of DNP residue is sharply reduced compared to administering DNP directly, and toxicity sharply reduced.
Figure 3:
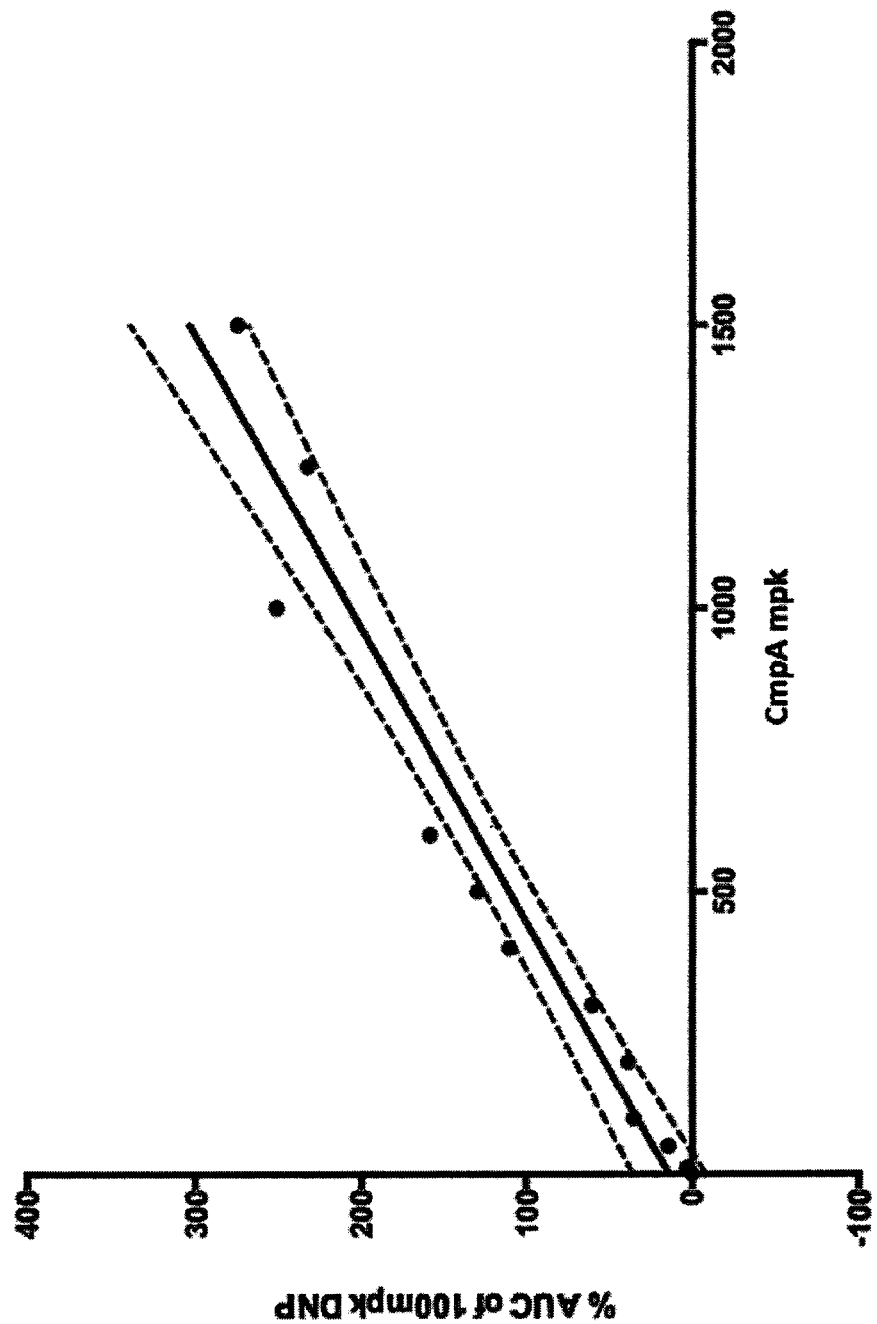
FIG. 3 illustrates that DNP total exposure increases in a linear fashion up to at least 1500 mpk Compound A. The total exposure of DNP after administering 100 mpk DNP was set to 100% in this graph. Each data point is represented as a black dot. The straight linearity (Y=0.1932*x+13.94) is graphed as a solid black line, and the 95% confidence interval is graphed as dotted lines. $R^2$=0.9770. The Exposure in the graph is expressed as a percentage of total DNP exposure, where the exposure after dosing with 100 mpk DNP was set as 100%.
Figure 4:
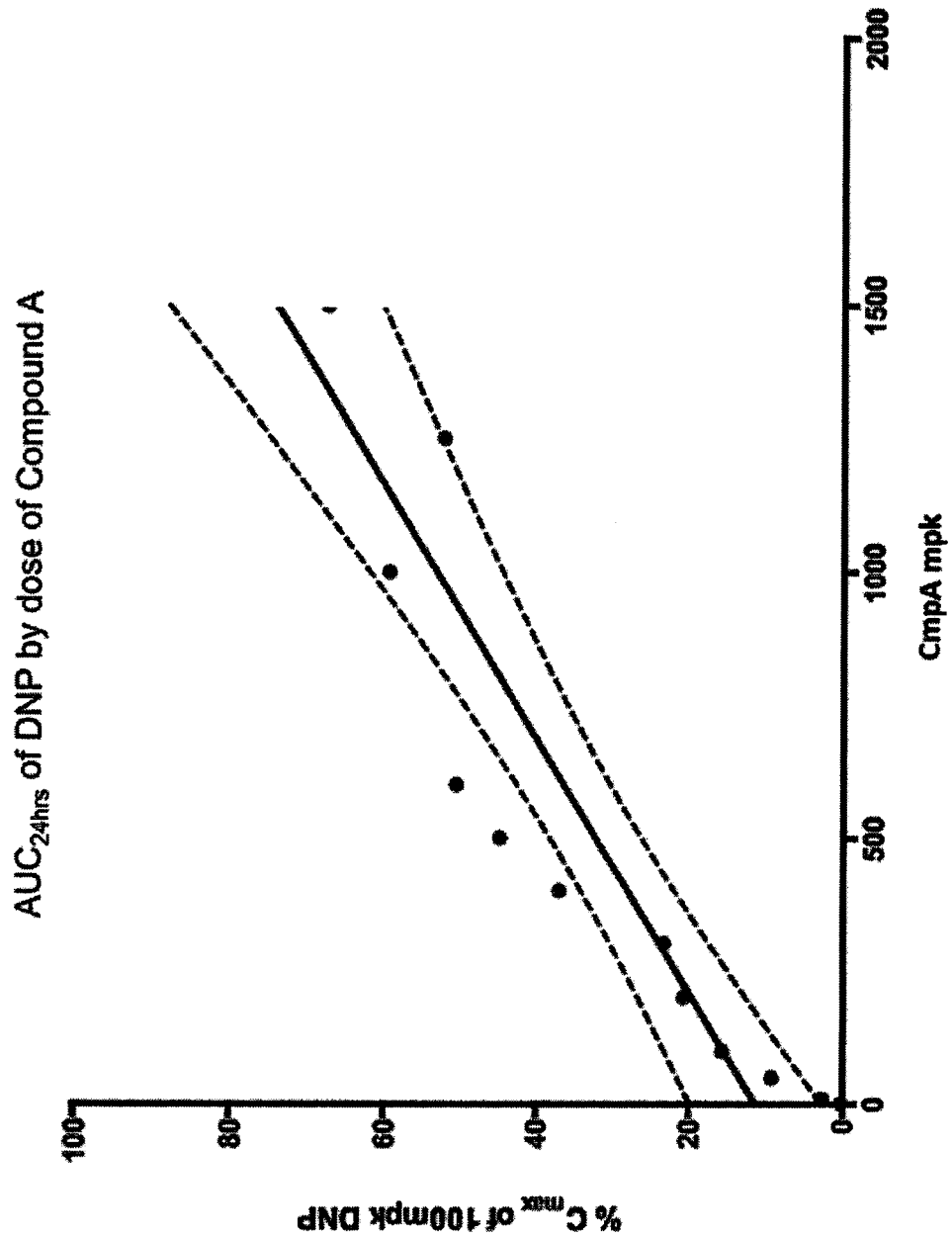
FIG. 4 illustrates that the maximal plasma concentration of DNP in mice that receive Compound A is linearly increased by dose, but does not reach the same levels that is observed when administering the LD50 dose of DNP. The maximal concentration of DNP after administering 100 mpk DNP was set to 100% in this graph. Each data point is represented as a black dot. The straight linearity (Y=0/04178*x+11.34) is graphed as a solid black line, and the 95% confidence interval is graphed as dotted lines. $R^2$=0.9770.

Results: Two (50%) of the animals administered 100 mg/kg DNP died within the first two hours after administration and one of the animals in 1500 mg/kg Compound A was found dead after 12 hours. No other abnormal clinical symptoms were observed during the entire experiment. PK analysis shows that Compound A was hydrolyzed to DNP residue, and Compound A was detected in plasma only in small amounts in the highest dosed animals. FIG. 1 and FIG. 2 show that in the animals that were administered Compound A, the maximal plasma concentration (Cmax) of DNP residue was sharply reduced compared to administering DNP directly. None of the groups that received Compound A reached the same Cmax as the group that received DNP. Tmax was delayed in animals given Compound A. At the same time, significantly higher total exposure of DNP residue was measured in animals given Compound A compared to DNP. In summary, Compound A is a safer drug than DNP due to decreased Cmax. Both total exposure and Cmax of DNP residue increase by dose of Compound A in a linear fashion.

Example 2

Plasma Concentration of ALT, AST and ALP Liver Enzymes after Administering Compound A to Mice with Induced Fatty Liver Disease Male C57BL/6 mice were obtained from Beijing Vital River Co., LTD. The animals were quarantined in polycarbonate cages and in an environmentally monitored, well-ventilated room maintained at a temperature of (22±3° C.) and a relative humidity of 40%-80% in laminar flow rooms with 3 animals in each cage for 7 days before and during the study. Fluorescent lighting provided illumination approximately 12 hours per day. The mice had access to irradiation sterilized dry granule food (Beijing Keaoxieli Feed Co., Ltd., Beijing, China) and sterile drinking water ad libitum during the first week.

After acclimatizing, and throughout the study period, the food was exchanged for methionine/choline-deficient chow (MCD) to induce nonalcoholic Fatty Liver Disease (NAFLD) in the animals. After four weeks on MCD, the animals were divided into four groups (n=8) and administered 0 mpk, 5 mpk, 25 mpk or 100 mpk Compound A by oral gavage in 7.1% DMSO in normal saline.

The blood was collected into a tube with no anticoagulant, the serum samples were immediately processed by centrifugation at 4° C., 6000 g for 15 minutes, and were then transferred into a new test tube. Samples were analyzed for three liver enzymes: ALT; AST; and ALP by using a TOSHIBA TBA-40FR automated biochemical analyzer.

Figure 5:
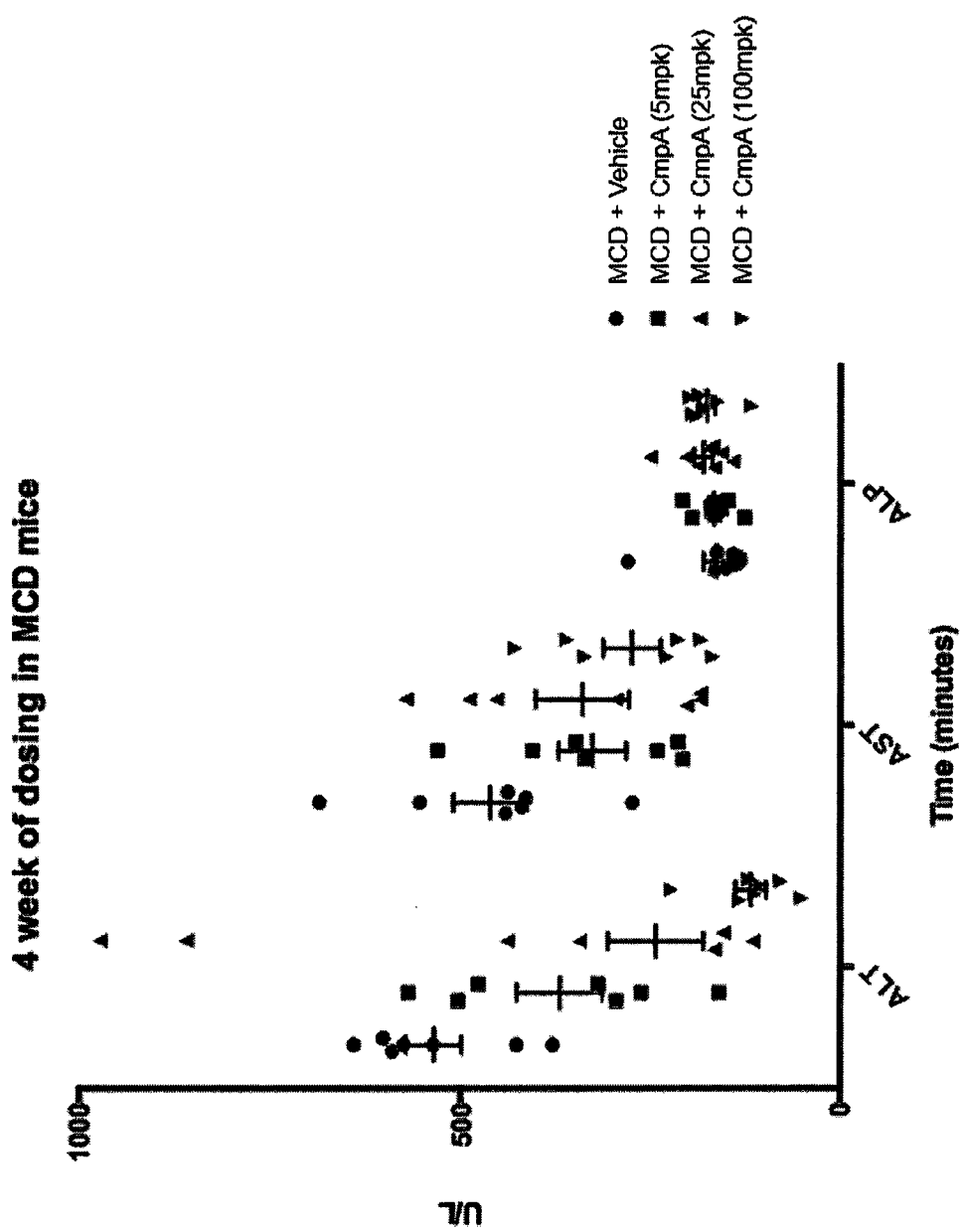
FIG. 5 illustrates the plasma concentration of ALT, AST and ALP liver enzymes in the mice with induced fatty liver disease after 4 weeks of administering with Compound A.

Results: As seen in FIG. 5, ALT and AST levels are sharply increased in MCD treated mice. These levels are reduced in a dose-dependent manner with Compound A. Statistical significant decreases were observed at 5 mpk and 100 mpk, whereas statistical significance is only reached in the 25 mpk dose level group once the two statistical outliers are excluded from the analysis.

Example 3

Oral Glucose Tolerance Test after Compound a Administration to Mice with Induced Fatty Liver Disease Mice were treated as described in Example 2. Oral Glucose Tolerance Test (OGTT) was performed on all study animals after five weeks of Compound A treatment. The baseline (time 0) glucose level was measured after 16 hours fasting. Following oral administration of 2 g/kg glucose, the blood glucose levels were measured at 30, 60 and 120 minutes using Accu-Chek Performa System.

Figure 6:
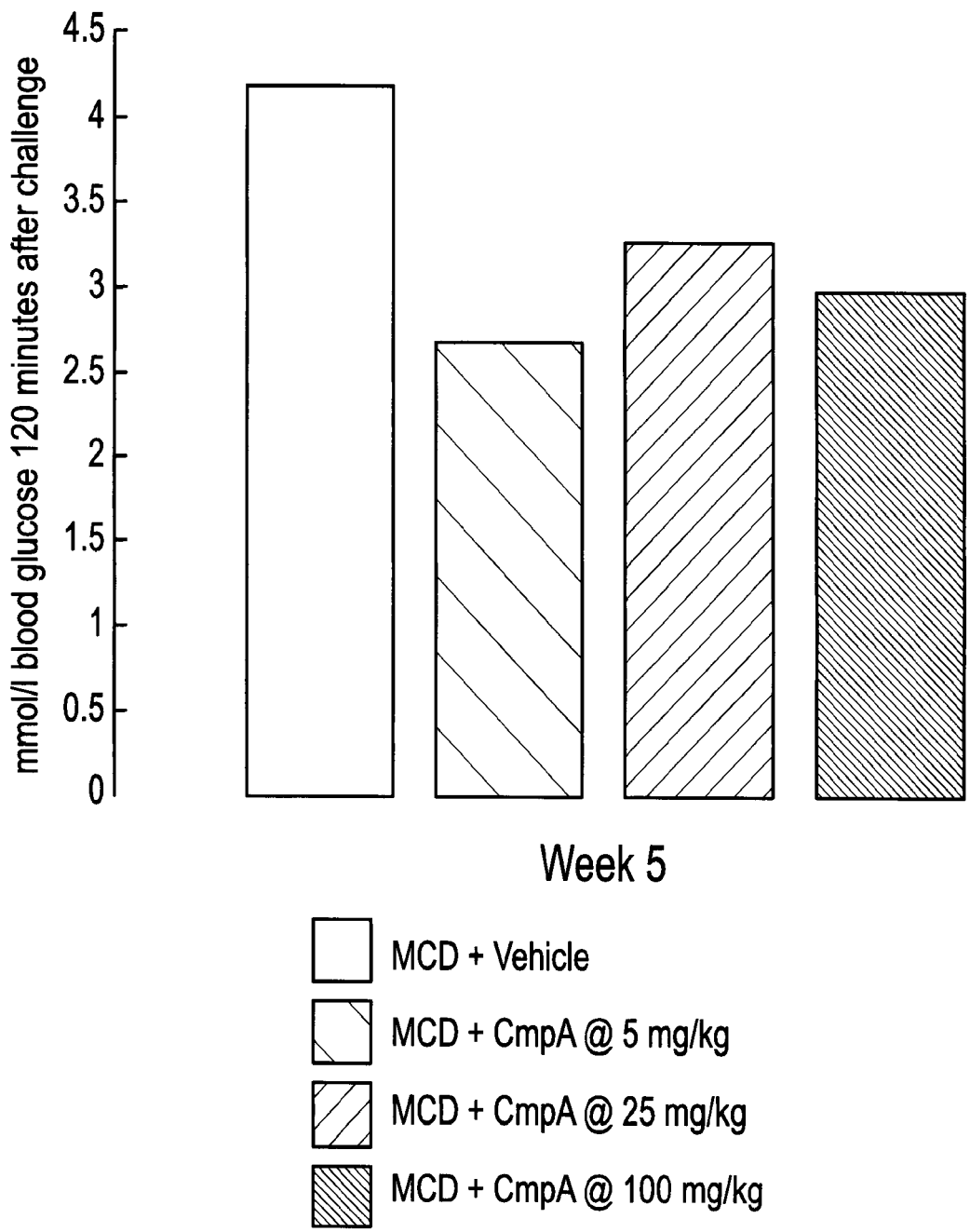
FIG. 6 illustrates the blood glucose in Compound A treated animals compared to their untreated counterparts 120 minutes after the glucose challenge in all three treatment groups ($p<0.05$ for 25 mg/kg and 100 mg/kg treatments, $p<0.01$ for 5 mg/kg treatment). The differences between vehicle and treated are all statistically significant ($p<0.05$). This oral glucose tolerance test was performed after five weeks of Compound A treatment.

Results. Blood glucose levels were significantly lower 120 minutes after the glucose test in all three treatment groups ($p<0.05$ for 25 mg/kg and 100 mg/kg treatments, $p<0.01$ for 5 mg/kg treatment). See FIG. 6.

Example 4

Evaluation of the Effect of Compound A in MCD Diet Induced NASH Mouse Model

Figure 7:
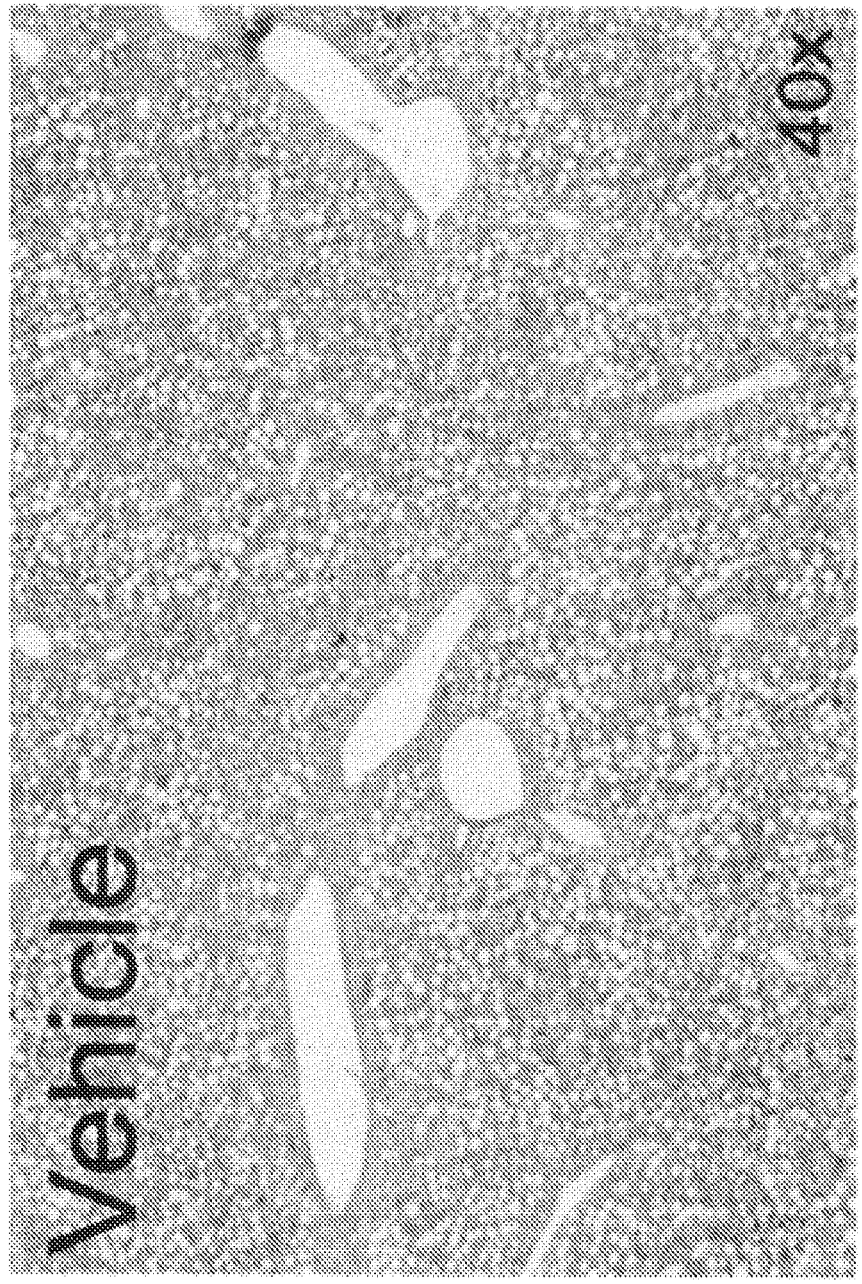
FIG. 7 illustrates lipid droplets in a control mouse liver in MCD diet-induced NASH fed mice.
Figure 8:
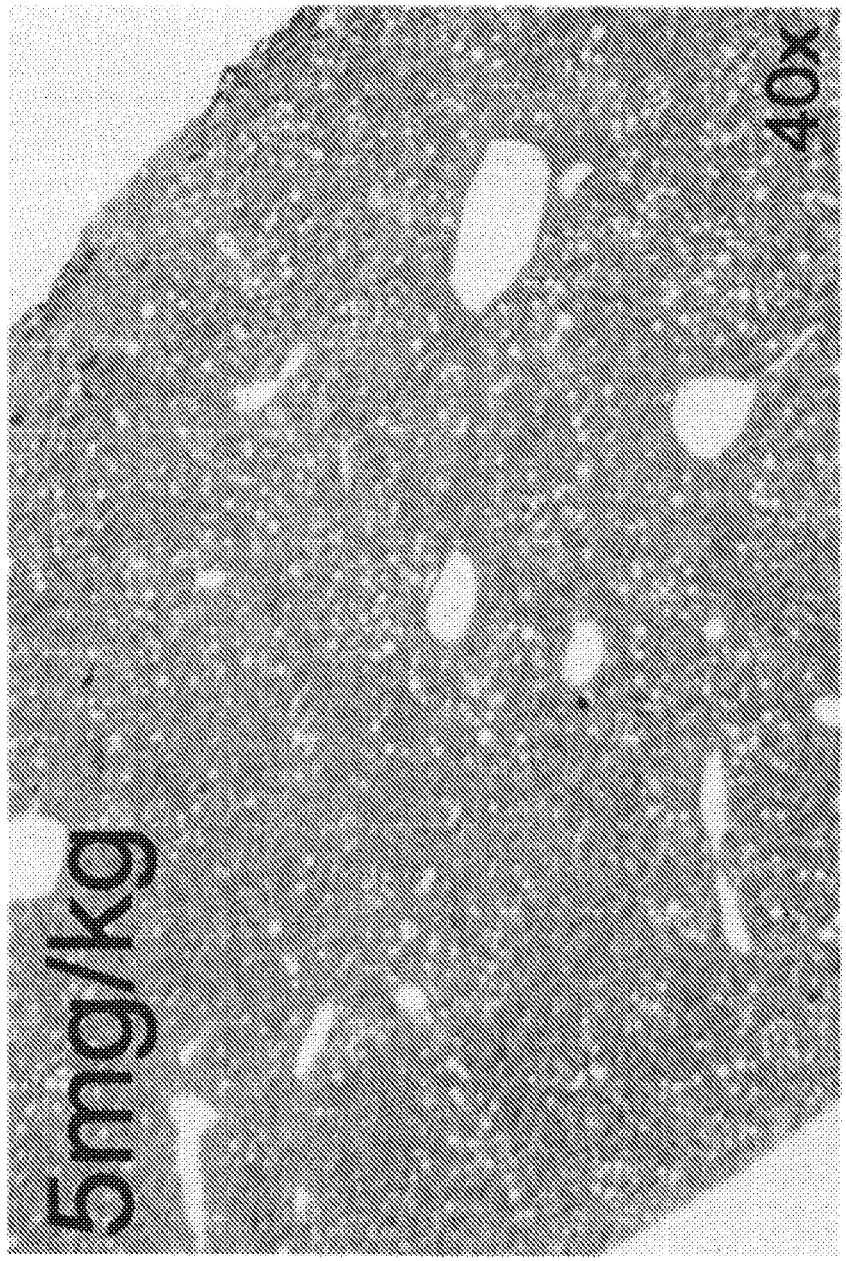
FIG. 8 illustrates mouse lipid droplets in mouse liver in MCD diet-induced NASH fed mice that were treated with 5 mpk Compound A.

We showed that Compound A reduces steatohepatitis and inflammatory cytokines in MCD diet-induced NASH mouse liver. The appearance of lipid droplets was reduced after 6 weeks of treatment. See FIGS. 7 and 8. These images indicate a sharply reduced amount of fat storage in the liver after treatment of 5 mpk Compound A. FIG. 7 shows lipid droplets in a control mouse liver in MCD diet-induced NASH fed mice. FIG. 8 shows mouse lipid droplets in mouse liver in MCD diet-induced NASH fed mice that were treated with 5 mpk Compound A. The treated mice had sharply reduced lipid droplets after 6 weeks of treatment.

Liver TNFα and IL-1β also decreased in the treated mice. See FIG. 9.

Example 5

Evaluation of the Effect of Compound A in Rat NAFLD Model Induced by HFD

In order to determine the effect of Compound A on rats fed a high fat diet (HFD) Compound A was administered by oral gavage once daily for 14 days. 50 SD rats at the age of 6 to 8 weeks old were supplied by Beijing Vital River Laboratory Animal Technology Co., Ltd. The animals were quarantined for at least 7 days before the study. The animals were kept in laminar flow rooms at constant temperature and humidity, sterile drinking water were available ad libitum, with one animal in each cage. Following the 7 days acclimation period, rats were fed a high fat diet (D12492, Research Diets) for a two weeks induction period. Following the induction period, the animals were randomly assigned into respective groups based on their body weight. The study groups and detail information of the treatment are shown in Table 1.

TABLE 1

Group and Treatments

| Group | Treatment | Dose level (mg/kg) | HFD | Route | Regimen | Number |
|---|---|---|---|---|---|---|
| 1 | Vehicle | — | Yes | PO | QD × 14 d | 10 |
| 2 | Compound A | 0.1 | Yes | PO | QD × 14 d | 10 |
| 3 | Compound A | 0.5 | Yes | PO | QD × 14 d | 10 |
| 4 | Compound A | 5 | Yes | PO | QD × 14 d | 10 |
| 5 | DNP | 1 | Yes | PO | QD × 14 d | 10 |

The animals were dosed 5 mL/kg PO Compound A, DNP or vehicle alone (7.5% DMSO in water) by oral gavage daily, for 14 days (From Day 15 to Day 28). Body weights of all animals were measured twice a week throughout the study. Food consumption was recorded for the animals in all groups twice a week throughout the study. Blood samples were collected by orbital puncture into a tube without anticoagulant on Day 15 (pre-treatment), Day 22 and Day 29. The blood samples were centrifuged at 6000 g for 15 minutes at 4° C., then serum samples were collected and transferred into another samples tube. The serum samples were kept at −80° C. if the analysis were not analyzed immediately. Lipid levels including triglycerides (TG), total cholesterol (TCHO), High density lipoprotein cholesterol (HDL-C), low density lipoprotein cholesterol (LDL-C) and free fatty acid (FFA) were measured at the end of study by using TOSHIBA TBA-40FR automated biochemical analyzer. Animals in all study groups were euthanized on Day 29, necropsy were performed.

The liver tissue samples were collected from all animals, and each liver samples were cut into 3 pieces, one piece was for liver lipid level analysis, one piece was for histology, and the last piece was snap frozen as a backup. At the end of the study, liver TG, TCHO, HDL-C, LDL-C and FFA level were analyzed using chemistry analyzer and liver ceramide levels were analyzed using LC-MS/MS method.

The results of this study showed that there were no significant changes or trends in glucose tolerance (as measured by an Oral Glucose Tolerance Test), body weight or food consumption were observed between study groups.

Figure 9:
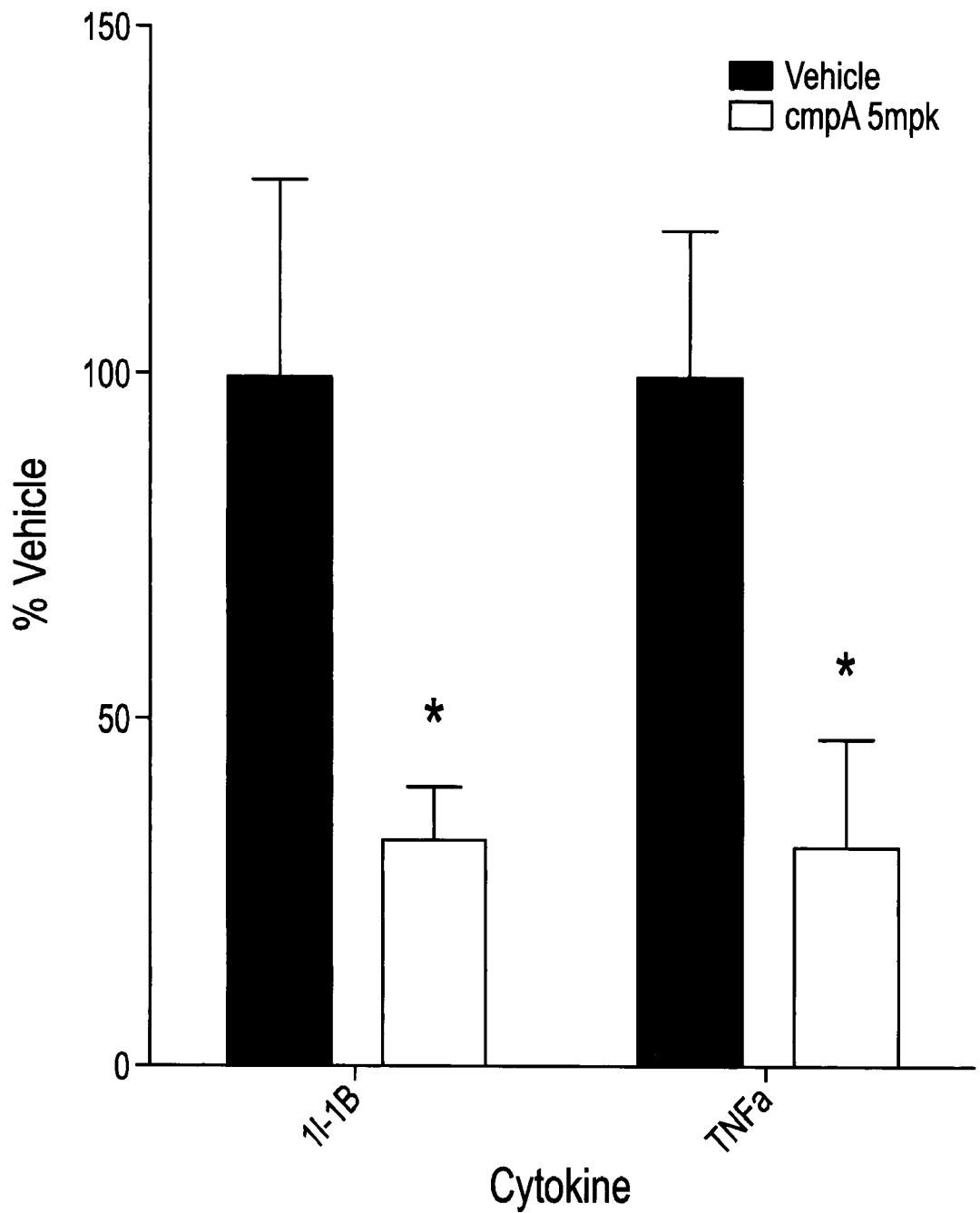
FIG. 9 illustrates liver TNFα and IL-1β decreased in mice fed a MCD diet-induced NASH feed that were treated with 5 mpk Compound A.

Serum FFA levels showed significant differences after seven days of dosing compared to vehicle although serum FFA and serum TG levels trended lower in a dose dependent manner compared to vehicle control (see FIGS. 8 and 9). FIG. 9 is statistically valid with p<0.05 (T-test), when compared with the vehicle group (Mean±SEM). The results indicate that Compound A may be used to reduce the risk for cardiovascular disease, NASH and NAFLD.

Figure 10:
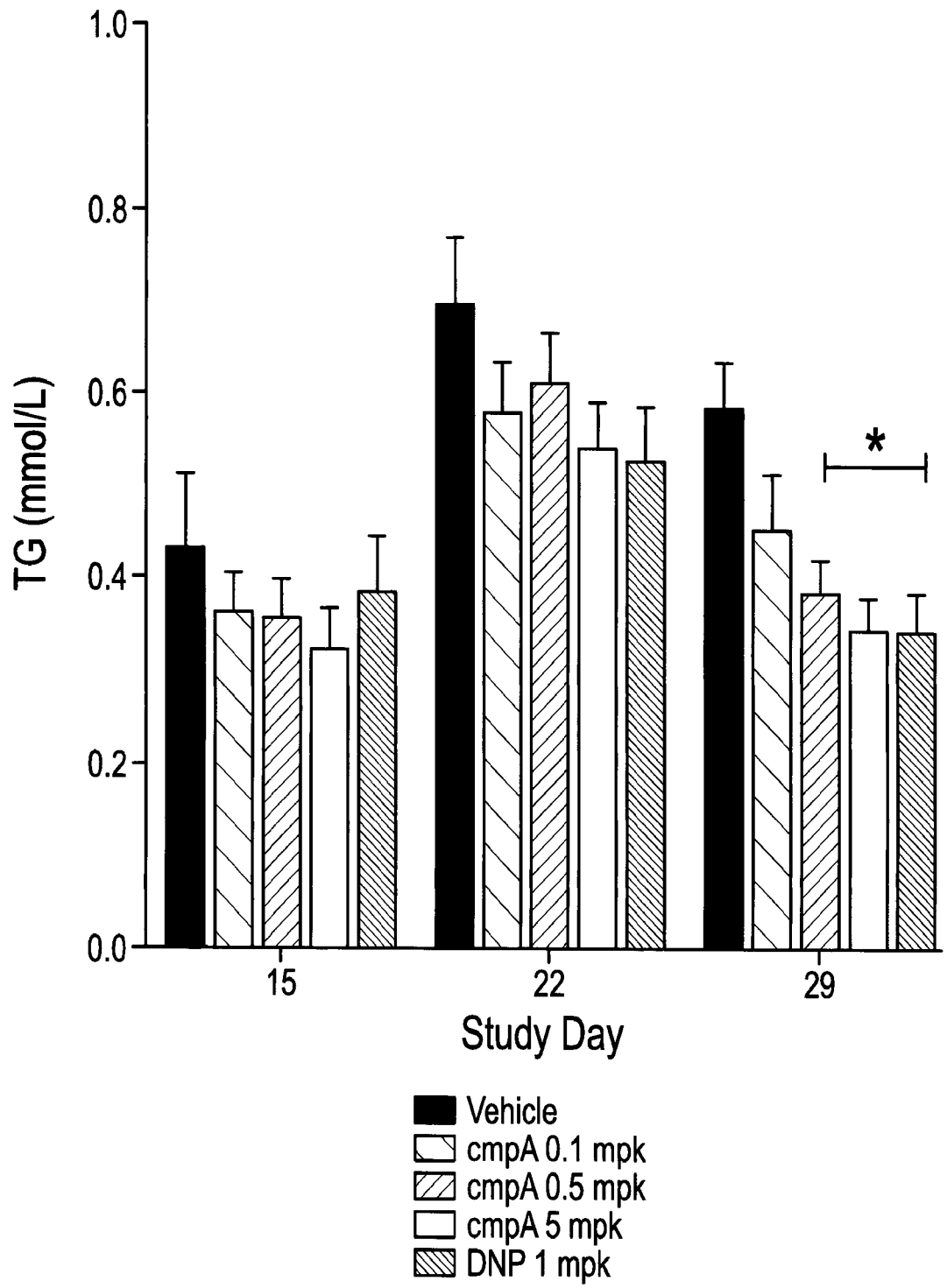
FIG. 10 illustrates serum TG Level of Study Groups from Example 5.
Figure 11:
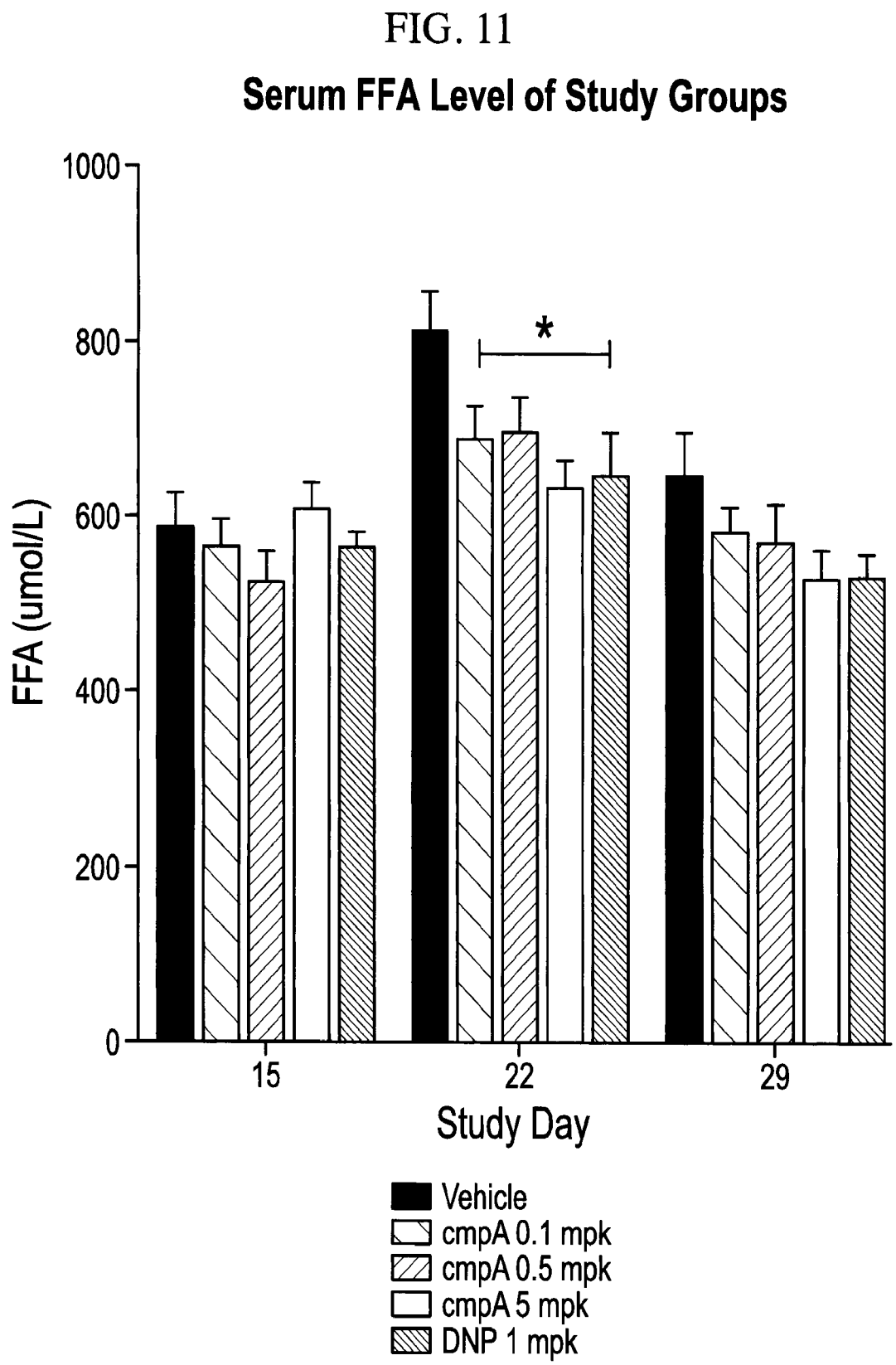
FIG. 11 illustrates serum FFA Level of Study Groups from Example 5.

FIG. 10 is a chart that shows serum TG Levels. In FIG. 10 the p<0.05 (ANOVA) (Mean±SEM). FIG. 11 is a chart that shows serum FFA Levels.

Notice that all liver lipid levels including TG, TCHO, HDL-C, LDL-C, FFA and ceramide trended lower at all treatment doses. A significant reduction in FFA was observed at the two highest doses of Compound A. The reduction of liver ceramide also reached significance in the highest dosed group.

Figure 12:
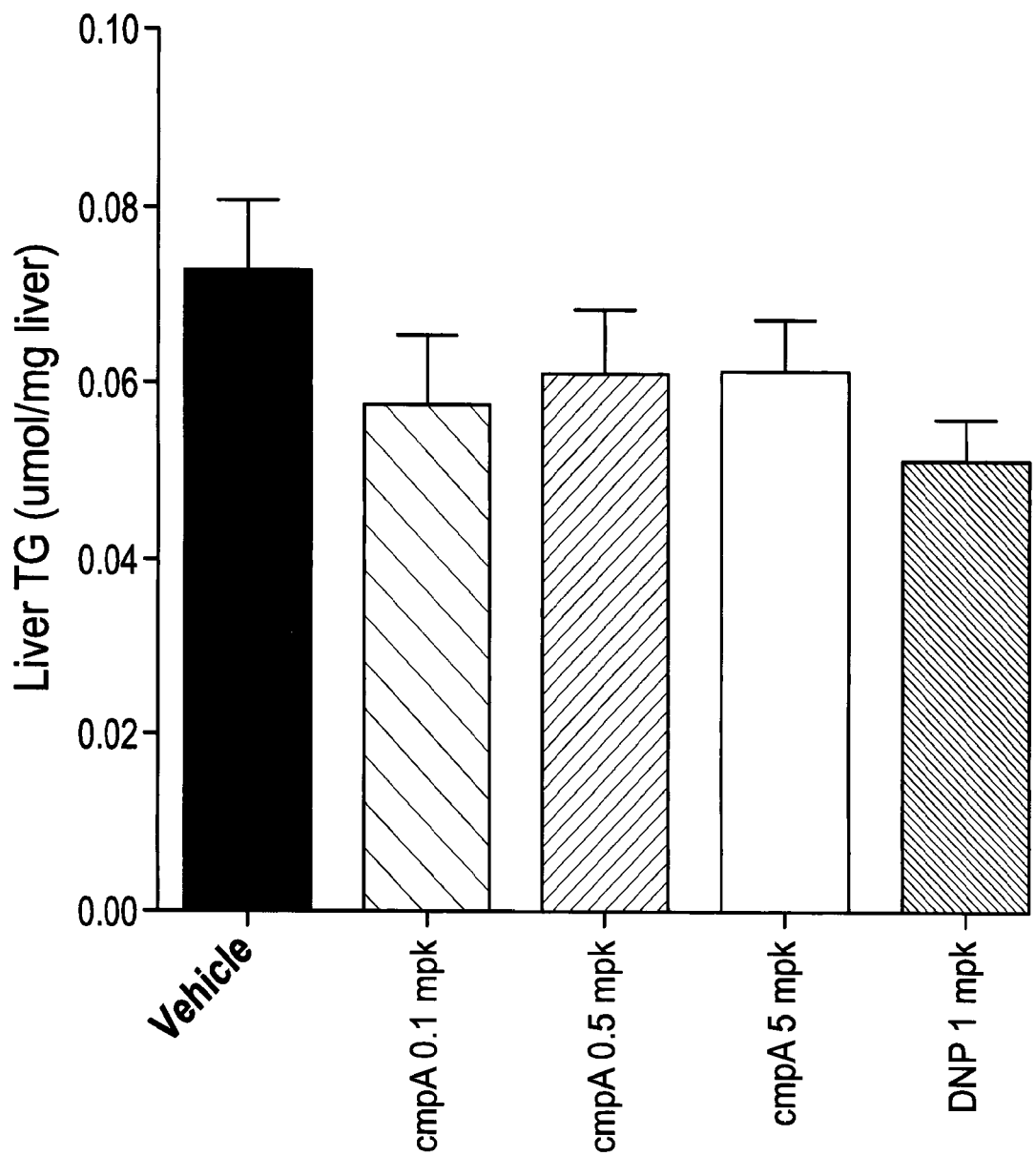
FIG. 12 illustrates liver TG Level of Study Groups from Example 5.
Figure 13:
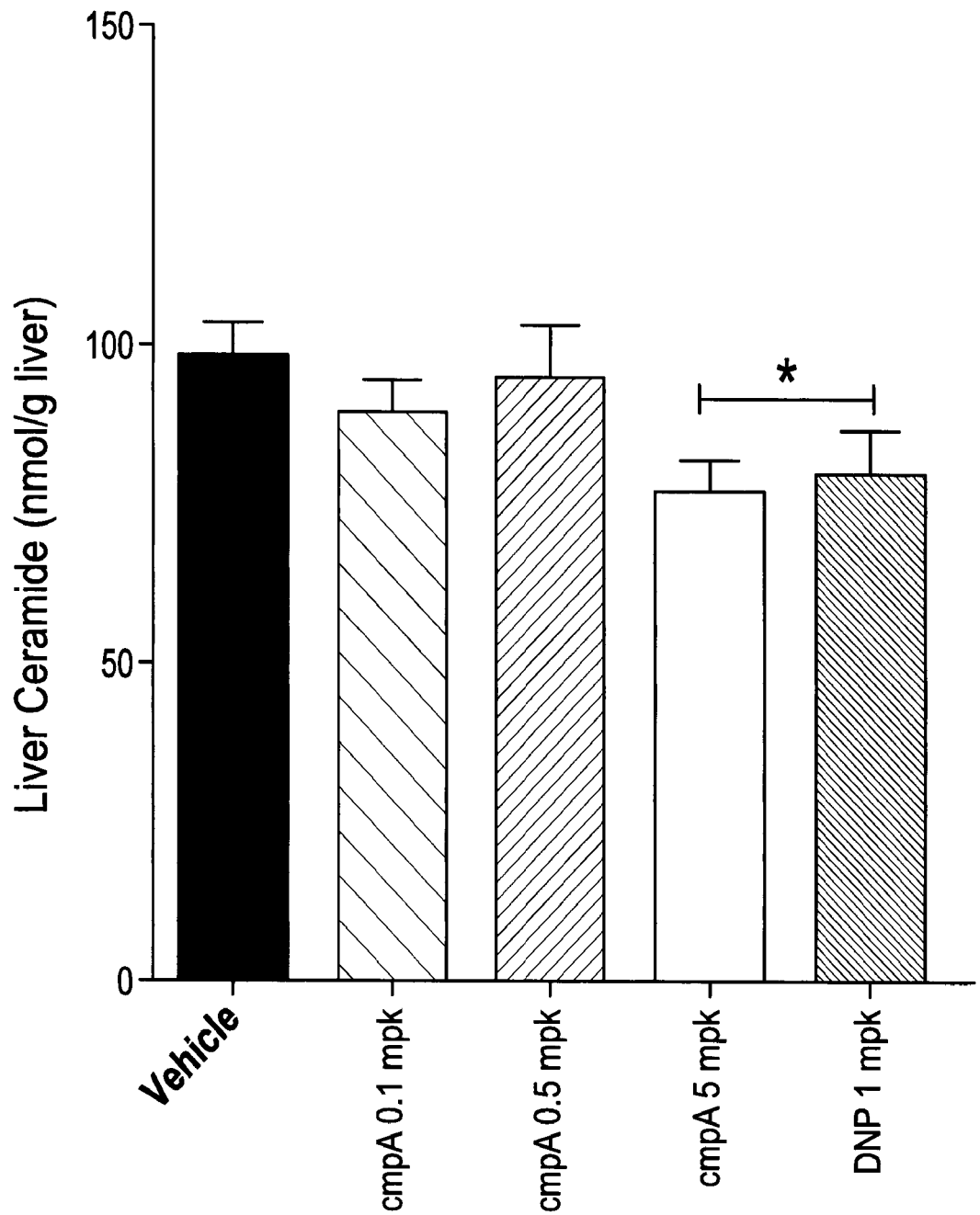
FIG. 13 illustrates liver Ceramide Level of Study Groups from Example 5.

FIG. 12 illustrates liver TG levels. FIG. 13 shows liver Ceramide Levels.

Example 6

Evaluation of the Effect of Compound A in Zucker Diabetic Fatty (ZDF) Rats

To determine the effect of Compound A administered by oral gavage once daily for 28 days in Zucker diabetic fatty (ZDF) rats 50 male rats were obtained from Beijing Vital River Laboratory Animal Technology Co. The animals were 8 weeks old at the start of induction and were quarantined for 7 days before the study. The rats were kept in laminar flow rooms at constant temperature and humidity with one animal in each cage and water was provided ad libitum during the quarantine and study periods.

Following the 7 days acclimation period, 50 ZDF rats were maintained on a special diet (Purina 5008 diet) for 4 weeks to induce Type 2 diabetes. Following 4 weeks of induction, the animals were randomly assigned to their respective groups based on their body weight and fasting glucose levels. The study groups and number of animals per group are shown in Table 2.

TABLE 2

Groups and Treatments

| Group | Treatment | Dose level (mg/kg) | Route | Regimen | Number |
|---|---|---|---|---|---|
| 1 | Vehicle | — | PO | QD × 28 d | 10 |
| 2 | DNP | 1 | PO | QD × 28 d | 10 |
| 3 | Compound A | 0.1 | PO | QD × 28 d | 10 |
| 4 | Compound A | 0.5 | PO | QD × 28 d | 10 |
| 5 | Compound A | 5.0 | PO | QD × 28 d | 10 |

Test articles were dissolved in 7% DMSO (Sigma) aqueous solution (v/v) and dosed P.O. in a 5 mL/kg volume once daily for 30 days from Day 29 to Day 58. The formulations were prepared twice per week.

Body weights were measured twice a week throughout the study, and food consumption (food in/food out) was recorded for the animals in all the groups on a weekly basis throughout the study.

Fast blood glucose levels of study animals were measured weekly after the induction period via tail vein bleeding by using Accu-Chek Performa System. All tests were conducted on Day 29 (baseline), 36, 43, 50 and 57. Animals were fasted overnight (16 hours from 17:00 to 9:00 on the next day) before measurement.

The serum lipid profile and liver enzyme levels were measured weekly after the induction period and specific blood chemistry parameters are listed in Table 3. All tests were conducted on Day 29 (baseline), 36, 43, 50 and 57. The blood was collected from orbital veins into a tube without anticoagulant, the serum samples were immediately processed by centrifugation at 4° C., 6000 g for 15 minutes, and then transferred into a new test tube. Lipid levels and full panel blood chemistry were measured by using TOSHIBA TBA-40FR automated biochemical analyzer.

TABLE 3

Blood Bio-chemistry Parameters

| Category | Abbreviation | Definition |
|---|---|---|
| Liver enzyme | ALT | Alanine aminotransferase |
| | AST | Aspartate aminotransferase |
| | ALP | Alkaline phosphatase |
| Blood lipid | TG | Triglycerides |
| | TCHO | Total Cholesterol |
| | HDL-C | High density lipoprotein cholesterol |
| | LDL-C | Low density lipoprotein cholesterol |
| | FFA | Free fatty acid |

The insulin levels of all study animals were measured on Day 57 with ELISA method. The blood serum was used for this analysis.

On the termination day (Day 59), a complete necropsy was conducted and liver was collected from all animals. The liver samples were divided into 3 portions; ⅓ was fixed in 10% formalin and processed into histological paraffin block, ⅓ was processed for lipid measurement (TG, TCHO, HDL-C, LDL-C and FFA) and the remaining ⅓ was snap frozen and stored at −80° C. for future analysis.

The statistical tests were conducted on all data, and the level of significance was set at 5% or P<0.05. The group means and standard deviation were calculated for all measurement parameters as study designed. One-way analysis of variance (ANOVA) was used among the groups with software GraphPad Prism 6.0.

Figure 14:
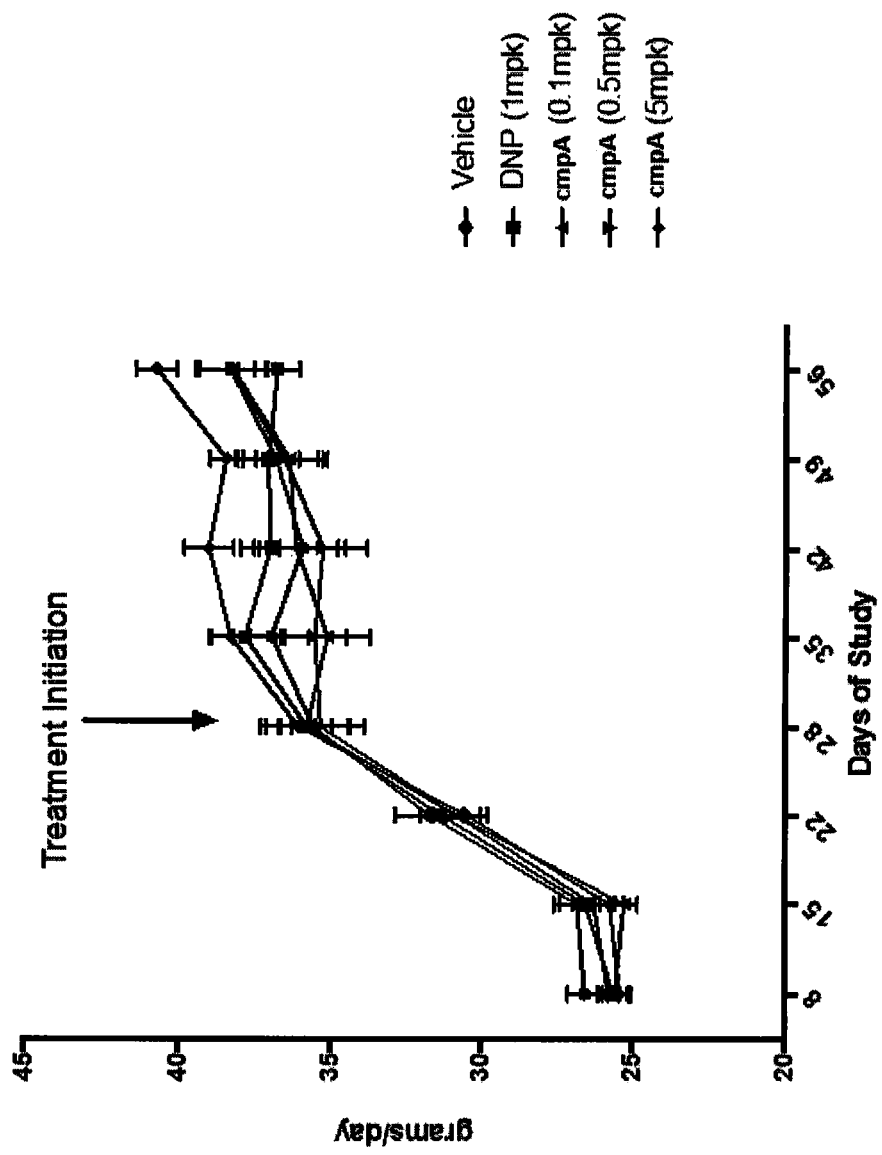
FIG. 14 illustrates Food Consumption Curves of Study Groups from Example 6.

We report that no significant changes in body weight and food consumption was observed between the study groups although a trend towards higher food consumption in the highest Compound A dosing group, coupled with a trend towards lower body weights in all dosing groups after day 36 compared to vehicle. FIG. 14 shows Food Consumption Curves of Study Groups from Example 6.

Figure 15:
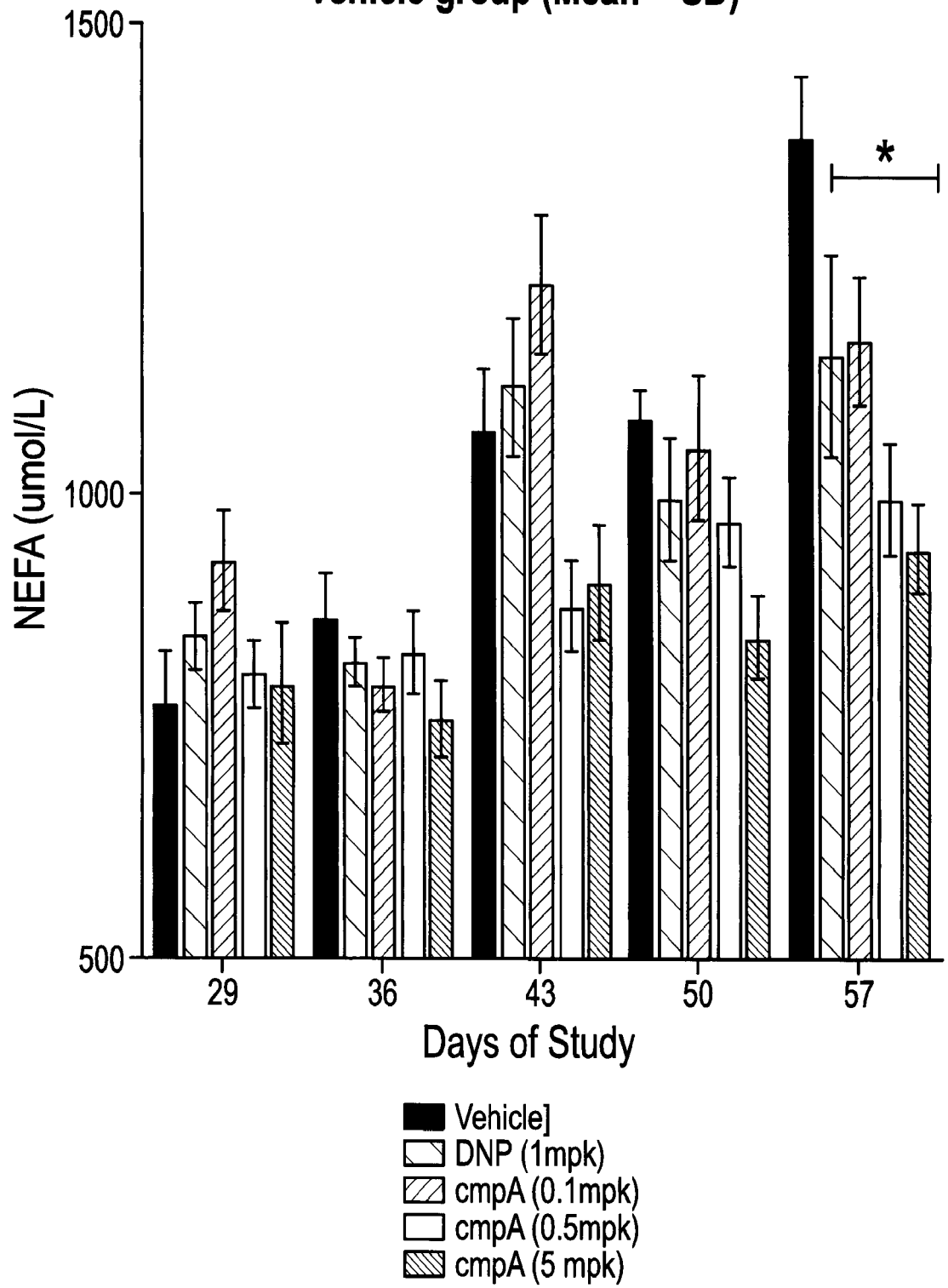
FIG. 15 illustrates Free Fatty Acid (FFA) level in the third group from Example 6. Note that $p<0.05$, compared with a $p<0.01$ when compared with vehicle group (Mean±SEM).
Figure 16:
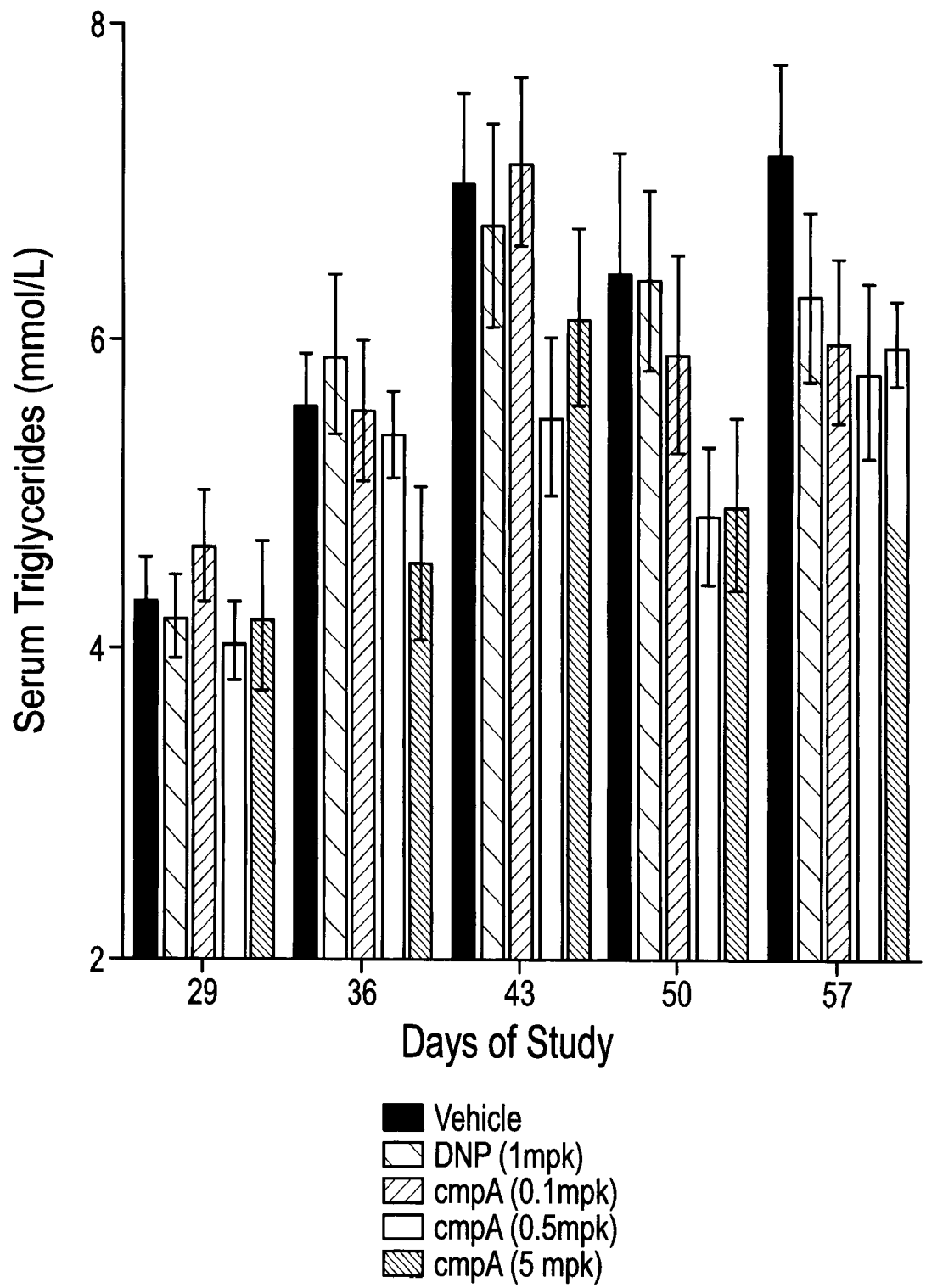
FIG. 16 illustrates blood TG (triglycerides) levels from Example 6 showing results in treated groups were lower than vehicle control in all study groups.
Figure 17:
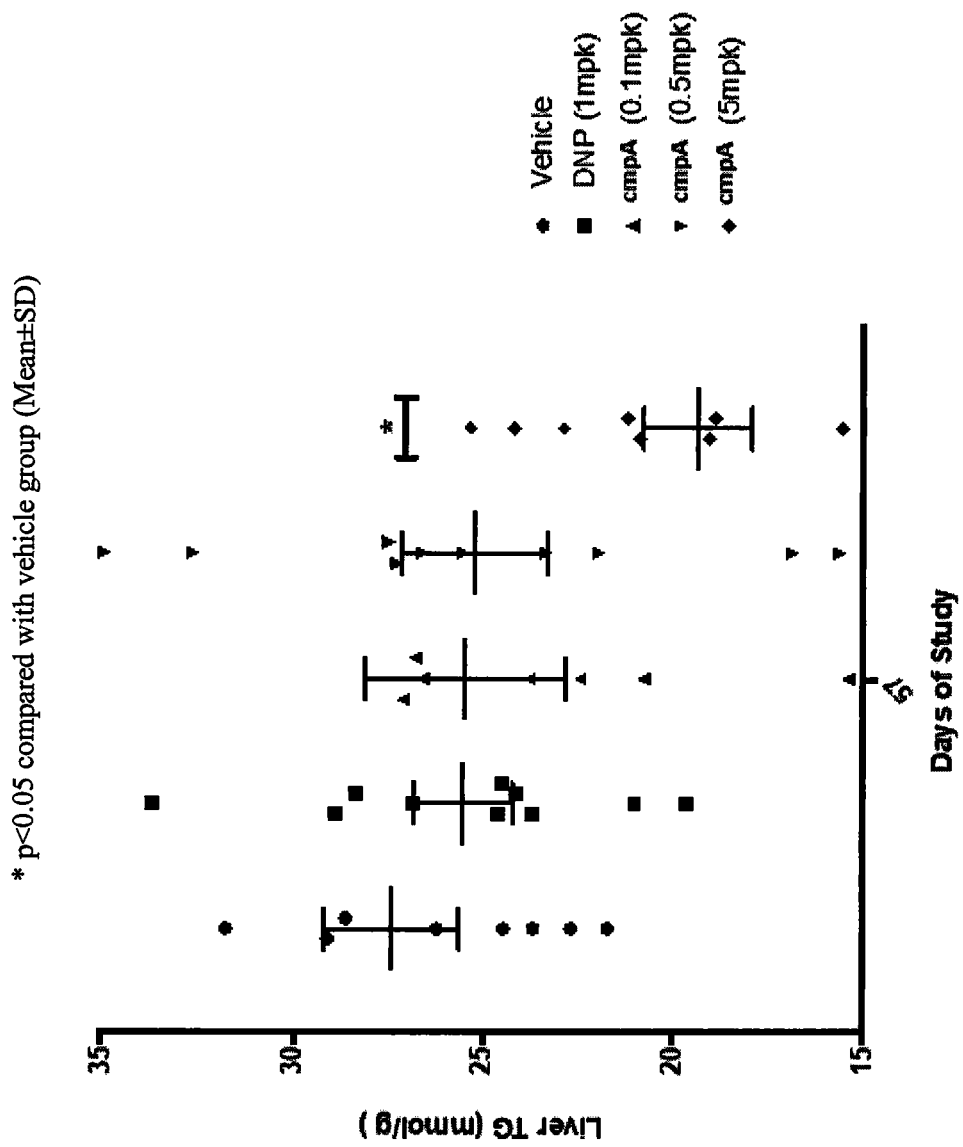
FIG. 17 illustrates liver TG were also lower in all study groups of Example 6 and the reduction had statistical significance in the group treated with the highest levels of Compound A (5.0 mg/kg) with a $p<0.05$ compared with vehicle group (Mean±SEM).
Figure 18:
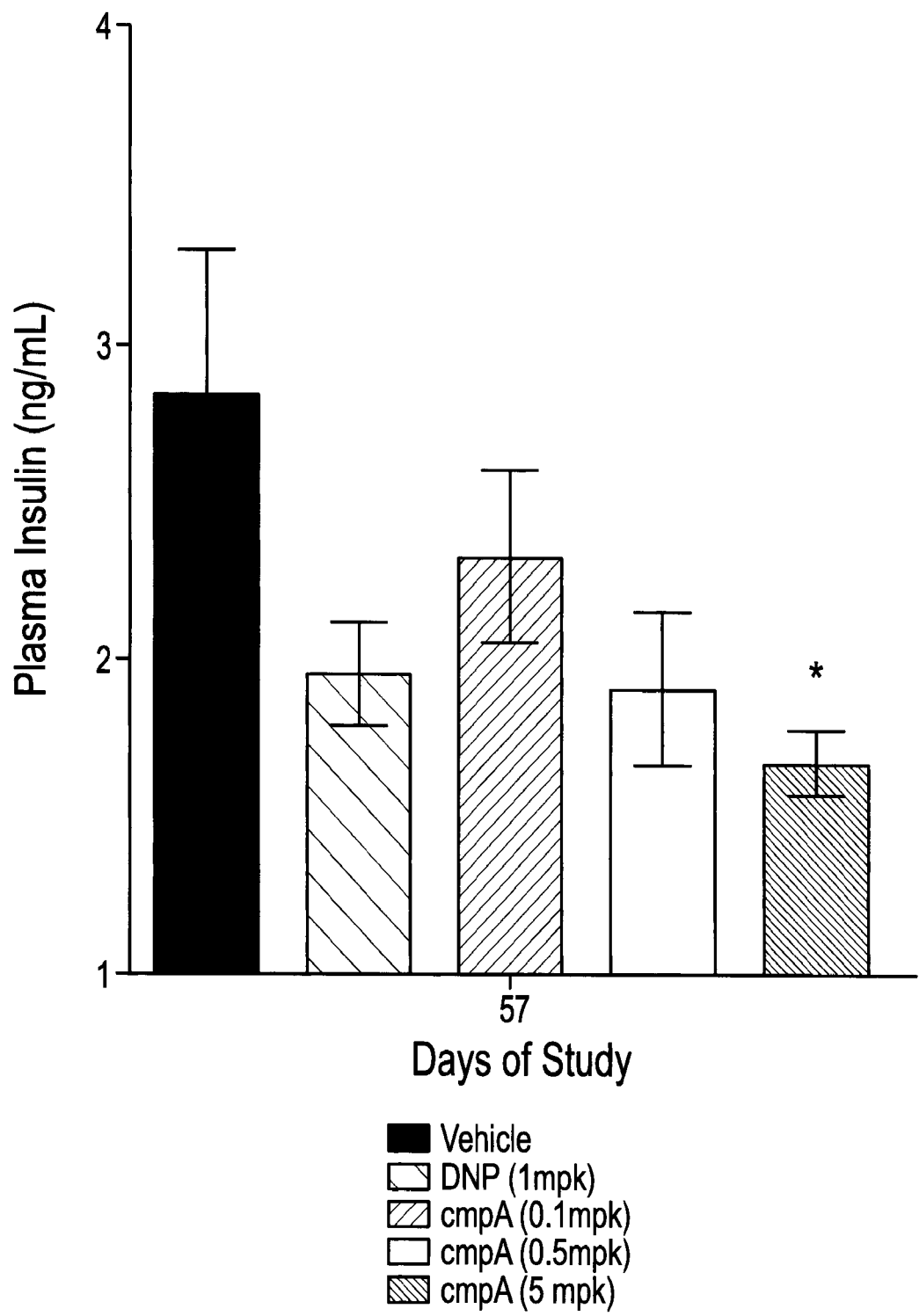
FIG. 18 illustrates blood insulin levels were observed to be lower in all treatment groups in Example 6.

FIG. 15 shows NEFA (Non-Esterified Fatty Acid, i.e. Free Fatty Acid (FFA)) levels were significantly lower in the two groups treated with the highest levels of Compound A. The third group, 0.1 mg/kg trended lower as well. See FIG. 15. Note that in FIG. 16 * p<0.05,  p<0.01 compared with vehicle group (Mean±SEM). FIG. 16 shows blood TG (triglycerides) levels showed similar results and were lower than vehicle control in all study groups, (Mean±SEM). See FIG. 16. FIG. 17** shows liver TG were also lower in all study groups, and the reduction did reach statistical significance in the group treated with the highest levels of Compound A (5.0 mg/kg) *p<0.05 compared with vehicle group (Mean±SEM) See FIG. 17. FIG. 18 shows blood insulin levels were observed to be lower in all treatment groups. Note * p<0.05 compared with vehicle group (Mean±SEM) (See FIG. 18). The study indicates that Compound A may be efficacious in reducing the risk for heart and cardiovascular diseases, and may be used to treat NAFLD, NASH and type 2 diabetes.

Example 7

Evaluation the Effect of Compound A in Hep3B-luc Human Liver Cancer Murine Orthotopic Model Sixty (60) Female BALB/c nude mice were quarantined for 7 days before the study. During the length of the study, animals were kept in standard laboratory conditions, and given free access to irradiation sterilized dry granule food and sterile drinking water. After the quarantine period, mice were inoculated in situ with 1×10E6 luciferase-expressing Hep3B-luc cells suspended in 10 µl MEM/Matrigel mixtures (7:3). The skin and peritoneum were incised to expose left liver lobe in anesthetized mice and the cells were injected slowly into the left liver lobe, so that a transparent bleb of cells were seen through the liver capsule. The tumor growth was monitored by image analysis. On Day 14, mice were randomized using a computer-generated randomization procedure into 6 groups based on the body weight and Bio Luminescent Imaging (BLI) values (10 mice per group) to ensure that the mean BLI were similar among the groups.

Study animals were monitored not only for tumor growth but also for behavior such as mobility, food and water consumption (by cage side checking only), body weight (BW), eye/hair matting and any other abnormal effect.

For BLI measures, mice were injected intraperitoneally with 15 mg/ml (at 5 µl/g BW) of D-luciferin (Pharmaron) and anesthetized with 1-2% isoflurane inhalation. At 10 minutes after the luciferin injection, the mice were imaged using IVIS Lumina II (Caliper) twice per week.

Living Image software (Caliper) was used to compute regions of interest (ROI) and integrate the total bioluminescence signal in each ROI. Bioluminescent signals (photons/s) from ROI were quantified and used as an indicator of tumor growth and antitumor activity.

Treatments were started when the mean tumor bioluminescent signals reached about 52×10E6 photons/s on day 14 post tumor cells inoculation. The animals were divided into the following treatment groups (n=10/group):
1. Vehicle Control
2. Sorafenib Tosylate 80 mg/kg
3. Sorafenib Tosylate 80 mg/kg+25 mg/kg Compound A
4. Sorafenib Tosylate 80 mg/kg+100 mg/kg Compound A
5. Sorafenib Tosylate 80 mg/kg+200 mg/kg Compound A
6. Sorafenib Tosylate 80 mg/kg+300 mg/kg Compound A All drugs were dissolved in 7% DMSO+20% Hydroxypropyl beta cyclodextrin (HPBCD).

No changes in body weight were observed during the course of the trial, or between the study groups. Sorafenib as single agent showed a trend toward having an effects on decreasing BLI of Hep3B-luc human liver tumor in vivo bioluminescence after 28 days consecutive treatment (See FIG. 19). However, this effect was not augmented by Compound A in any of the tested dosing levels, Compound A does not appear to improve the effect of Sorafenib or sensitize the cells to apoptosis. In fact, Sorafenib alone had the lowest BLI at the end of the study. All test articles were well tolerated at currently test condition by the orthotopic tumor-bearing mice.

Figure 19:
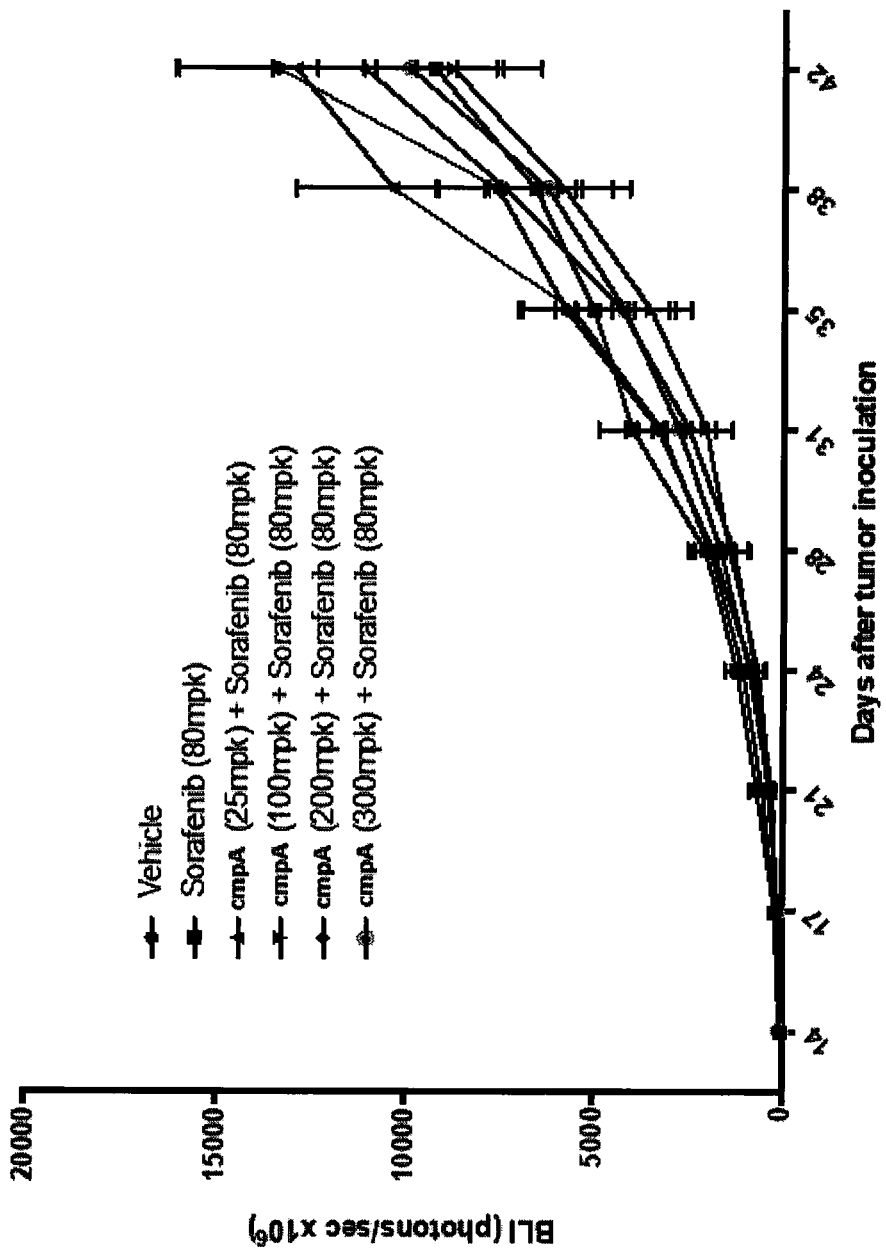
FIG. 19 illustrates the Effect of Sorafenib alone and in combination with Compound A in the Treatment of Orthotopic Model of Human Hep3B-luc Hepatic Cancer as described in Example 7.

No other gross clinical abnormalities were observed in all the animals during the treatment period. FIG. 19 illustrates the effect of Sorafenib alone and in combination with Compound A in the Treatment of Orthotopic Model of Human Hep3B-luc Hepatic Cancer.

Example 8

Description of Compound A Efficacy in Diet Induced Animal Model of Non-alcoholic Fatty Liver Disease This study evaluated the effect of Compound A on steatohepatitis and the progression to fibrosis in Diet Induced Animal Model of Non-alcoholic fatty liver Disease (DIAMOND) Male C57BL/6J(B6)-129s1/SvImJ(S 129) mice. The Sanyal DIAMOND mouse model recapitulates the key physiological, metabolic, histologic, transcriptomic and cell-signaling changes seen in humans with progressive NASH. Also see *Journal of Hepatology* Volume 65, Issue 3, September 2016, Pages 579-588 'A diet-induced animal model of non-alcoholic fatty liver disease and hepatocellular cancer' by A. Asgharpour et al.

Two dose levels of Compound A (1 mg/kg or 5 mg/kg daily dose in vehicle for 8 weeks) was compared with vehicle control and historical data from strain matched negative control mice on normal chow (Harlan Normal Rodent Chow, TD 7012 Teklad LM-485) and Reverse Osmosis (RO) purified water.

At the beginning of the study (Week 0), 30 8-12 weeks old male mice were fed a Western Diet ad libitum, Harlan 42% Calories from Fat (Harlan TD.88137) and sugar water (SW 23.1 g/L d-fructose+18.9 g/L d-glucose). The mice were allowed to progress to steatohepatitis for 12 weeks after which they were randomly divided into three treatment groups (n=10):
1. Vehicle Control—0.5% aqueous sodium carboxymethyl cellulose with 0.1% Tween-80 (VC)
2. Compound A 1.0 mg/kg/day in vehicle (Low dose Compound A)
3. Compound A 5.0 mg/kg/day in vehicle (High dose Compound A)
An additional two groups (historical data) were also used for comparison.
4. Negative Control—mice fed a normal chow diet (20 weeks NC)
5. Positive Control—mice fed a WD with SW, no treatment, no gavage (20 weeks PC)

After eight weeks of treatment after week 20, all mice were necropsied.

We found that animals dosed with 5 mg/kg showed a significant body weight reduction in week 20. Animals in this group also had a statistically significant lower liver weight, total cholesterol, ALT, ALP, and ASP values. Lobular inflammation was significantly reduced with compound A. NAS and SAF activity score were significantly lowered with compound A.

Significant reduction in progression to NASH with compound A (only one mouse on compound A progressed to NASH whereas all controls progressed to NASH). The study indicates that Compound A will be efficacious in treating NAFLD and NASH, and may also be efficacious in lowering BMI to treat obesity, and reduce the risk for heart disease.

Figure 20:
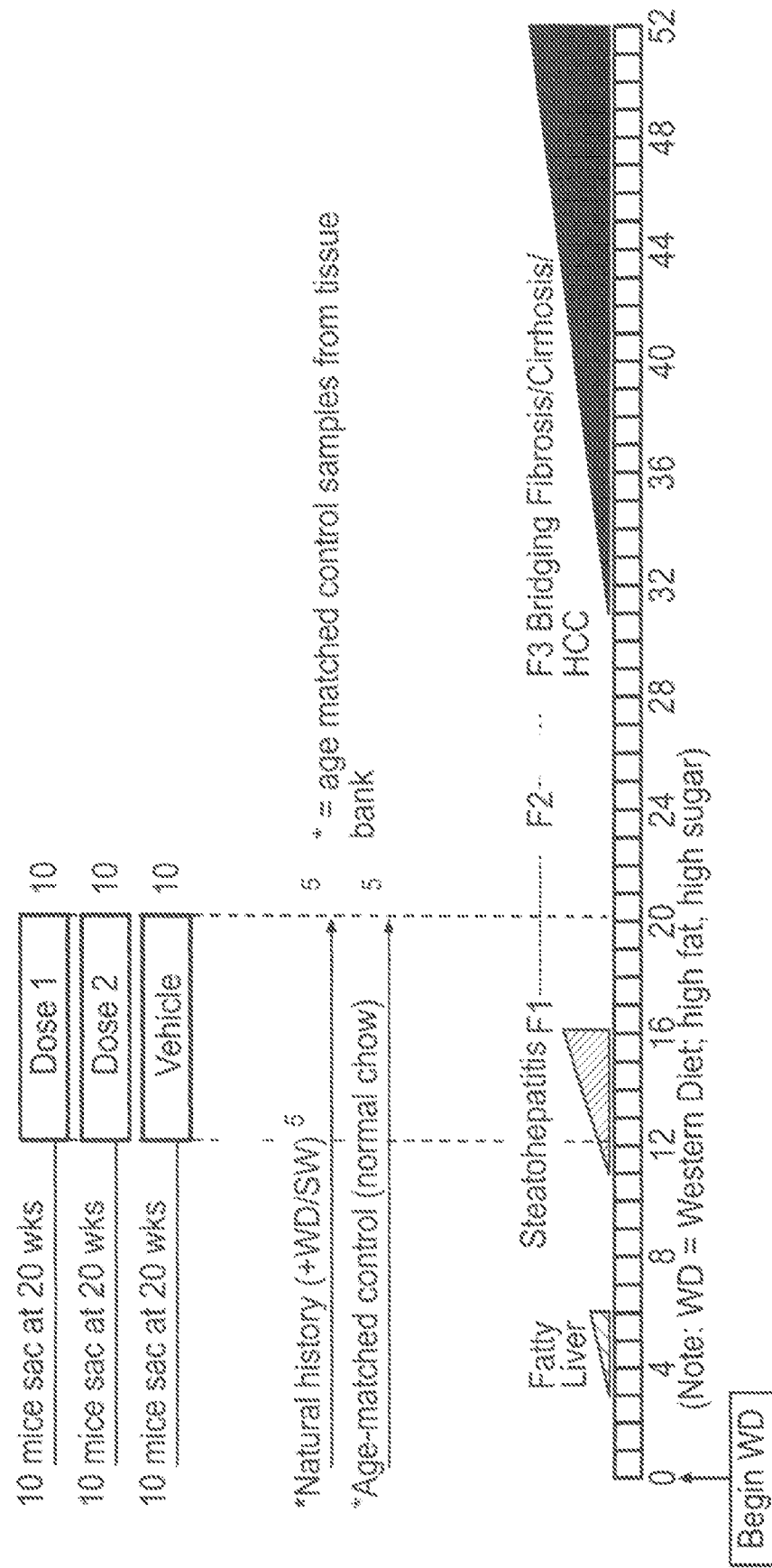
FIG. 20 illustrates experimental design and disease progression in the diet induced animal model of non-alcoholic fatty liver disease. See Example 8.
Figure 21:
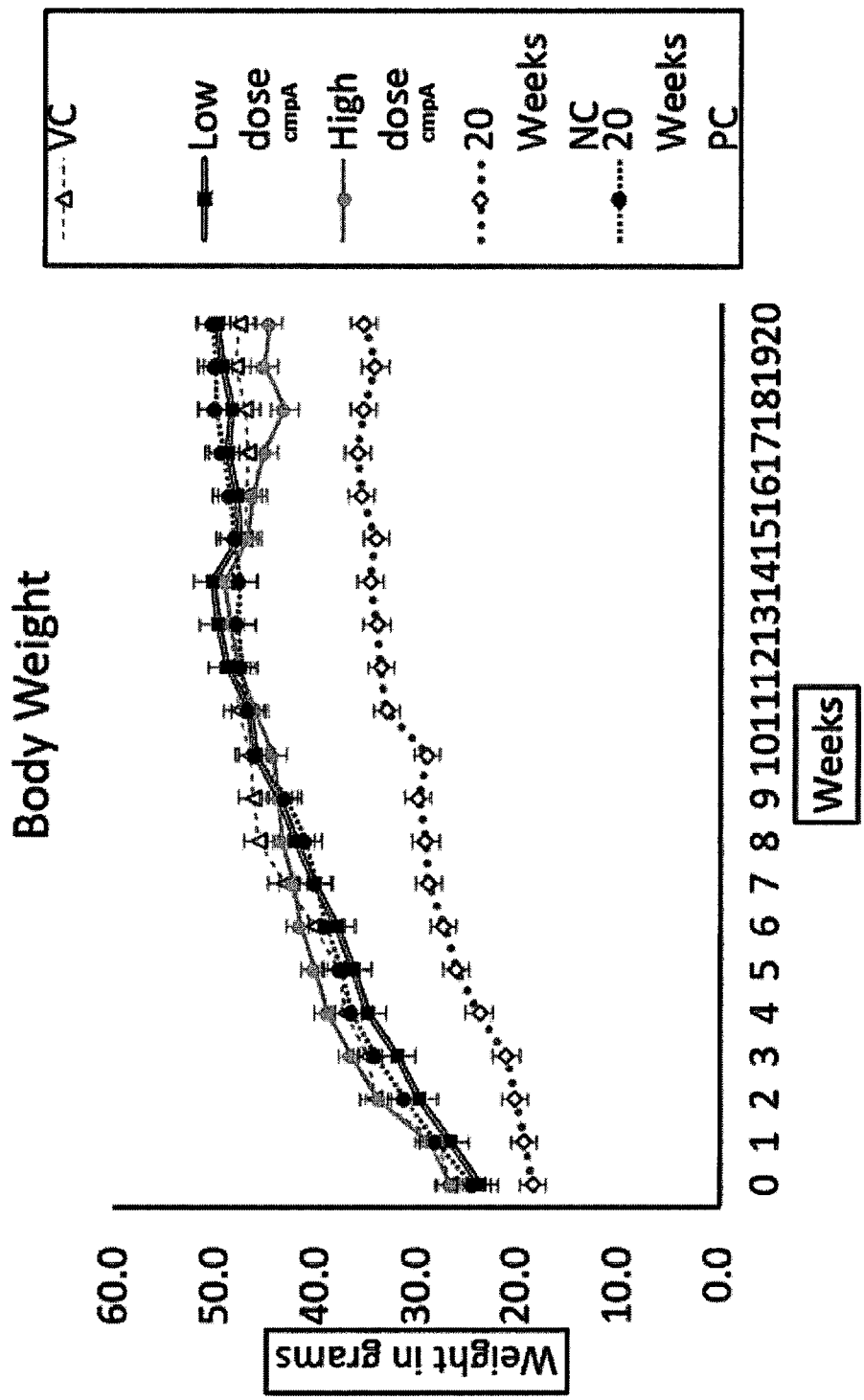
FIG. 21 illustrates body weight development in the diet induced animal model of non-alcoholic fatty liver disease after western diet is introduced (week 0) and during treatments (week 12-20). The data shows a significant overall body weight reduction in High Dose Compound A. See Example 8.
Figure 22:
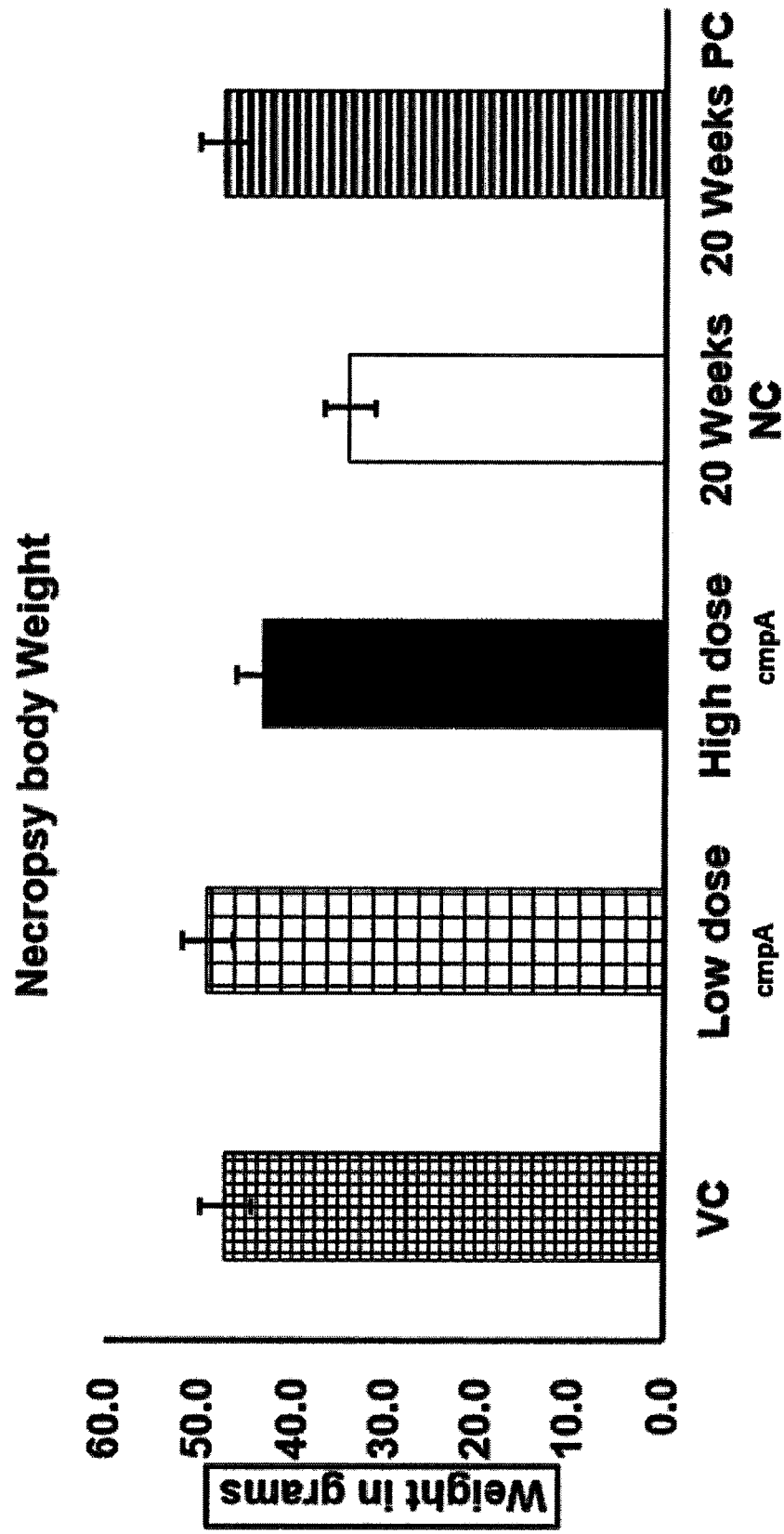
FIG. 22 illustrates a significant overall body weight reduction in the diet induced animal model of non-alcoholic fatty liver disease after eight weeks of High Dose Compound A. See Example 8.
Figure 23:
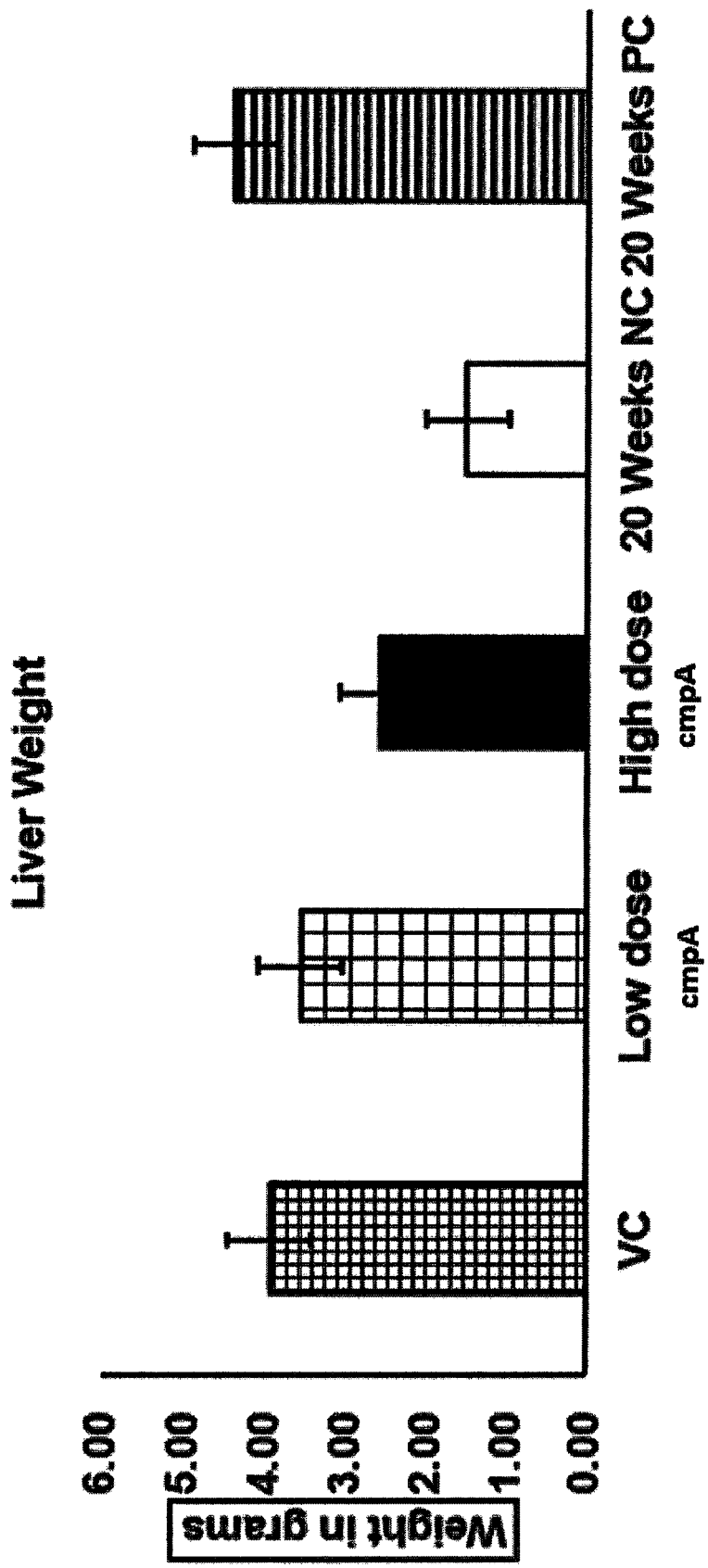
FIG. 23 illustrates the effect of low and high dose Compound A in the diet induced animal model of non-alcoholic fatty liver disease on liver weight after eight weeks of dosing. See Example 8.
Figure 24:
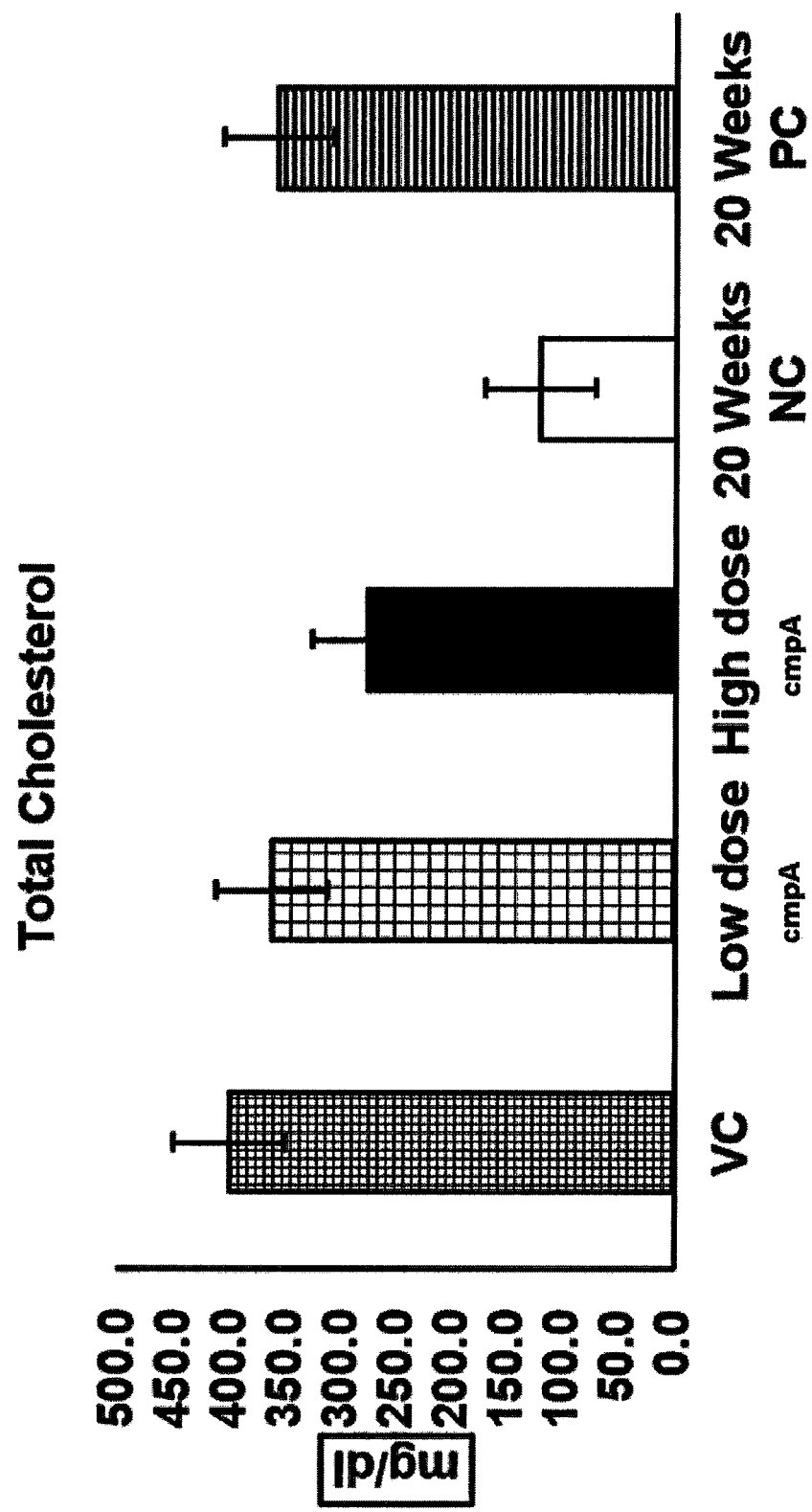
FIG. 24 illustrates the effect of low and high dose Compound A in the diet induced animal model of non-alcoholic fatty liver disease on liver weight after eight weeks of dosing. See Example 8.
Figure 25:
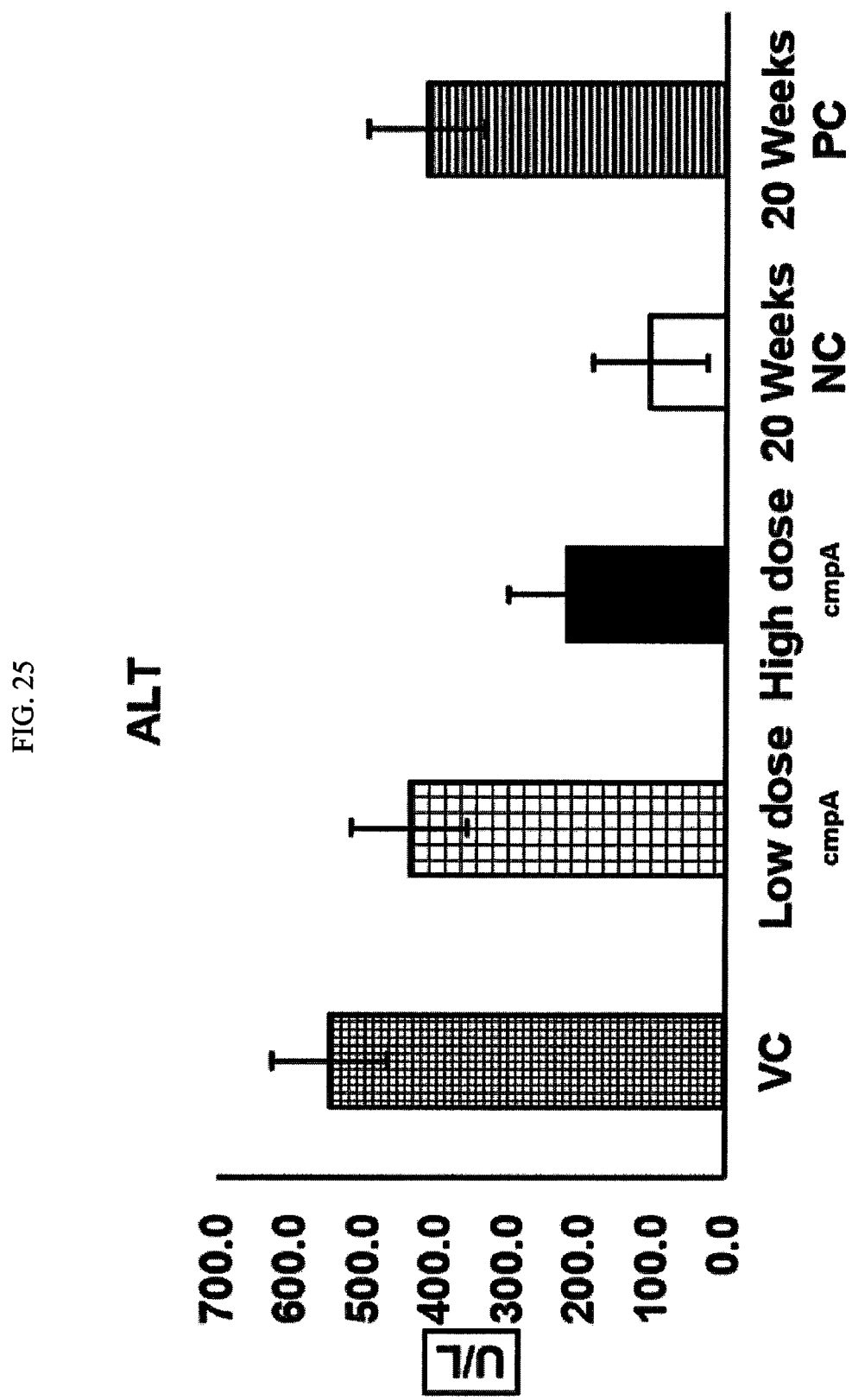
FIG. 25 illustrates the effect of low and high dose Compound A in the diet induced animal model of non-alcoholic fatty liver disease on serum levels of ALT (alanine aminotransaminase.) See Example 8.
Figure 26:
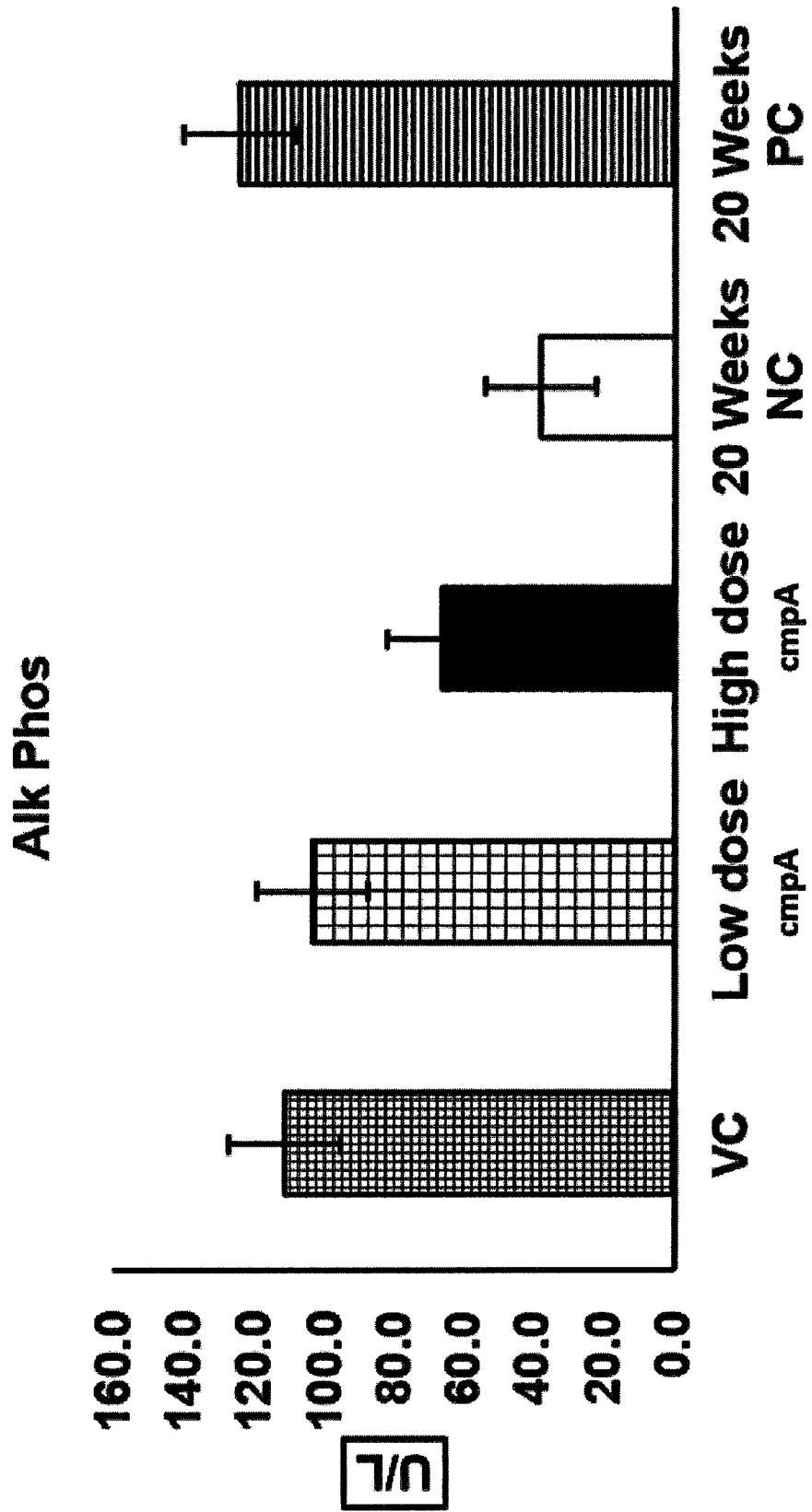
FIG. 26 illustrates the effect of low and high dose Compound A in the diet induced animal model of non-alcoholic fatty liver disease on serum levels of Alk Phos (Alkaline Phosphatase.) See Example 8.
Figure 27:
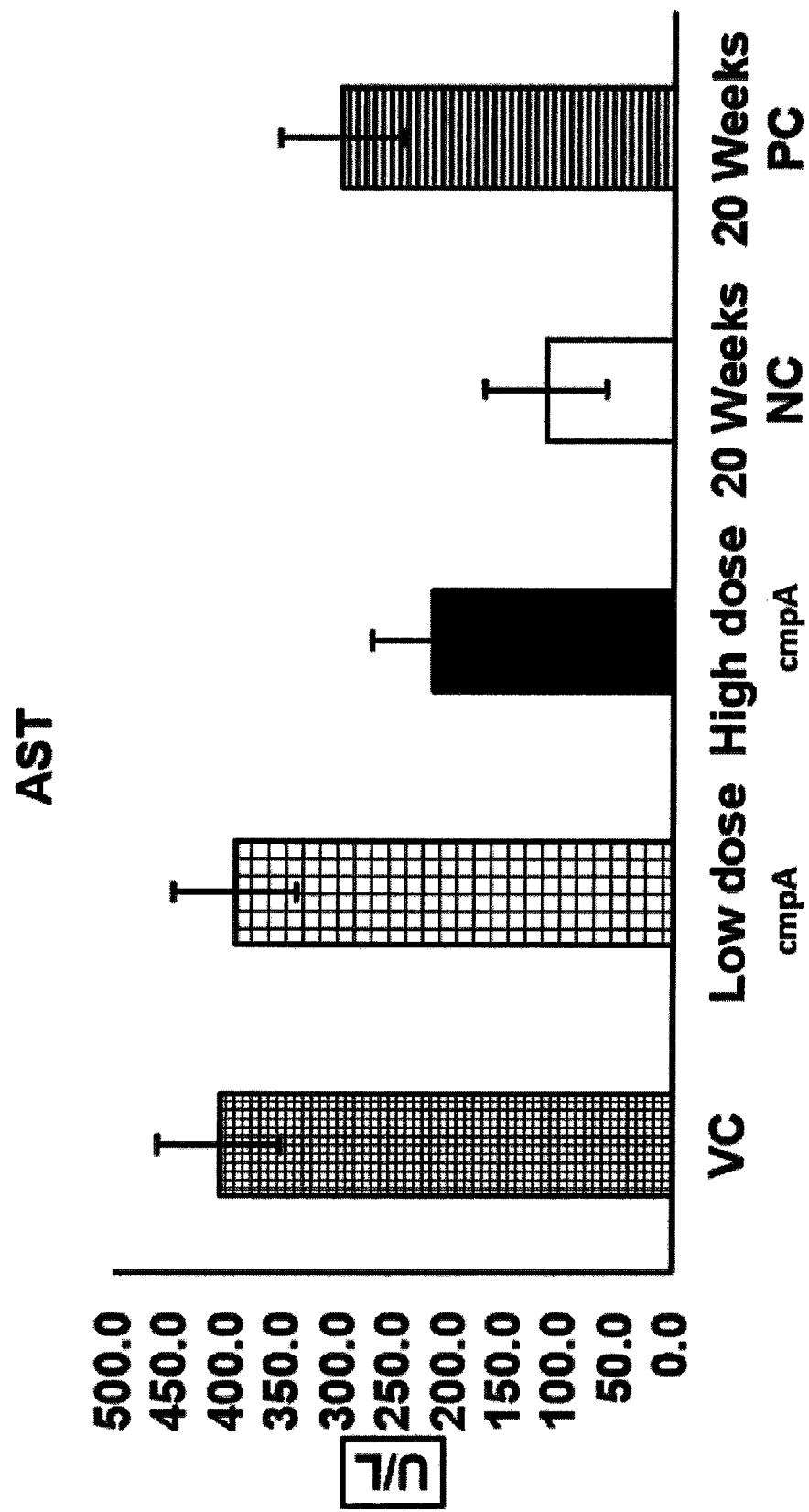
FIG. 27 illustrates the effect of low and high dose Compound A in the diet induced animal model of non-alcoholic fatty liver disease on serum levels of AST (aspartate transaminase.) See Example 8.
Figure 28:
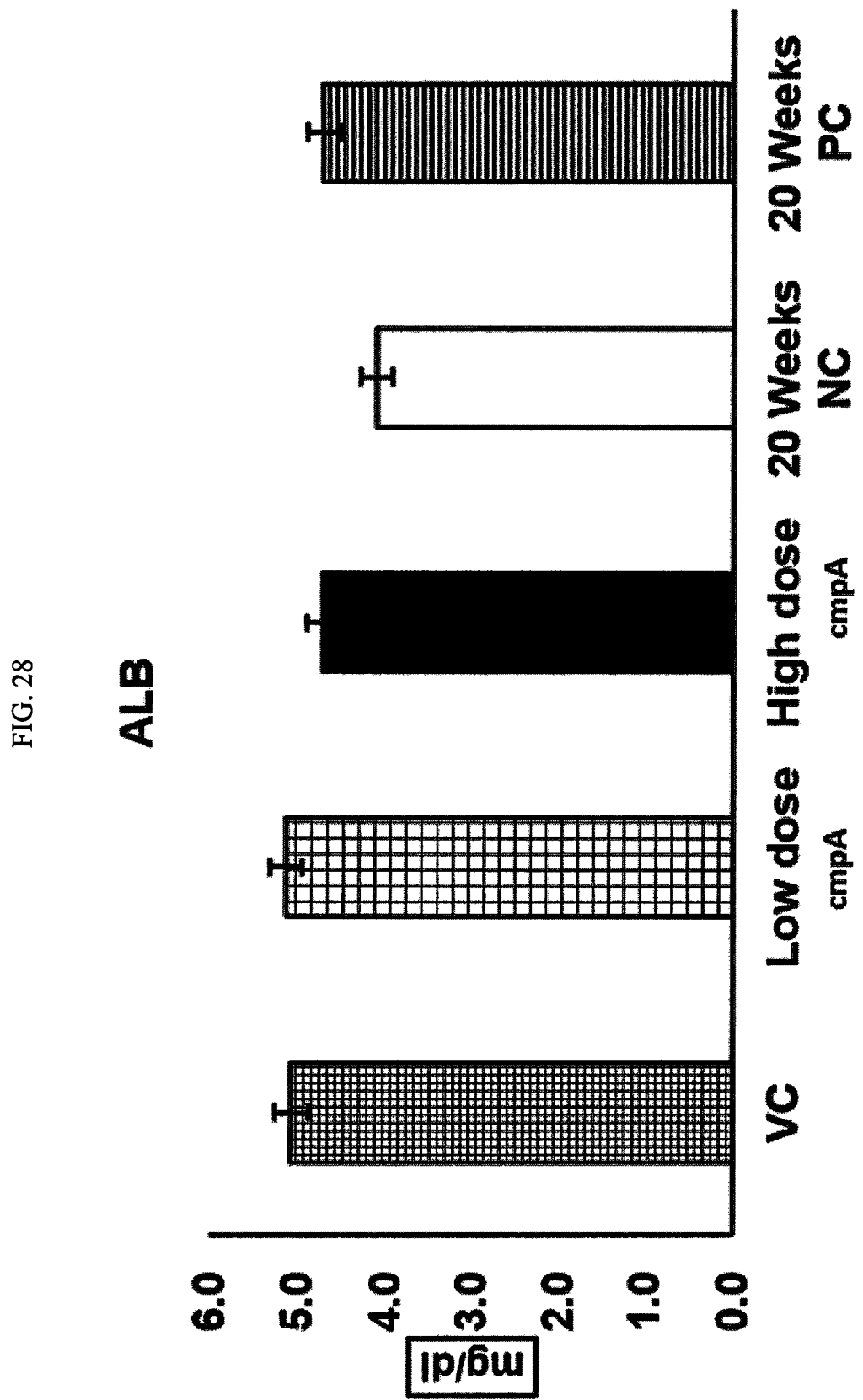
FIG. 28 illustrates the effect of low and high dose Compound A in the diet induced animal model of non-alcoholic fatty liver disease on serum levels of ALB (Albumin). See Example 8.

These results are described in the following figures: FIG. 20 illustrates experimental design and disease progression in the diet induced animal model of non-alcoholic fatty liver disease. FIG. 21 illustrates body weight development in the diet induced animal model of non-alcoholic fatty liver disease after western diet is introduced (week 0) and during treatments (week 12-20). The data shows a significant overall body weight reduction in High Dose Compound A. FIG. 22 illustrates a significant overall body weight reduction in the diet induced animal model of non-alcoholic fatty liver disease after eight weeks of High Dose Compound A. FIG. 23 illustrates the effect of low and high dose Compound A in the diet induced animal model of non-alcoholic fatty liver disease on liver weight after eight weeks of dosing. FIG. 24 illustrates the effect of low and high dose Compound A in the diet induced animal model of non-alcoholic fatty liver disease on liver weight after eight weeks of dosing. FIG. 25 illustrates the effect of low and high dose Compound A in the diet induced animal model of non-alcoholic fatty liver disease on serum levels of ALT (alanine aminotransaminase). FIG. 26 illustrates the effect of low and high dose Compound A in the diet induced animal model of non-alcoholic fatty liver disease on serum levels of ALP (Alkaline Phosphatase.) FIG. 27 illustrates the effect of low and high dose Compound A in the diet induced animal model of non-alcoholic fatty liver disease on serum levels of ALP (Alkaline Phosphatase.) FIG. 28 illustrates the effect of low and high dose Compound A in the diet induced animal model of non-alcoholic fatty liver disease on serum levels of ALB (Albumin).

Example 9

Preparation of 5-[(2,4-dinitrophenoxy)methyl]-1-methyl-2-nitro-1H-imidazole (Compound #2 in Table A or Compound A)

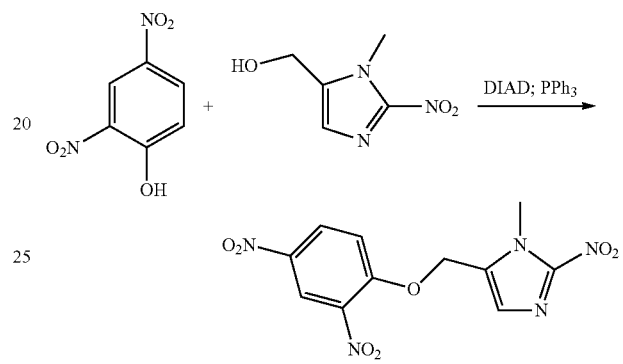

2,4-Dinitrophenol (wetted with ca. 20% water, from TCI America, Cat. No. D0109) (269 mg wet weight, 215 mg dry weight, 1.17 mmol) is dissolved in methylene chloride (2 mL) and stirred with anhydrous sodium sulfate at room temperature for 3 hours. The methylene chloride solution is decanted into a reaction flask and the sodium sulfate is washed with additional methylene chloride (2 mL). To the solution is added (1-methyl-2-nitro-1H-imidazol-5-yl)methanol (115 mg, 0.732 mmol, prepared by the procedure described in U.S. Pat. No. 8,003,625 B2) and triphenylphosphine (211 mg, 0.805 mmol). The mixture is stirred at room temperature until a solution is achieved. The solution is then cooled in an ice bath and treated with diisopropyl azodicarboxylate, DIAD (158 µL, 0.805 mmol). After 1 hour the ice bath is removed and the mixture is stirred overnight at room temperature. Crude product is purified on a silica gel column to isolate the product mixed with triphenylphosphine oxide. The solids are triturated with t-butyl methyl ether to remove the triphenylphosphine oxide to afford 5-[(2,4-dinitrophenoxy)methyl]-1-methyl-2-nitro-1H-imidazole (70 mg, 0.236 mmol, 30% yield).

$^1$H NMR (DMSO-$d_6$) δ 8.80 (d, J=2.4 Hz, 1 H), 8.58 (dd, J=9.6, 2.4 Hz, 1 H); δ 7.82 (D, J=9.6 Hz, 1 H), 7.40 (s, 1 H), 5.66 (s, 2 H), 3.95 (s, 3 H). MS (ESI+) for $C_{11}H_9N_5O_7$ m/z 324.1 (M+H)$^+$.

Example 10

Evaluation of the Growth Inhibitory Properties of Compound a in the NCI-60 Cancer Cell Line Panel The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Aliquots of 100 µl of the drug dilution is added to the appropriate microtiter wells already containing 100 µl of medium, resulting in the required final drug concentration.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

The One-dose data is shown as a mean graph of the percent growth of treated cells. The number reported is growth relative to the no-drug control, and relative to the time zero number of cells. This allows detection of both growth inhibition (values between 0 and 100) and lethality (values less than 0).

Figure 29:
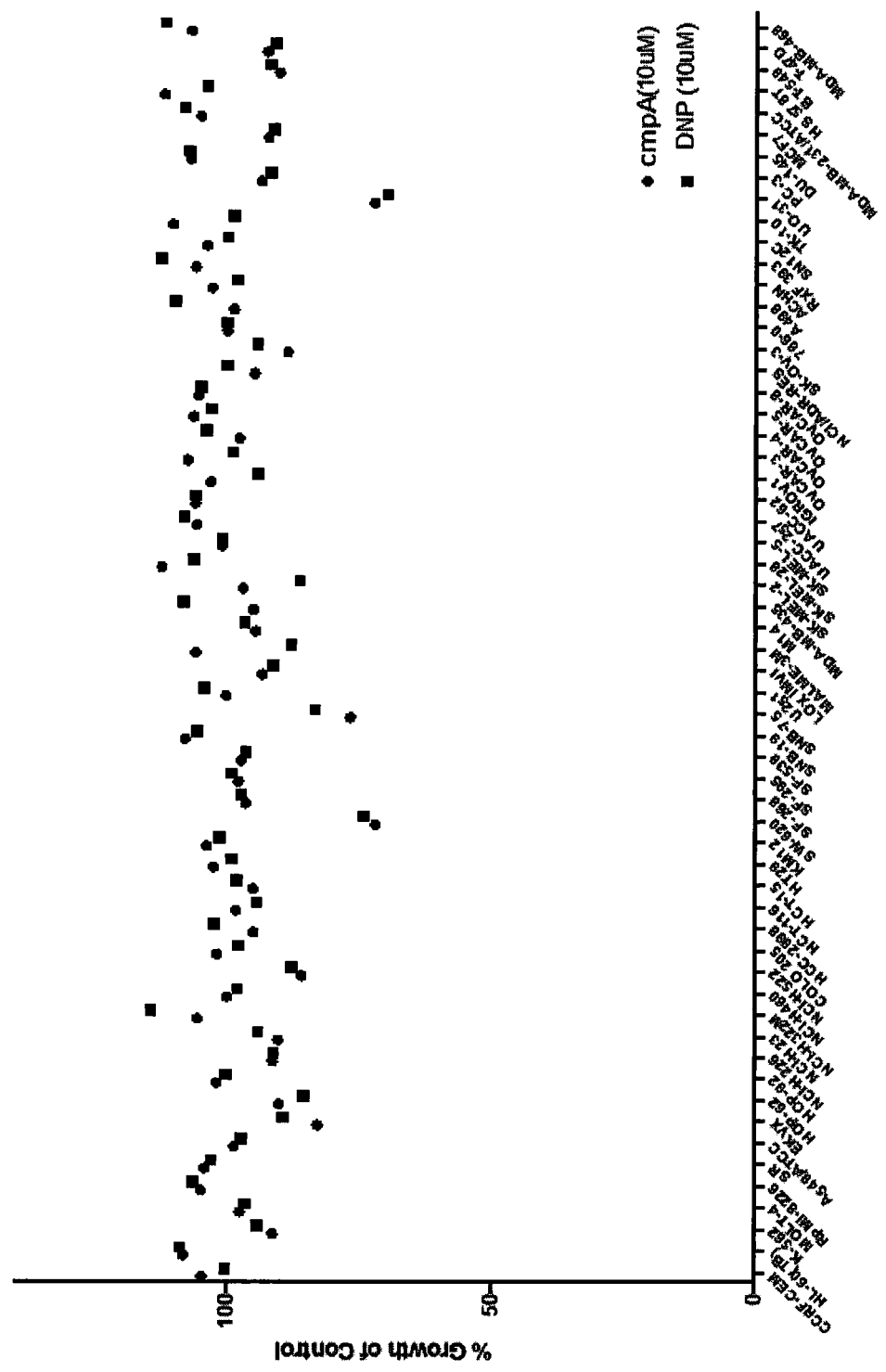
FIG. 29 illustrates the cell growth of NCI-60 cell lines treated with either Compound A or DNP at 10 μM. See Example 10.

Across the NCI-60, Compound A had a mean growth percent of control of 98.63 with a delta of 26.47 percent across all cell lines tested and a range of 40.14 percent. Similarly, DNP had a mean growth percent of control of 98.4 percent with a delta of 28.44 across all cell lines tested with a range of 44.43 percent. The results by cell line are shown below. Neither Compound A nor DNP produced robust growth inhibition (at least 50 percent) at 10 uM in any of the NCI-60 cell lines. FIG. 29 shows the cell growth of NCI-60 cell lines treated with either Compound A or DNP at 10 µM.

Example 11

Formation of DNP from Compound A by Liver Microsomes

Step 1: A solution was prepared according to Table 4.

TABLE 4

Preparation of Master Solution

| Reagent | Stock Concentration | Volume | Final Concentration |
|---|---|---|---|
| Phosphate buffer | 200 mM | 200 µL | 100 mM |
| Ultra-pure H$_2$O | — | 106 µL | — |
| MgCl$_2$ solution | 50 mM | 40 µL | 5 mM |
| Microsomes | 20 mg/mL | 10 µL | 0.5 mg/mL |

Figure 30:
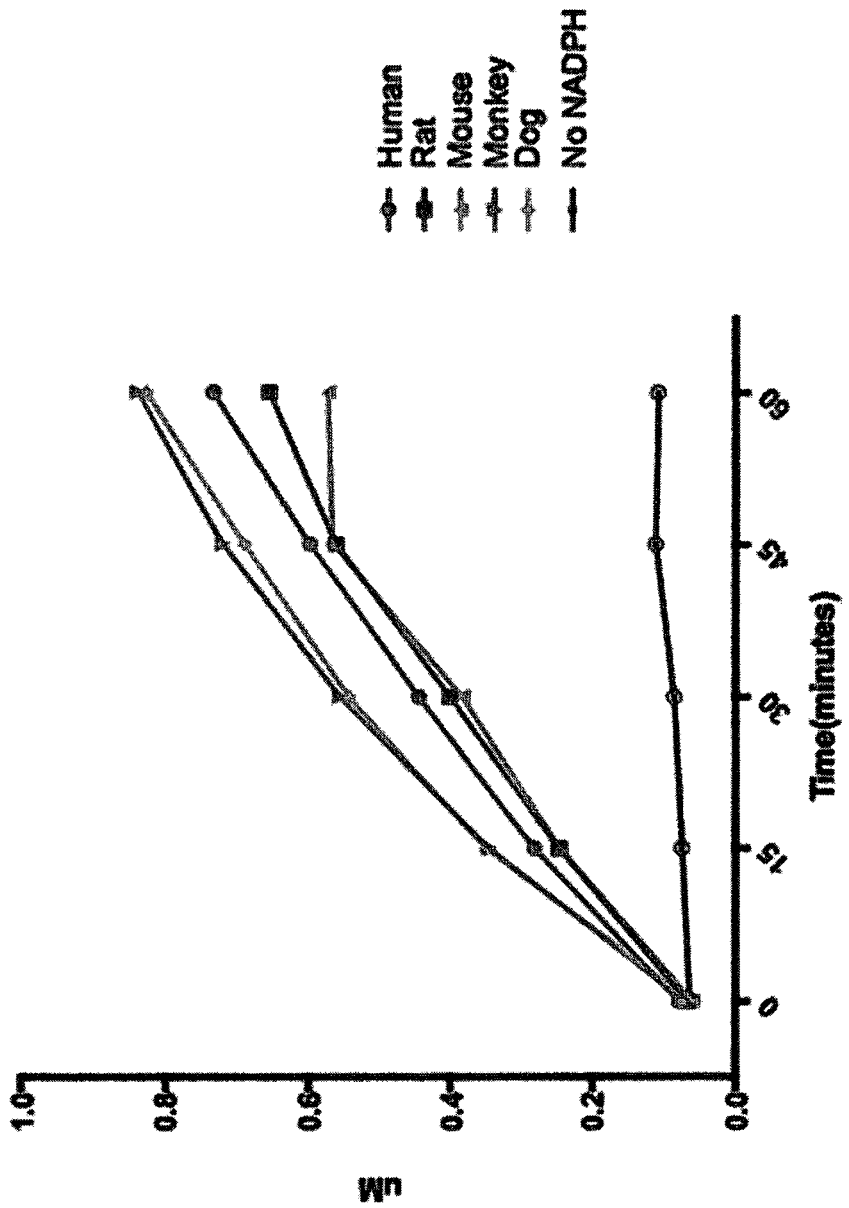
FIG. 30 illustrates the formation of DNP from 2 μM Compound A in liver microsomes from different species and that this formation requires NADPH. See Example 11.
Figure 31:
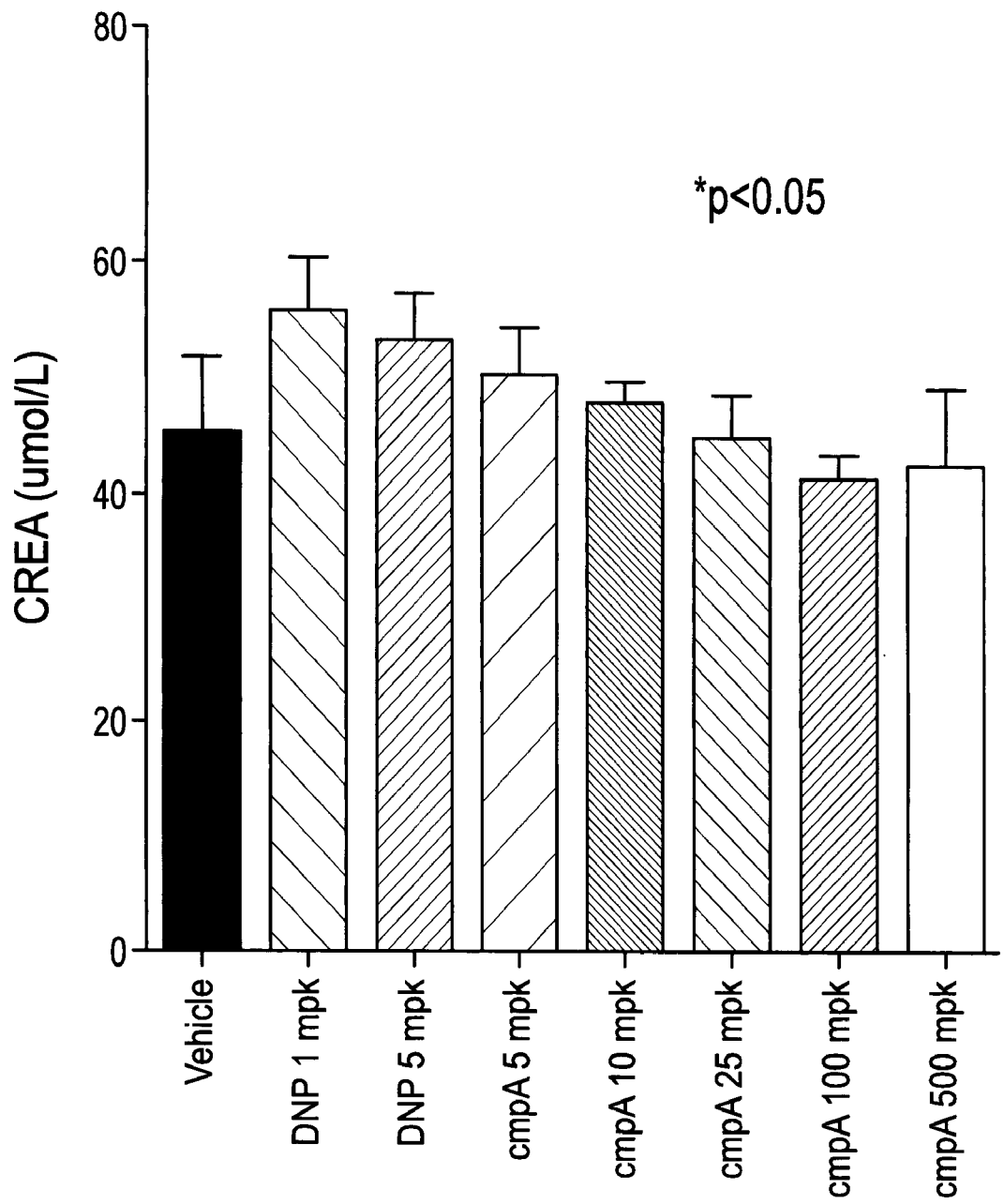
FIG. 31 illustrates 7-day repeat dose mouse toxicity study to assess changes in behavioral and safety parameters. Compound A administered orally at levels as high as 500 mg/kg did not cause kidney dysfunction as measured by creatinine in the blood, while as little as 1 mg/kg or DNP raised blood creatinine. Changes in Creatinine are Cmax dependant.
Figure 32:
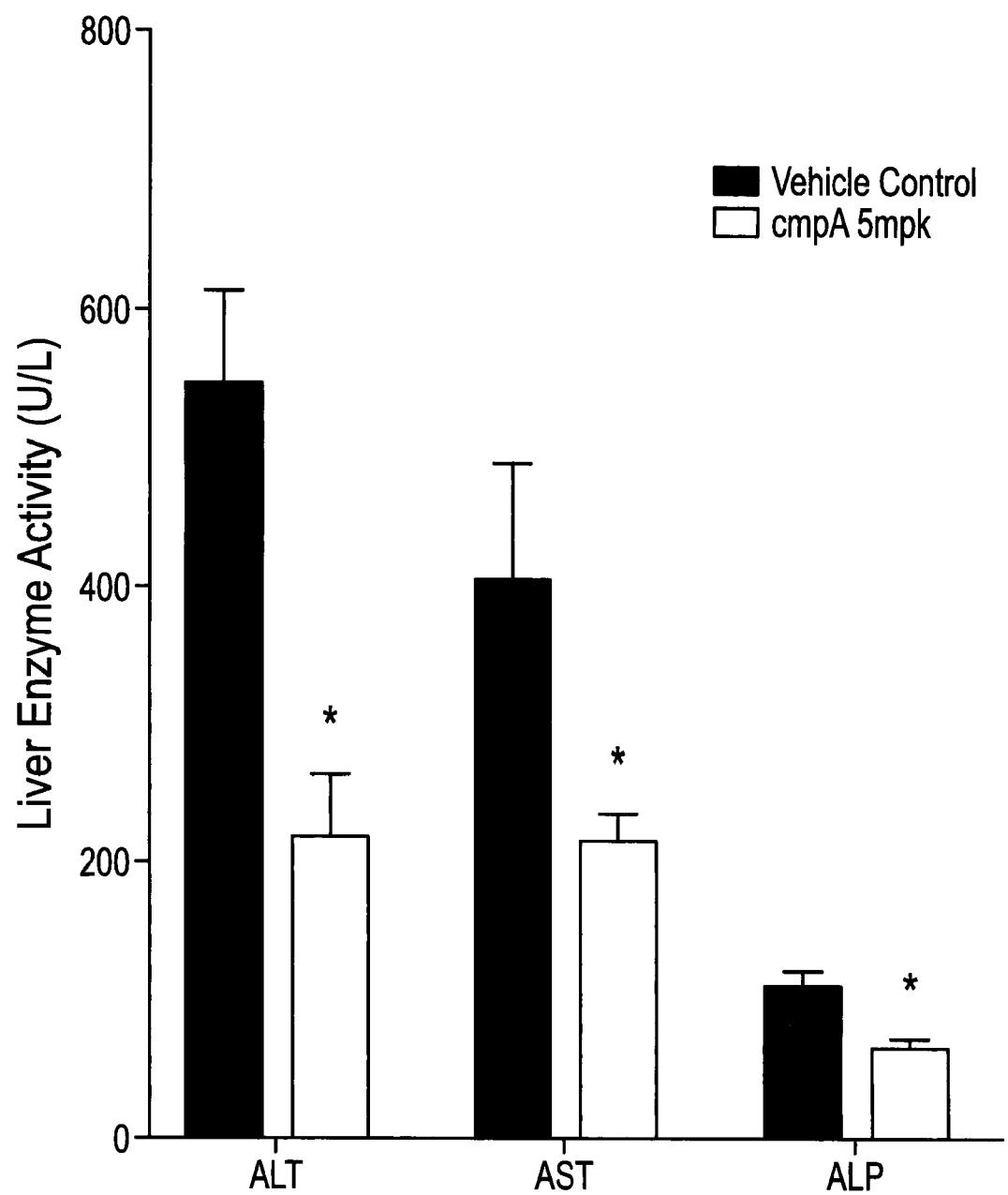
FIG. 32—illustrates the effect of high dose Compound A in the diet induced animal model of non-alcoholic fatty liver disease on serum levels of ALT, AST and ALP. See Example 8.
Figure 33:
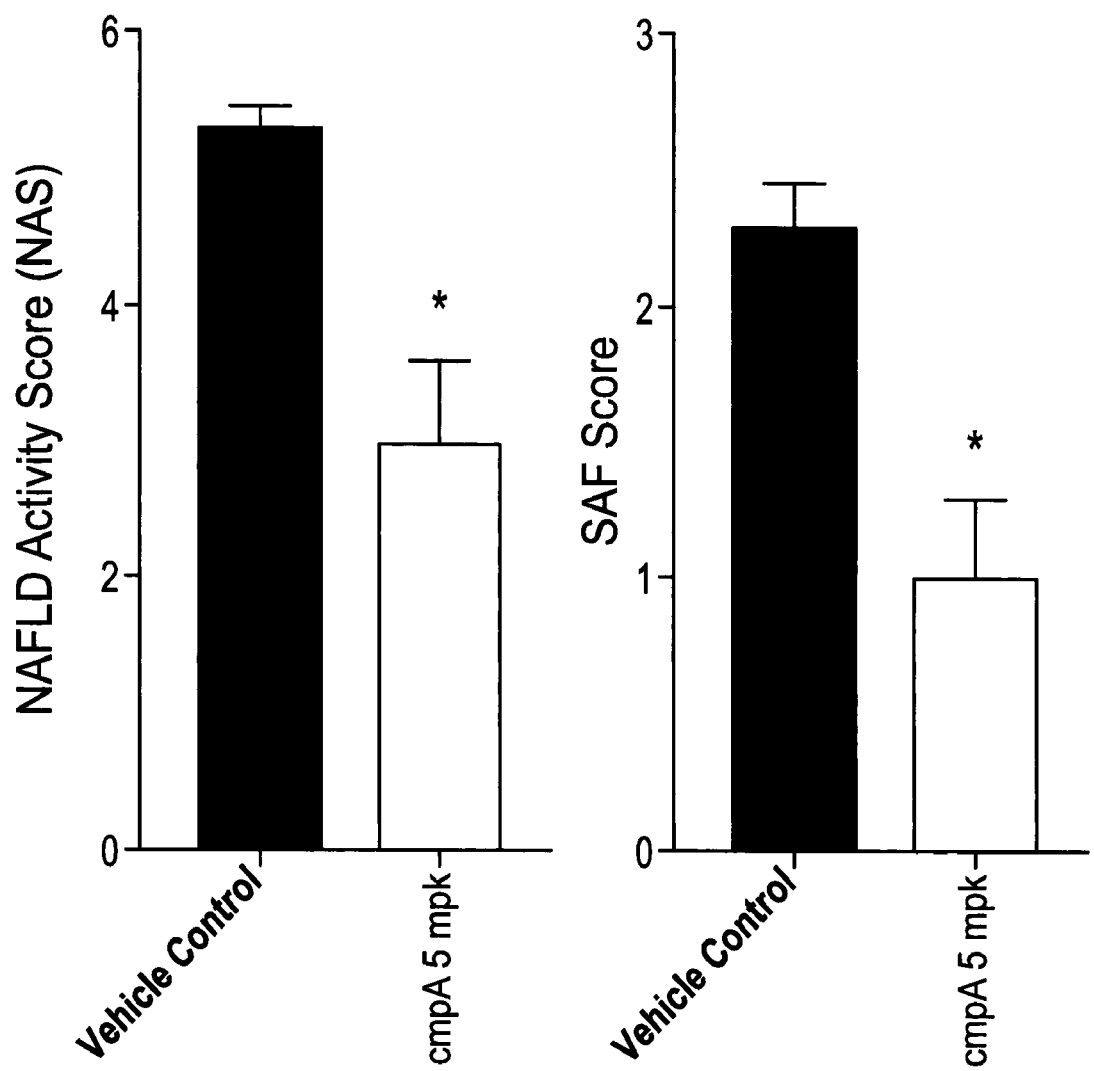
FIG. 33 illustrates the effect of high dose Compound A on NAS and SAF activity scores. Both were significantly lowered with compound A.

Step 2: 40 µL of 10 mM NADPH solution was added to each well. The final concentrations of NADPH was 1 mM. The mixture was pre-warmed at 37° C. for 5 min. The negative control samples were prepared by replacing NADPH solutions with 40 µL of ultra-pure H2O. The negative control was used to exclude the misleading factor that resulted from instability of chemical itself. Samples with NADPH were prepared in duplicate. Negative controls were prepared in singlet (See FIG. 30). Formation of DNP from 2 µM Compound A in liver microsomes from different species. The source of the tested species are listed in table 5.

TABLE 5

Liver Microsomes Information

| Species | Cat. No. | Lot. No. | Strain & Gender | Supplier |
|---|---|---|---|---|
| Human | 452117 | 38291 | Pooled, Male & Female | Corning |
| Rat | 452501 | 62547 | Pooled, Male Sprague-Dawley | Corning |
| Mouse | 452701 | 4133003 | Pooled, Male CD-1 | Corning |
| Monkey (cyno) | — | ZDD | Pooled, Male Cynomolgus | RILD (Shanghai) |
| Dog | D1000 | 1310086 | Pooled, Male Beagle | Xenotech |

Step 3: The reaction was started with the addition of 4 µL of 200 µM control compound or test compound solutions. Verapamil was used as positive control in this study. The final concentration of test compound or control compound was 2 µM.

Step 4: Aliquots of 50 µL were taken from the reaction solution at 0, 15, 30, 45 and 60 min. The reaction was stopped by the addition of 4 volumes of cold methanol with IS (200 nM imipramine, 200 nM labetalol and 2 µM ketoprofen). Samples were centrifuged at 3, 220 g for 40 minutes. Aliquot of 90 µL of the supernatant was mixed with 90 µL of ultra-pure H2O and then used for LC-MS/MS analysis.

Step 5: Data Analysis

All calculations were carried out using Microsoft Excel.

Peak areas were determined from extracted ion chromatograms. The slope value, k, was determined by linear regression of the natural logarithm of the remaining percentage of the parent drug vs. incubation time curve.

Results indicate that the formation of DNP is translatable between spices and occurs readily by common enzymes in the liver.

Example 12

Suggested Phase ½ Clinical Trial Inclusion Criteria

Inclusion Criteria:
2-3 markers of metabolic syndrome
10% fat in liver
ALT of 40 or higher
FIB4 panel over 1.1
Exclusion Criteria:
BMI<25, alcohol use
History of sinus tachycardia, ischemic disease or kidney dysfunction
Exploratory Efficacy Endpoints from Phase ½ Study
Liver fat quantification using MRI-PDFF and MRE
Circulating CK18
Liver mitochondrial activity non-invasive breath test (BreathID® System, Exalenz Biosciences)
Verify target engagement and PD
Responder ID and patient stratification
Rapid validation of design goals
BreathID® System utilized in multiple Phase II studies of NASH (NCT02314026, NCT01244503, NCT01281059)

Example 13

Synthesis of 1-[2-(2,4-Dinitro-phenoxy)-ethyl]-2-methyl-5-nitro-1H-imidazole (Compound #1 in Table A)

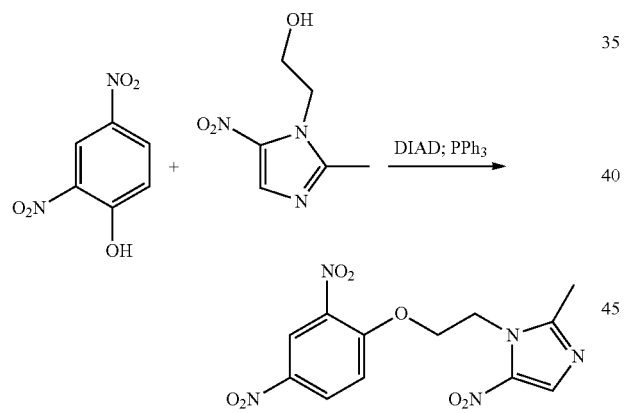

2,4-Dinitrophenol (wetted with ca. 20% water) (269 mg wet weight, 215 mg dry weight, 1.17 mmol) is dissolved in methylene chloride (2 mL) and stirred with anhydrous sodium sulfate at room temperature for 3 hours. The methylene chloride solution is decanted into a reaction flask and the sodium sulfate is washed with additional methylene chloride (2 mL). To the solution is added 2-(2-methyl-5-nitro-imidazol-1-yl)-ethanol (125 mg, 0.732 mmol) and triphenylphosphine (211 mg, 0.805 mmol). The mixture is stirred at room temperature until a solution is achieved. The solution is then cooled in an ice bath and treated with diisopropyl azodicarboxylate, DIAD (158 µL, 0.805 mmol). After 1 hour the ice bath is removed and the mixture is stirred overnight at room temperature. Crude product is purified on a silica gel column to isolate the product mixed with triphenylphosphine oxide. The solids are triturated with t-butyl methyl ether to remove the triphenylphosphine oxide to afford 1-[2-(2,4-Dinitro-phenoxy)-ethyl]-2-methyl-5-nitro-1H-imidazole. MS (ESI+) for $C_{12}H_{11}N_5O_7$ m/z 338.1 (M+H)$^+$.

Example 14

Synthesis of 1-Methyl-2-nitro-5-(4-nitro-phenoxymethyl)-1H-imidazole (Compound #3 in Table A)

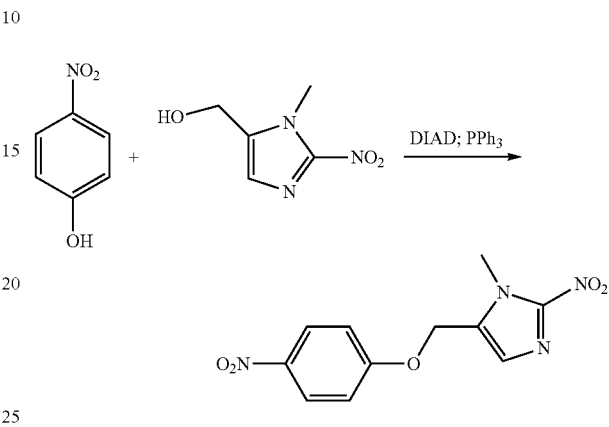

4-Nitrophenol (162 mg, 1.17 mmol) is dissolved in methylene chloride (2 mL). To the solution is added (3-methyl-2-nitro-3H-imidazol-4-yl)-methanol (115 mg, 0.732 mmol) and triphenylphosphine (211 mg, 0.805 mmol). The mixture is stirred at room temperature until a solution is achieved. The solution is then cooled in an ice bath and treated with diisopropyl azodicarboxylate, DIAD (158 µL, 0.805 mmol). After 1 hour the ice bath is removed and the mixture is stirred overnight at room temperature. Crude product is purified on a silica gel column to isolate the product mixed with triphenylphosphine oxide. The solids are triturated with t-butyl methyl ether to remove the triphenylphosphine oxide to afford 1-methyl-2-nitro-5-(4-nitro-phenoxymethyl)-1H-imidazole. MS (ESI+) for $C_{11}H_{10}N_4O_5$ m/z 279.1 (M+H)$^+$.

Example 15

Synthesis of 1-Methyl-2-nitro-5-(3-nitro-phenoxymethyl)-1H-imidazole (Compound #4 in Table A)

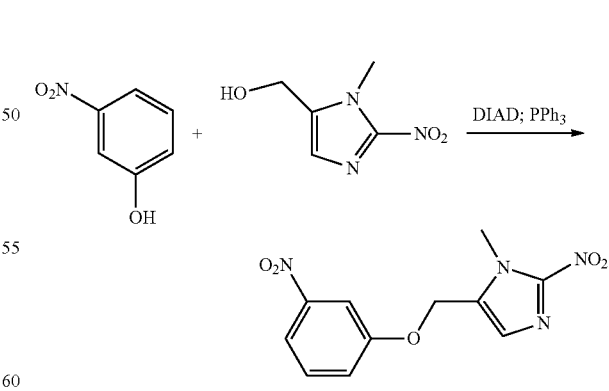

3-Nitrophenol (162 mg, 1.17 mmol) is dissolved in methylene chloride (2 mL). To the solution is added (3-methyl-2-nitro-3H-imidazol-4-yl)-methanol (115 mg, 0.732 mmol) and triphenylphosphine (211 mg, 0.805 mmol). The mixture is stirred at room temperature until a solution is achieved. The solution is then cooled in an ice bath and treated with diisopropyl azodicarboxylate, DIAD (158 μL, 0.805 mmol). After 1 hour the ice bath is removed and the mixture is stirred overnight at room temperature. Crude product is purified on a silica gel column to isolate the product mixed with triphenylphosphine oxide. The solids are triturated with t-butyl methyl ether to remove the triphenylphosphine oxide to afford 1-Methyl-2-nitro-5-(3-nitro-phenoxymethyl)-1H-imidazole. MS (ESI+) for $C_{11}H_{10}N_4O_5$ m/z 279.1 (M+H)$^+$.

Example 16 Synthesis of 5-(3,5-Dinitro-phenoxymethyl)-1-methyl-2-nitro-1H-imidazole (Compound #5 in Table A)

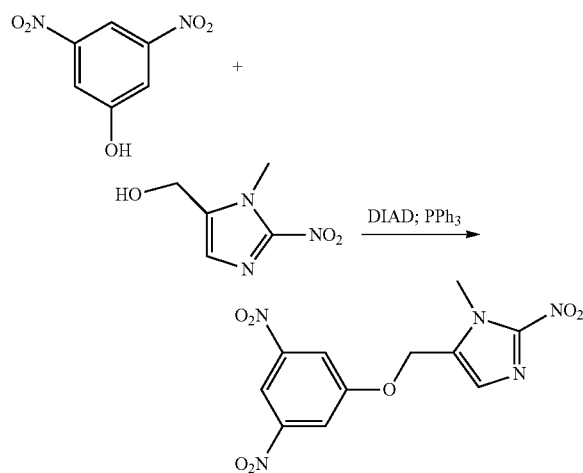

3,5-Dinitro-phenol (215 mg, 1.17 mmol) is dissolved in methylene chloride (2 mL). To the solution is added (3-methyl-2-nitro-3H-imidazol-4-yl)-methanol (115 mg, 0.732 mmol) and triphenylphosphine (211 mg, 0.805 mmol). The mixture is stirred at room temperature until a solution is achieved. The solution is then cooled in an ice bath and treated with diisopropyl azodicarboxylate, DIAD (158 μL, 0.805 mmol). After 1 hour the ice bath is removed and the mixture is stirred overnight at room temperature. Crude product is purified on a silica gel column to isolate the product mixed with triphenylphosphine oxide. The solids are triturated with t-butyl methyl ether to remove the triphenylphosphine oxide to afford 5-(3,5-dinitro-phenoxymethyl)-1-methyl-2-nitro-1H-imidazole. MS (ESI+) for $C_{11}H_9N_5O_7$ m/z 324.1 (M+H)$^+$.

Example 17

Synthesis of 5-(2,4-Dichloro-phenoxymethyl)-1-methyl-2-nitro-1H-imidazoleimidazole (Compound #6 in Table A)

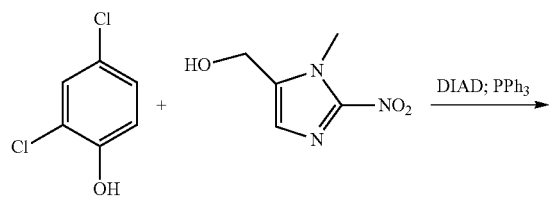

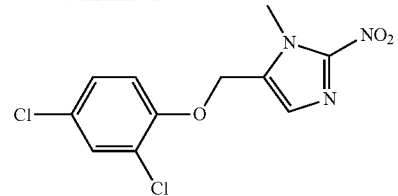

2,4-Dichloro-phenol (190 mg, 1.17 mmol) is dissolved in methylene chloride (2 mL). To the solution is added (3-methyl-2-nitro-3H-imidazol-4-yl)-methanol (115 mg, 0.732 mmol) and triphenylphosphine (211 mg, 0.805 mmol). The mixture is stirred at room temperature until a solution is achieved. The solution is then cooled in an ice bath and treated with diisopropyl azodicarboxylate, DIAD (158 μL, 0.805 mmol). After 1 hour the ice bath is removed and the mixture is stirred overnight at room temperature. Crude product is purified on a silica gel column to isolate the product mixed with triphenylphosphine oxide. The solids are triturated with t-butyl methyl ether to remove the triphenylphosphine oxide to afford 5-(2,4-dichloro-phenoxymethyl)-1-methyl-2-nitro-1H-imidazole. MS (ESI+) for $C_{11}H_9Cl_2N_3O_3$ m/z 301.1 (M+H)$^+$.

Example 18

Synthesis of 5-(2,6-Dichloro-4-nitro-phenoxymethyl)-1-methyl-2-nitro-1H-imidazole (Compound #8 in Table A)

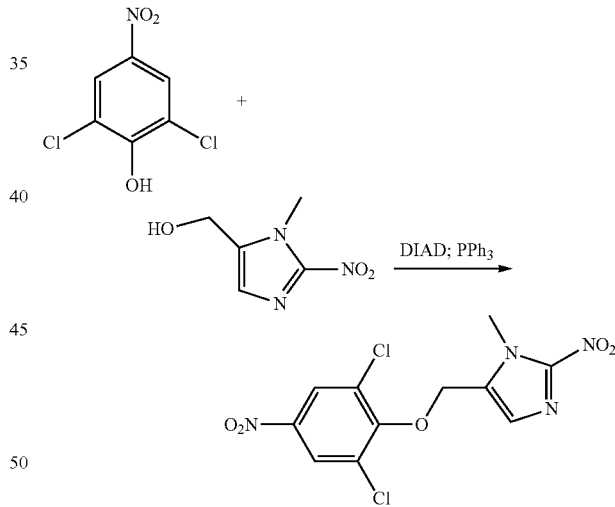

2,6-Dichloro-4-nitro-phenol (243 mg, 1.17 mmol) is dissolved in methylene chloride (2 mL). To the solution is added (3-methyl-2-nitro-3H-imidazol-4-yl)-methanol (115 mg, 0.732 mmol) and triphenylphosphine (211 mg, 0.805 mmol). The mixture is stirred at room temperature until a solution is achieved. The solution is then cooled in an ice bath and treated with diisopropyl azodicarboxylate, DIAD (158 μL, 0.805 mmol). After 1 hour the ice bath is removed and the mixture is stirred overnight at room temperature. Crude product is purified on a silica gel column to isolate the product mixed with triphenylphosphine oxide. The solids are triturated with t-butyl methyl ether to remove the triphenylphosphine oxide to afford 5-(2,6-dichloro-4-nitro-phenoxymethyl)-1-methyl-2-nitro-1H-imidazole. MS (ESI+) for $C_{11}H_8Cl_2N_4O_5$ m/z 347.0 (M+H)$^+$.

Example 19

Synthesis of 2-((2,4-dinitrophenoxy)methyl)-1-methyl-5-nitro-1H-imidazole (Compound #16 in Table A)

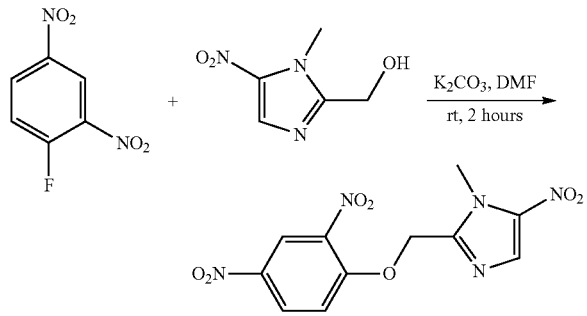

A mixture of (1-methyl-5-nitro-1H-imidazol-2-yl)methanol (176 mg, 1.12 mmol) and 1-fluoro-2,4-dinitrobenzene (250 mg, 1.34 mmol) and K$_2$CO$_3$ (465 mg, 3.36 mmol) in DMF (5 mL) was stirred 2 hours at ambient temperature. The reaction was worked-up by extraction. The residue was purified by prep-HPLC with the following condition: column: XBridge preparative C18 OBD column 19×150 mm, 5 um; mobile phase A: water (10 mmol/L NH$_4$HCO$_3$), mobile phase B: ACN; flow rate: 20 mL/min; gradient elution. The product-containing fractions were collected and then lyophilized to give 2-(2,4-dinitro-phenoxymethyl)-1-methyl-5-nitro-1H-imidazole as a yellow solid. LC-MS: (ES, m/z) 324. (M+H)$^+$. $^1$H-NMR: (400 MHz, DMSO-d$_6$) δ 8.79 (d, J=2.8 Hz, 1H), 8.57 (dd, J$_1$=2.8 Hz, J$_2$=9.2 Hz, 1H), 8.10 (s, 1H), 7.79 (d, J=9.6 Hz, 1H), 5.72 (s, 2H), 3.95 (s, 3H); analysis: C, 42.79; H, 3.43; N, 20.68; O, 33.25.

Formation of DNP from Compound B by Liver Microsomes

Following the experimental procedures described in Example 11 without changing experimental conditions but replacing Compound A with the title compound in human enzyme, the following results are obtained:

| Species | Assay Format | Formation of DNP (μM) | | | | | Formation Percentage (%) | | | | |
|---|---|---|---|---|---|---|---|---|---|---|---|
| | | 0 min | 15 min | 30 min | 45 min | 60 min | 0 min | 15 min | 30 min | 45 min | 60 min |
| Human | With NADPH | 0.031 | 0.038 | 0.025 | 0.023 | 0.018 | 1.56 | 1.90 | 1.26 | 1.13 | 0.91 |
| | Without NADPH | 0.017 | 0.015 | 0.014 | 0.014 | 0.013 | 0.83 | 0.75 | 0.72 | 0.69 | 0.63 |

Example 20

Synthesis of 2-[2-(2,4-Dinitro-phenoxy)-ethyl]-1-methyl-5-nitro-1H-imidazole (Compound #17 in Table A)

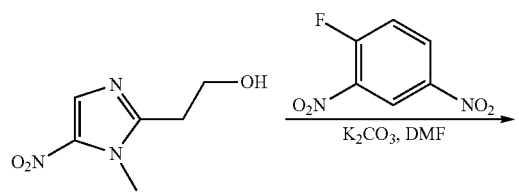

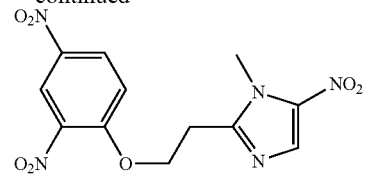

A mixture of 2-(1-methyl-5-nitro-1H-imidazol-2-yl)-ethanol (1.32 mmol) and 1-fluoro-2,4-dinitrobenzene (1.65 mmol) and K$_2$CO$_3$ (465 mg, 3.36 mmol) in DMF (5 mL) was stirred 2 hours at ambient temperature. The reaction was worked-up by extraction. The residue was purified by prep-HPLC with the following condition: column: XBridge preparative C18 OBD column 19×150 mm, 5 um; mobile phase A: water (10 mmol/L NH$_4$HCO$_3$), mobile phase B: ACN; flow rate: 20 mL/min; gradient elution. The product-containing fractions were collected and then lyophilized to give 2-[2-(2,4-dinitro-phenoxy)-ethyl]-1-methyl-5-nitro-1H-imidazole. LC-MS: (ES, m/z) 338.07 (M+H)$^+$; analysis: C, 42.62; H, 3.20; N, 20.83; O, 33.32.

Example 21

Synthesis of 1-Methyl-5-nitro-2-(4-nitro-phenoxymethyl)-1H-imidazole (Compound #18 in Table A)

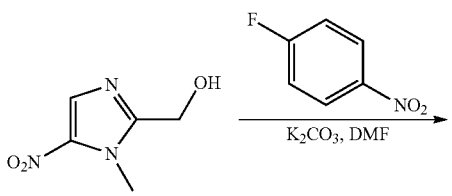

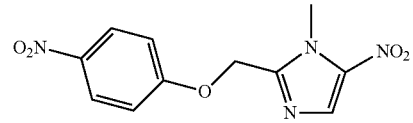

A mixture of 2-(1-methyl-5-nitro-1H-imidazol-2-yl)-ethanol (1.24 mmol) and 1-fluoro-4-nitrobenzene (1.45 mmol) and K$_2$CO$_3$ (465 mg, 3.36 mmol) in DMF (5 mL) was stirred 2 hours at ambient temperature followed by heating. The reaction was worked-up by extraction. The residue was purified by prep-HPLC with the following condition: column: XBridge preparative C18 OBD column 19×150 mm, 5 um; mobile phase A: water (10 mmol/L NH$_4$HCO$_3$), mobile phase B: ACN; flow rate: 20 mL/min; gradient elution. The product-containing fractions were collected and then lyophilized to give 1-methyl-5-nitro-2-(4-nitro-phenoxymethyl)-1H-imidazole. LC-MS: (ES, m/z) 279.07 (M+H)$^+$; analysis: C, 47.35; H, 3.71; N, 20.24; O, 28.82.

Example 22

Synthesis of 1-Methyl-5-nitro-2-(3-nitro-phenoxymethyl)-1H-imidazole (Compound #19 in Table A)

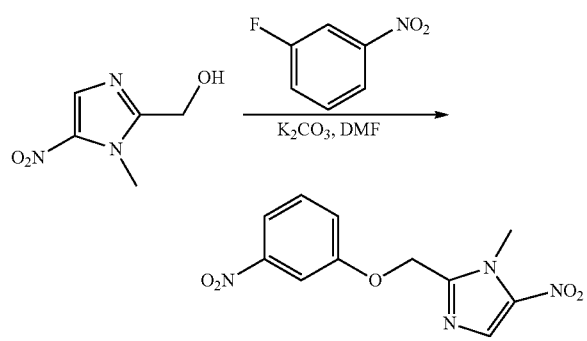

A mixture of 2-(1-methyl-5-nitro-1H-imidazol-2-yl)-ethanol (1.32 mmol) and 1-fluoro-3-nitrobenzene (1.67 mmol) and K$_2$CO$_3$ (465 mg, 3.36 mmol) in DMF (5 mL) was stirred 2 hours at ambient temperature followed by heating. The reaction was worked-up by extraction. The residue was purified by prep-HPLC with the following condition: column: XBridge preparative C18 OBD column 19×150 mm, 5 um; mobile phase A: water (10 mmol/L NH$_4$HCO$_3$), mobile phase B: ACN; flow rate: 20 mL/min; gradient elution. The product-containing fractions were collected and then lyophilized to give 1-methyl-5-nitro-2-(3-nitro-phenoxymethyl)-1H-imidazole. LC-MS: (ES, m/z) 279.07 (M+H)$^+$; analysis: C, 47.53; H, 3.69; N, 20.24; O, 28.85.

Example 23

Synthesis of 2-(3,5-Dinitro-phenoxymethyl)-1-methyl-5-nitro-1H-imidazole (Compound #20 in Table A)

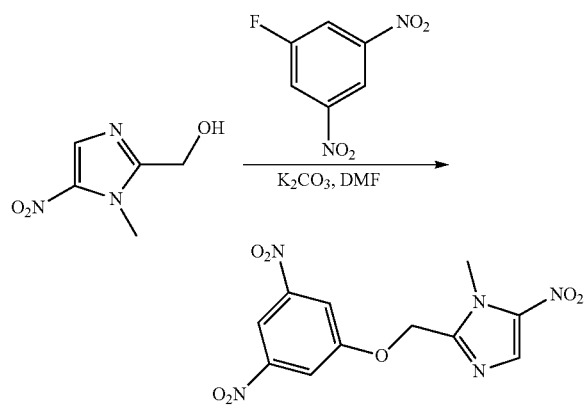

A mixture of 2-(1-methyl-5-nitro-1H-imidazol-2-yl)-ethanol (1.22 mmol) and 3,5-di-nitro-1-fluorobenzene (1.54 mmol) and K$_2$CO$_3$ (465 mg, 3.36 mmol) in DMF (5 mL) was stirred 2 hours at ambient temperature followed by heating. The reaction was worked-up by extraction. The residue was purified by prep-HPLC with the following condition: column: XBridge preparative C18 OBD column 19×150 mm, 5 um; mobile phase A: water (10 mmol/L NH$_4$HCO$_3$), mobile phase B: ACN; flow rate: 20 mL/min; gradient elution. The product-containing fractions were collected and then lyophilized to give 2-(3,5-dinitro-phenoxymethyl)-1-methyl-5-nitro-1H-imidazole. LC-MS: (ES, m/z) 324.05 (M+H)$^+$; analysis: C, 40.90; H, 2.89; N, 21.72; O, 34.60.

Example 24

Synthesis of 2-(2,4-Dichloro-phenoxymethyl)-1-methyl-5-nitro-1H-imidazole (Compound #21 in Table A)

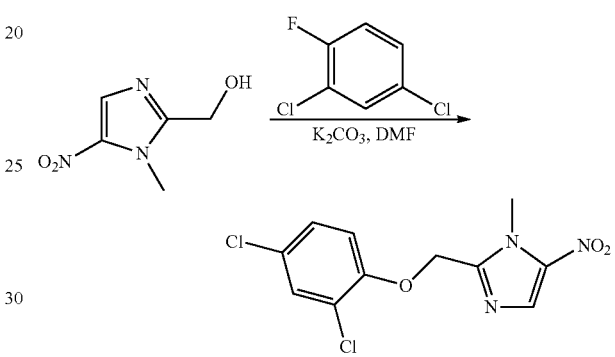

A mixture of 2-(1-methyl-5-nitro-1H-imidazol-2-yl)-ethanol (1.25 mmol) and 2,4-di-chloro-1-fluorobenzene (1.45 mmol) and K$_2$CO$_3$ (465 mg, 3.36 mmol) in DMF (5 mL) was stirred 2 hours at ambient temperature followed by heating. The reaction was worked-up by extraction. The residue was purified by prep-HPLC with the following condition: column: XBridge preparative C18 OBD column 19×150 mm, 5 um; mobile phase A: water (10 mmol/L NH$_4$HCO$_3$), mobile phase B: ACN; flow rate: 20 mL/min; gradient elution. The product-containing fractions were collected and then lyophilized to give 2-(2,4-dichloro-phenoxymethyl)-1-methyl-5-nitro-1H-imidazole. LC-MS: (ES, m/z) 302.00 (M+H)$^+$; analysis: C, 43.78; H, 3.08; Cl, 23.52; N, 13.81; O, 15.99.

Example 25

Synthesis of 2-(2,6-Dichloro-4-nitro-phenoxymethyl)-1-methyl-5-nitro-1H-imidazole (Compound #22 in Table A)

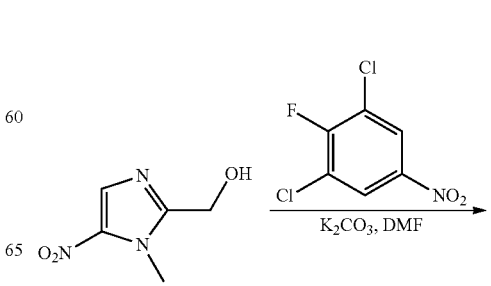

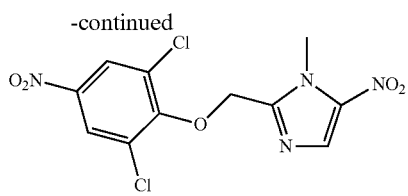

A mixture of 2-(1-methyl-5-nitro-1H-imidazol-2-yl)-ethanol (1.15 mmol) and 1,3-dichloro-2-fluoro-5-nitro-benzene (1.24 mmol) and $K_2CO_3$ (465 mg, 3.36 mmol) in DMF (5 mL) was stirred 2 hours at ambient temperature followed by heating. The reaction was worked-up by extraction. The residue was purified by prep-HPLC with the following condition: column: XBridge preparative C18 OBD column 19×150 mm, 5 um; mobile phase A: water (10 mmol/L $NH_4HCO_3$), mobile phase B: ACN; flow rate: 20 mL/min; gradient elution. The product-containing fractions were collected and then lyophilized to give 2-(2,6-dichloro-4-nitro-phenoxymethyl)-1-methyl-5-nitro-1H-imidazole. LC-MS: (ES, m/z) 346. $(M+H)^+$; analysis: C, 38.01; H, 2.22; Cl, 20.13; N, 16.19; O, 23.15.

Example 26

Synthesis of Compounds 11, 12, 13, 14, and 15 in Table A

In a reaction vessel, a mixture of the imidazole compound (1 molar equivalent), methylene iodide (1 molar equivalent), the potassium salt of the phenol compound (1 molar equivalent), dry triethylamine (1 molar equivalent), and a catalytic amount of TBAB were dissolved in dry acetonitrile. The solution was refluxed for 2 hours and followed by evaporation of the solvent. The residue was then dissolved in $CHCl_3$ and washed with water (2×200 mL). The organic layer was dried with anhydrous sodium sulfate, filtered and evaporated to give the crude product. Further purification was performed using column chromatography on silica gel.

I claim:
1. 5-[(2,4-dinitrophenoxy)methyl]-1-methyl-2-nitro-1H-imidazole or a pharmaceutically acceptable salt thereof.
2. A pharmaceutical composition comprising a pharmaceutically acceptable carrier and the compound of claim 1 or a pharmaceutically acceptable salt thereof.
3. A method of treating mitochondria-related disorders or conditions in a mammal in need thereof comprising administering to the mammal an effective amount of the compound of claim 1 or a pharmaceutically acceptable salt thereof.
4. The method of claim 3, wherein the disorder is obesity, diabetes, or insulin resistance or intolerance.
5. The method of claim 3 wherein the disorder is non-alcoholic fatty liver disease (NAFLD), non-alcoholic steatohepatitis (NASH), hepatic steatosis, or type 2 diabetes (T2DM).
6. The method of claim 3, wherein the disorder is obesity, or excess body fat.
7. The method of claim 3, wherein the disorder is dyslipidemia.
8. The method of claim 3, wherein the disorder is cardiovascular disease.
9. The method of claim 3, wherein the disorder is heart disease.
10. The method of claim 3, wherein the disorder is atherosclerosis.
11. A method of reducing adiposity, controlling or preventing of weight gain in a mammal in need thereof comprising administering to the mammal an effective amount of the compound of claim 1 or a pharmaceutically acceptable salt thereof.
12. A method for stimulating oxygen consumption rate (OCR) in a mammal in need thereof comprising administering to the mammal an effective amount of the compound of claim 1 or a pharmaceutically acceptable salt thereof.
13. A method for treating inflammation and fibrosis resulting in NASH in a mammal in need thereof comprising administering to the mammal an effective amount of the compound of claim 1 or a pharmaceutically acceptable salt thereof.

* * * * *

UNITED STATES PATENT AND TRADEMARK OFFICE
CERTIFICATE OF CORRECTION

PATENT NO. : 10,618,875 B2
APPLICATION NO. : 16/475390
DATED : April 14, 2020
INVENTOR(S) : Shaharyar Khan It is certified that error appears in the above-identified patent and that said Letters Patent is hereby corrected as shown below:

In the Specification

At Column 14, Table A, the name of Compound #2 (Compound A):
"5-[(2,5-dinitrophenoxy)methyl]-1-methyl-2-nitro-1H-imidazole" should read as -- 5-[(2,4-dinitrophenoxy)methyl]-1-methyl-2-nitro-1H-imidazole --.

Signed and Sealed this
Twentieth Day of February, 2024

Katherine Kelly Vidal
*Director of the United States Patent and Trademark Office*